US012748113B2

(12) United States Patent
Iida et al.

(10) Patent No.: US 12,748,113 B2
(45) Date of Patent: Sep. 29, 2026

(54) METHOD FOR ACCUMULATING MICROSCOPIC OBJECTS, AND METHOD FOR DETECTING MICROSCOPIC OBJECTS USING SAME

(71) Applicant: University Public Corporation Osaka, Osaka (JP)

(72) Inventors: Takuya Iida, Sakai (JP); Shiho Tokonami, Sakai (JP); Masatoshi Kanoda, Sakai (JP)

(73) Assignee: University Public Corporation Osaka, Osaka (JP)

( * ) Notice: Subject to any disclaimer, the term of this patent is extended or adjusted under 35 U.S.C. 154(b) by 546 days.

(21) Appl. No.: 18/289,790

(22) PCT Filed: Apr. 28, 2022

(86) PCT No.: PCT/JP2022/019417
§ 371 (c)(1),
(2) Date: Nov. 7, 2023

(87) PCT Pub. No.: WO2022/234830
PCT Pub. Date: Nov. 10, 2022

(65) Prior Publication Data

US 2024/0272157 A1 Aug. 15, 2024

(30) Foreign Application Priority Data

May 7, 2021 (JP) ................................ 2021-079294

(51) Int. Cl.
*G01N 33/569* (2006.01)
*G01N 21/27* (2006.01)
(Continued)

(52) U.S. Cl.
CPC ..... *G01N 33/56983* (2013.01); *G01N 21/272* (2013.01); *G01N 21/4133* (2013.01);
(Continued)

(58) Field of Classification Search
CPC ..... B01L 2200/0668; B01L 2300/0887; B01L 2300/1861; B01L 2400/0442;
(Continued)

(56) References Cited

U.S. PATENT DOCUMENTS

2014/0293731 A1 10/2014 Baaske et al.
2015/0316480 A1 11/2015 Seidel et al.
(Continued)

FOREIGN PATENT DOCUMENTS

JP 2018194550 A 12/2018
WO WO-2018159706 A1 9/2018
WO WO-2020218347 A1 10/2020

OTHER PUBLICATIONS

Damage-free light-induced assembly of intestinal bacteria with a bubble-mimetic substrate. Communications Biology, Mar. 22, 2021, 4:385, pp. 1-7, pp. S1-S10, doi: 10.1038/s42003-021-01807-w Fig. 1-5.
(Continued)

*Primary Examiner* — Jennifer Wecker
(74) *Attorney, Agent, or Firm* — MARSHALL, GERSTEIN & BORUN LLP

(57) ABSTRACT

A first step is preparing a sample in contact with a bowl region. A second step is irradiating the bowl region with a laser beam to generate a microbubble in an irradiation region of the laser beam and accumulate a plurality of microscopic objects around the microbubble. The bowl region includes a metallic thin film, a conductive polymer film, and a metallic thin film. Conductive polymer film has a plurality of bowl-like structures periodically arranged on metallic thin film. The sizes of the plurality of bowl-like structures and the irradiation region of the laser beam are determined such that at least two of the plurality of bowl-like structures are entirely included in the irradiation region.

15 Claims, 48 Drawing Sheets

(51) Int. Cl.

| | |
|---|---|
| ***G01N 21/41*** | (2006.01) |
| ***G01N 21/64*** | (2006.01) |
| ***G01N 33/543*** | (2006.01) |

(52) U.S. Cl.
CPC ... *G01N 21/6428* (2013.01); *G01N 33/54386* (2013.01); *G01N 2021/6439* (2013.01); *G01N 2201/06113* (2013.01); *G01N 2333/165* (2013.01); *G01N 2469/10* (2013.01)

(58) Field of Classification Search
CPC ..... B01L 2400/0445; B01L 2400/0448; B01L 2400/0469; B01L 3/502761; C12M 47/02; G01N 1/4022; G01N 2021/6421; G01N 2021/6439; G01N 21/272; G01N 21/31; G01N 21/4133; G01N 21/6428; G01N 21/6458; G01N 2201/06113; G01N 2333/165; G01N 2469/10; G01N 33/54386; G01N 33/56983
See application file for complete search history.

(56) References Cited

U.S. PATENT DOCUMENTS

| | | | | |
|---|---|---|---|---|
| 2019/0383708 | A1* | 12/2019 | Iida | G01N 1/28 |
| 2020/0182770 | A1* | 6/2020 | Tokonami | B01L 3/50851 |
| 2022/0226814 | A1* | 7/2022 | Iida | G01N 1/44 |

OTHER PUBLICATIONS

International Search Report and Written Opinion for Application No. PCT/JP2022/019417 dated Jul. 12, 2022.

* cited by examiner

<MICRO-BOWL SUBSTRATE>

<NANO-BOWL SUBSTRATE>

| | SAMPLE 1 | SAMPLE 2 | SAMPLE 3 |
|---|---|---|---|
| TOTAL AMOUNT (LIVING BACTERIA+DEAD BACTERIA) |  |  |  |
| KILLED BACTERIA |  |  |  |
| SURVIVAL RATE | 91.07% | 95.11% | 91.00% |

⟨CONTROL NANOPARTICLES⟩

| | ONLY MICROPARTICLES (BB) | ONLY NANOPARTICLES (YG) |
|---|---|---|
| BEFORE START OF LIGHT IRRADIATION |   |   |
| AFTER STOP OF LIGHT IRRADIATION |   |   |
| FLUORESCENT IMAGE (FILTER UV) |   | |
| FLUORESCENT IMAGE (FILTER BLUE) | |   |

<MICROPARTICLES (BB)+ NANOPARTICLES (YG)>

| | |
|---|---|
| IMMEDIATELY AFTER STOP OF LIGHT IRRADIATION |   |
| AFTER MICROBUBBLE DISAPPEAR |   |
| FLUORESCENT IMAGE (FILTER UV) |   |
| FLUORESCENT IMAGE (FILTER BLUE) |   |

METHOD FOR ACCUMULATING MICROSCOPIC OBJECTS, AND METHOD FOR DETECTING MICROSCOPIC OBJECTS USING SAME

TECHNICAL FIELD

The present disclosure relates to a method for accumulating microscopic objects and a method for detecting microscopic objects using the same, and more specifically relates to a technique of accumulating microscopic objects dispersed in a liquid sample.

BACKGROUND

Japanese Patent Laying-Open No. 2018-194550 discloses a detection kit for an analyte, the detection kit using detection light to detect the analyte that may be contained in a sample. The detection kit includes a substrate and first to third thin films. The first thin film is made of a metal and is disposed on the substrate. The second thin film has a plurality of recesses, each having an inner wall surface forming a bowl-like structure. The second thin film is disposed on the first thin film. The third thin film is made of a metal and is disposed on at least a part in the bowl-like structures.

SUMMARY OF INVENTION

It is desirable to accumulate microscopic objects dispersed in a liquid sample even if the content of microscopic objects is small. In view of the suppression of thermal damage or the like to accumulated microscopic objects, it is desirable to accumulate microscopic objects using a minimum output of light. Thus, a technique of accumulating a small amount of microscopic objects using low-output light, in other words, a technique of efficiently accumulating microscopic objects has been demanded.

The present disclosure has been devised to solve the above problem. An object of the present disclosure is to efficiently accumulate a plurality of microscopic objects dispersed in a liquid sample.

In an aspect of the present disclosure, a method for accumulating a plurality of microscopic objects dispersed in a liquid sample. The method for accumulating microscopic objects includes first and second steps. The first step is preparing the liquid sample in contact with a photothermal conversion region. The second step is irradiating the photothermal conversion region with light having a wavelength within an absorption wavelength range of the photothermal conversion region to generate a bubble in an irradiation region of light and accumulate the plurality of microscopic objects around the bubble. The photothermal conversion region includes a first thin film, a structure, and a second thin film. The first thin film includes a first material that converts the light into heat. The structure has a plurality of non-penetrating pores periodically arranged on the first thin film. The second thin film includes a second material that converts the light into heat and is disposed on at least a part of the structure. The sizes of the plurality of non-penetrating pores and the irradiation region are determined such that at least two of the plurality of non-penetrating pores are entirely included in the irradiation region in a top view of the photothermal conversion region.

In another aspect of the present disclosure, a method for detecting microscopic objects includes: the method for accumulating microscopic objects; detecting, by a receiver, light from the liquid sample irradiated with the light; and detecting the plurality of microscopic objects in the liquid sample on a basis of a signal from the receiver.

According to the present disclosure, a plurality of microscopic objects dispersed in a liquid sample can be efficiently accumulated.

DETAILED DESCRIPTION

<Description of Terms>

Figure 1:
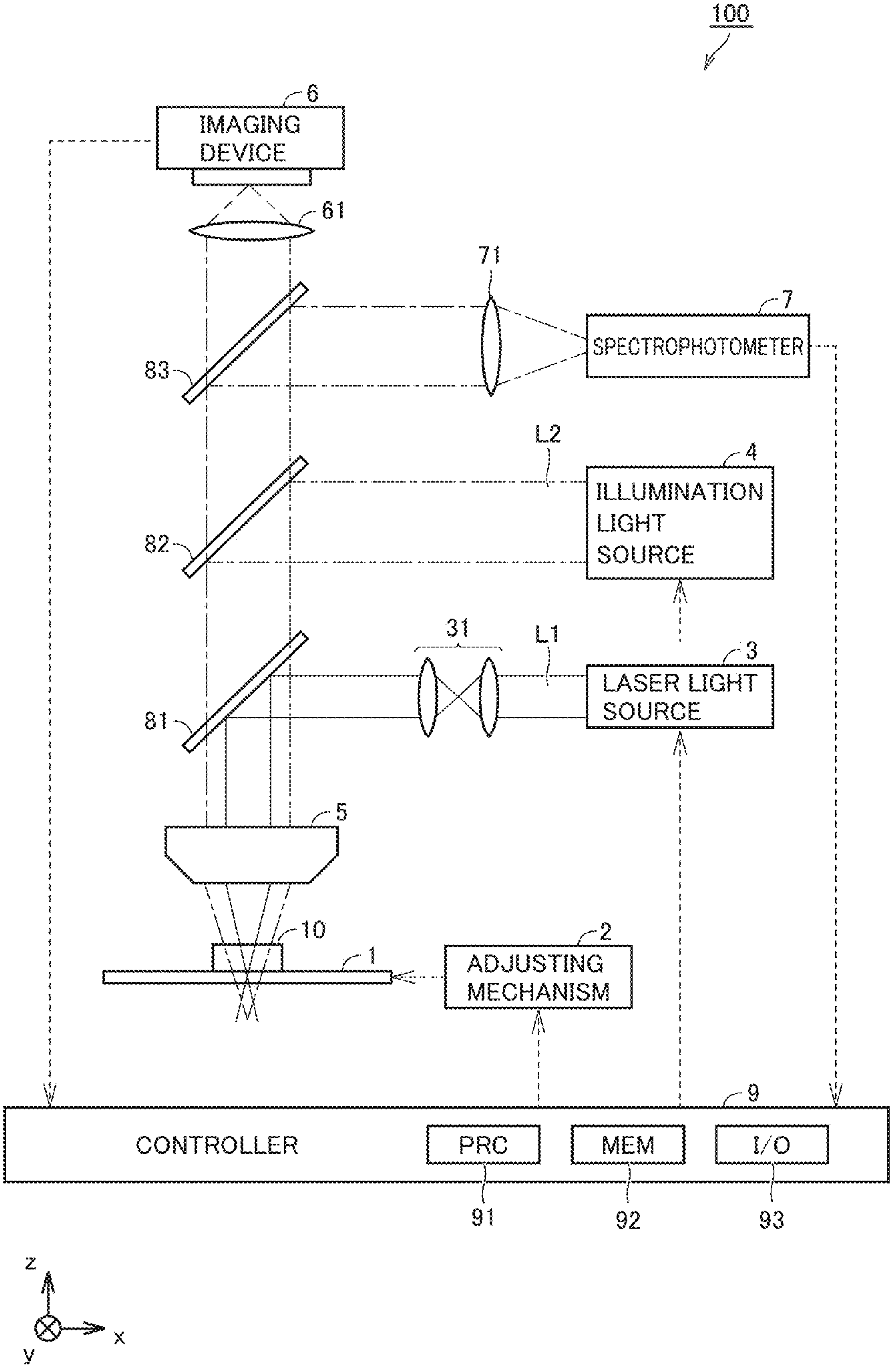
FIG. 1 is a diagram illustrating an example of the overall configuration of a detection system of microscopic objects according to Embodiment 1.

In the present disclosure and embodiments, "nanometer order" includes a range from 1 nm to 1000 nm (=1 μm). "Micrometer order" includes a range from 1 μm to 1000 μm (=1 mm). Thus, "a range from the nanometer order to the micrometer order" includes a range from 1 nm to 1000 μm. "A range from the nanometer order to the micrometer order" typically indicates a range from several nm to several hundred μm, preferably indicates a range from 100 nm to 100 μm, and more preferably indicates a range from several hundred nm to several tens of μm.

In the present disclosure and embodiments, "microscopic object" means an object in sizes ranging from the nanometer order to the micrometer order. The shape of the microscopic object is not particularly limited and may be, for example, a sphere, an oval sphere, or a rod (pole). If the microscopic object is an oval sphere, the oval sphere may have a length in a range from the nanometer order to the micrometer order in at least one of the major axis direction and the minor axis direction of the oval sphere. If the microscopic object is a rod, at least one of the width and the length of the rod may be set in a range from the nanometer order to the micrometer order.

Examples of the microscopic object include metallic nanoparticles, metallic nanoparticle assemblies, metallic nanoparticle accumulated structures, semiconductor nanoparticles, organic nanoparticles, and PM (Particulate Matter). "Metallic nanoparticles" are metallic particles in the size of nanometer order. "Metallic nanoparticle assemblies" are assemblies formed by the aggregation of a plurality of metallic nanoparticles. "Metallic nanoparticle accumulated structures" are structures in which, for example, a plurality of metallic nanoparticles are fixed on a surface of a base material (resin beads or the like) with an interaction portion interposed therebetween, with gaps between each other and spaced at intervals equal to or smaller than the diameter of the metallic nanoparticle. "Semiconductor nanoparticles" are semiconductor particles in the size of nanometer order. "Organic nanoparticles" are particles containing an organic compound in the size of nanometer order. "Resin beads" are resin particles in sizes ranging from the nanometer order to the micrometer order. "PM" indicates a particulate matter in the size of micrometer order. Examples of the PM include PM 2.5 and SPM (Suspended Particulate Matter).

A microscopic object may be a tissue-derived biomaterial (biological substance). More specifically, microscopic objects may include, for example, cells, microorganisms (such as a germ and a fungus), biopolymers (such as protein, nucleic acid, lipid, and polysaccharide), antigens (such as an allergen), antibodies, and viruses.

In the present disclosure and embodiments, unit lattices may include a tetragonal lattice, a rectangular lattice, an orthorhombic lattice, a face-centered rectangular lattice, and a hexagonal lattice (corresponding to a honeycomb shape, which will be described later). At the positions of a plurality of lattice points of a unit lattice, non-penetrating pores are formed. "Honeycomb shape" means a shape having a plurality of regular hexagons arranged in a hexagonal lattice (like a honeycomb) in the two-dimensional direction. A non-penetrating pore is formed for each of the regular hexagons. "Non-penetrating pore" is a pore having an opening in sizes ranging from the nanometer order to the micrometer order. The shape of the non-penetrating pore is not particularly limited and may include any shapes including a cylinder, a prism, or a sphere (e.g., a hemisphere or a semi-elliptical sphere).

In the present disclosure and embodiments, "microbubbles" means bubbles on the micrometer order.

In the present disclosure and embodiments, "visible range" means a wavelength range of 360 nm to 760 nm. A near-infrared range means a wavelength range of 760 nm to 2 μm.

The embodiments according to the present disclosure will be specifically described below with reference to the accompanying drawings. The same parts or equivalent parts in the drawings are indicated by the same reference numerals and a repetition of a description thereof will not be repeated. Hereinafter, the x direction and the y direction indicate horizontal directions. The x direction and the y direction are orthogonal to each other. The z direction indicates the vertical direction. Gravity is directed downward in the z direction. Directed upward in the z direction may be abbreviated as "upward" and directed downward in the z direction may be abbreviated as "downward."

Embodiment 1

<Overall Configuration of Detection System>

FIG. 1 is a diagram illustrating an example of the overall configuration of a detection system 100 of microscopic objects according to Embodiment 1. Detection system 100 includes an xyz-axis stage 1, an adjusting mechanism 2, a laser light source 3, lenses 31, an illumination light source 4, an objective lens 5, an imaging device 6, a lens 61, a spectrophotometer 7, a lens 71, a dichroic mirror 81, half mirrors 82 and 83, and a controller 9.

Xyz-axis stage 1 is configured to set a detection kit 10. A sample is held on detection kit 10. The sample is a liquid sample that may contain microscopic objects (resin beads, viruses or the like). The configuration of detection kit 10 will be specifically described below referring to FIGS. 2 to 5.

Adjusting mechanism 2 adjusts the relative positional relationship between xyz-axis stage 1 and objective lens 5 according to a command from controller 9. In the present embodiment, the position of objective lens 5 is fixed. Thus, the relative positional relationship between xyz-axis stage 1 and objective lens 5 is adjusted by positioning xyz-axis stage 1 in the x direction, the y direction, and the z direction. As adjusting mechanism 2, for example, drive mechanisms (not illustrate) such as a servo motor and a focusing handle provided for a microscope may be used. The specific configuration of adjusting mechanism 2 is not particularly limited. Adjusting mechanism 2 may be configured to adjust the position of objective lens 5.

Laser light source 3 emits a laser beam (denoted as L1) of a continuous wave (CW) according to a command from controller 9. The wavelength of the laser beam is a wavelength included in the absorption wavelength range of metallic thin films 211 and 113 (described later), for example, the wavelength is a wavelength of a near-infrared range (800 nm and 1064 nm in an example described later). The laser beam is adjusted into parallel beams (collimated beams) through lenses 31 and then propagates to dichroic mirror 81.

Dichroic mirror 81 is disposed between lenses 31 and objective lens 5. Dichroic mirror 81 reflects light of the wavelength range (e.g., a near-infrared range) of a laser beam from the laser light source. Meanwhile, dichroic mirror 81 passes light outside the wavelength range (e.g., a visible range). The laser beam reflected by dichroic mirror 81 propagates to objective lens 5.

Illumination light source 4 emits white light (denoted as L2) for illuminating a sample on detection kit 10, according to a command from controller 9. As an example, a halogen lamp can be used as illumination light source 4. Illumination light source 4 may include an optical system for converting white light into a parallel beam. White light propagates to half mirror 82.

Half mirror 82 is disposed between illumination light source 4 and dichroic mirror 81. Half mirror 82 passes half of white light from illumination light source 4 and reflects the other half. White light reflected by half mirror 82 passes through dichroic mirror 81 and propagates to objective lens 5.

Objective lens 5 is used for condensing a laser beam from laser light source 3 and irradiating detection kit 10 with the laser beam. Objective lens 5 is used also for condensing white light from laser light source 4 and irradiating detection kit 10 with the white light. Objective lens 5 is used also for bringing in white light reflected by detection kit 10. The white light brought in by objective lens 5 passes through dichroic mirror 81 and half mirror 82 and propagates to half mirror 83.

Half mirror 83 is disposed between half mirror 82 and lens 61 and between half mirror 82 and lens 71. Half mirror 83 passes half of white light brought in by objective lens 5 from detection kit 10 and reflects the other half. White light having passed through half mirror 83 is condensed by lens 61 and is guided to imaging device 6. Meanwhile, white light reflected by half mirror 83 is condensed by lens 71 and is guided to spectrophotometer 7.

Imaging device 6 captures an image of the sample on detection kit 10 and outputs the captured image to controller 9 according to a command from controller 9. The image captured by imaging device 6 may be a still image or a moving image. As imaging device 6, a camera including a CCD (Charge Coupled Device) image sensor or a CMOS (Complementary Metal Oxide Semiconductor) image sensor can be used.

Spectrophotometer 7 measures the reflection spectrum of detection kit 10 according to a command from controller 9 and outputs the result of measurement to controller 9. Spectrophotometer 7 includes, for example, a diffraction grating, a light receiving element, a shutter, and a slit (none of them are illustrated). Light incident on spectrophotometer 7 passes through the slit and then reaches the diffraction grating. In the diffraction grating, incident light is reflected in a direction corresponding to the wavelength. The surface of the light receiving element is divided into a plurality of unit regions. Light reflected by the diffraction grating enters the unit region corresponding to the wavelength among the plurality of unit regions of the light receiving element. Thereafter, the reflection spectrum is acquired on the basis of an intensity value in each of the unit regions.

Spectrophotometer 7 is preferably capable of measuring a reflection spectrum in a wavelength range (for example, a wavelength range from a visible range to a near-infrared range) wider than the absorption wavelength range of metallic thin films 211 and 113. Moreover, spectrophotometer 7 preferably has the minimum wavelength resolution as small as possible. The wavelength resolution of spectrophotometer 7 is, for example, 10 nm or less, 5 nm or less, 2 nm or less, or 1 nm or less and is not limited thereto.

Controller 9 includes a processor 91, e.g., a CPU (Central Processing Unit), a memory 92, e.g., a ROM (Read Only Memory) and a RAM (Random Access Memory), and an input/output port 93 for obtaining various signals. Processor 91, memory 92, and input/output port 93 are not illustrated. Controller 9 controls the devices (adjusting mechanism 2, laser light source 3, illumination light source 4, imaging device 6, and spectrophotometer 7) in detection system 100. Moreover, controller 9 detects microscopic objects contained in the sample on the basis of the image captured by imaging device 6 or the reflection spectrum measured by spectrophotometer 7. The detection method will be described later.

The optical system of detection system 100 in FIG. 1 is merely exemplary. The optical system of detection system 100 is not limited if a laser beam from laser light source 3 and white light from illumination light source 4 can be guided to objective lens 5 and white light from detection kit 10 can be guided to imaging device 6 and spectrophotometer 7. For example, illumination light source 4 may be disposed below xyz-axis stage 1. In this case, white light is emitted from illumination light source 4 to detection kit 10 and imaging device 6 that are disposed above illumination light source 4. The optical system of detection system 100 may include other optical components (such as a filter and an optical fiber) instead of or in addition to dichroic mirror 81 and half mirrors 82 and 83.

<Configuration of Detection Kit>

Figure 2:
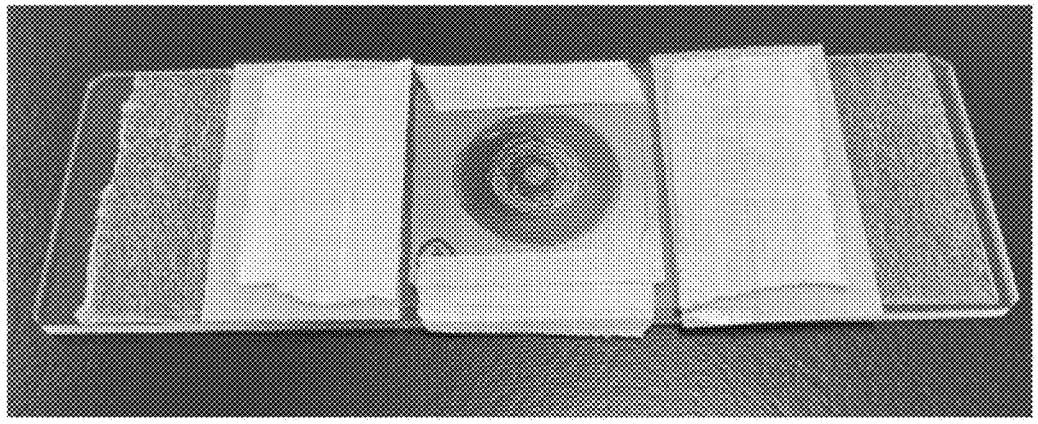
FIG. 2 is a diagram illustrating an image of an actually fabricated detection kit.
Figure 3:
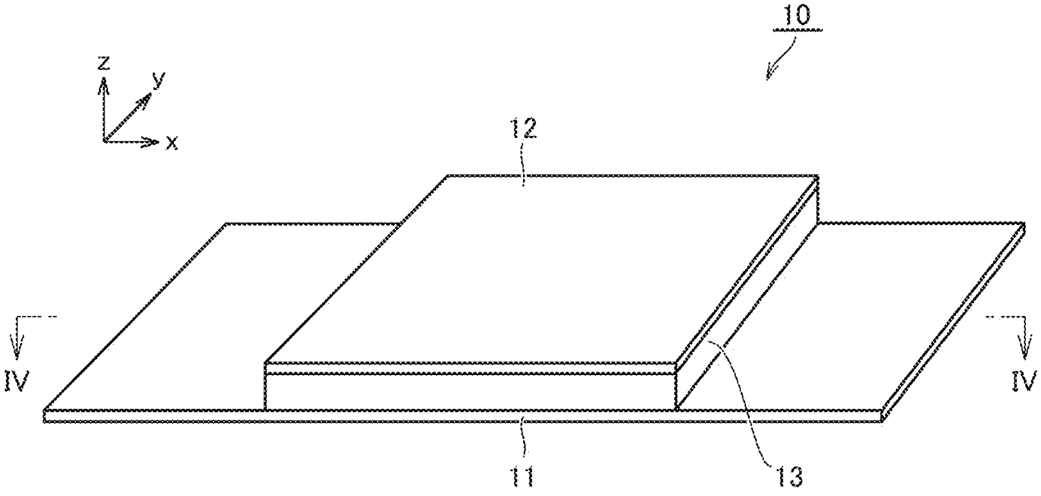
FIG. 3 is a perspective view of the detection kit.
Figure 4:
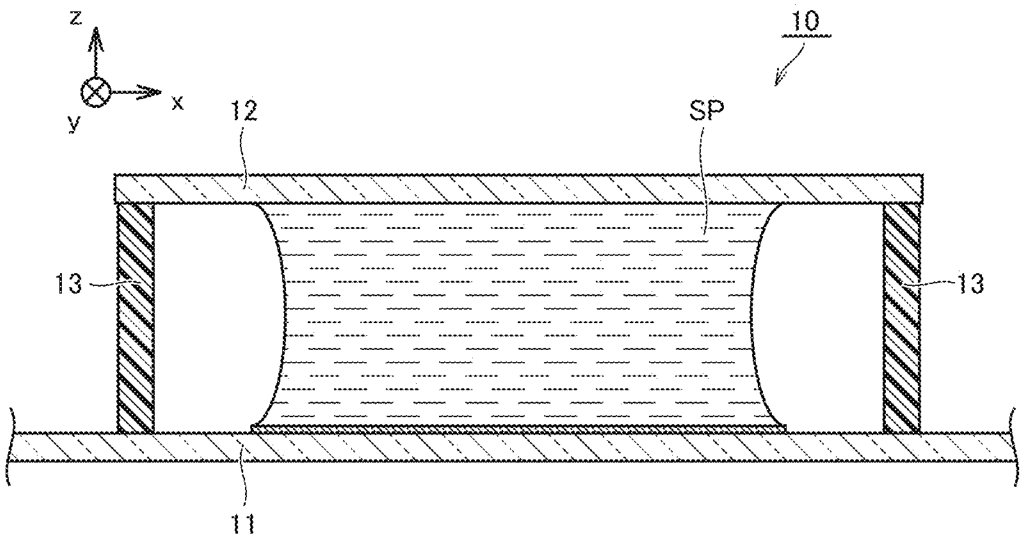
FIG. 4 is a cross-sectional view of the detection kit taken along line IV-IV of FIG. 3.

FIG. 2 is a diagram illustrating an image of actually fabricated detection kit 10. FIG. 3 is a perspective view of detection kit 10. FIG. 4 is a cross-sectional view of detection kit 10 taken along line IV-IV of FIG. 3. Referring to FIGS. 2 to 4, detection kit 10 is a container configured to hold a sample. In this example, detection kit 10 is flat-shaped. The shape of detection kit 10 is not particularly limited. Detection kit 10 includes a bottom portion 11, a top portion 12, and side portions 13.

Figure 5:
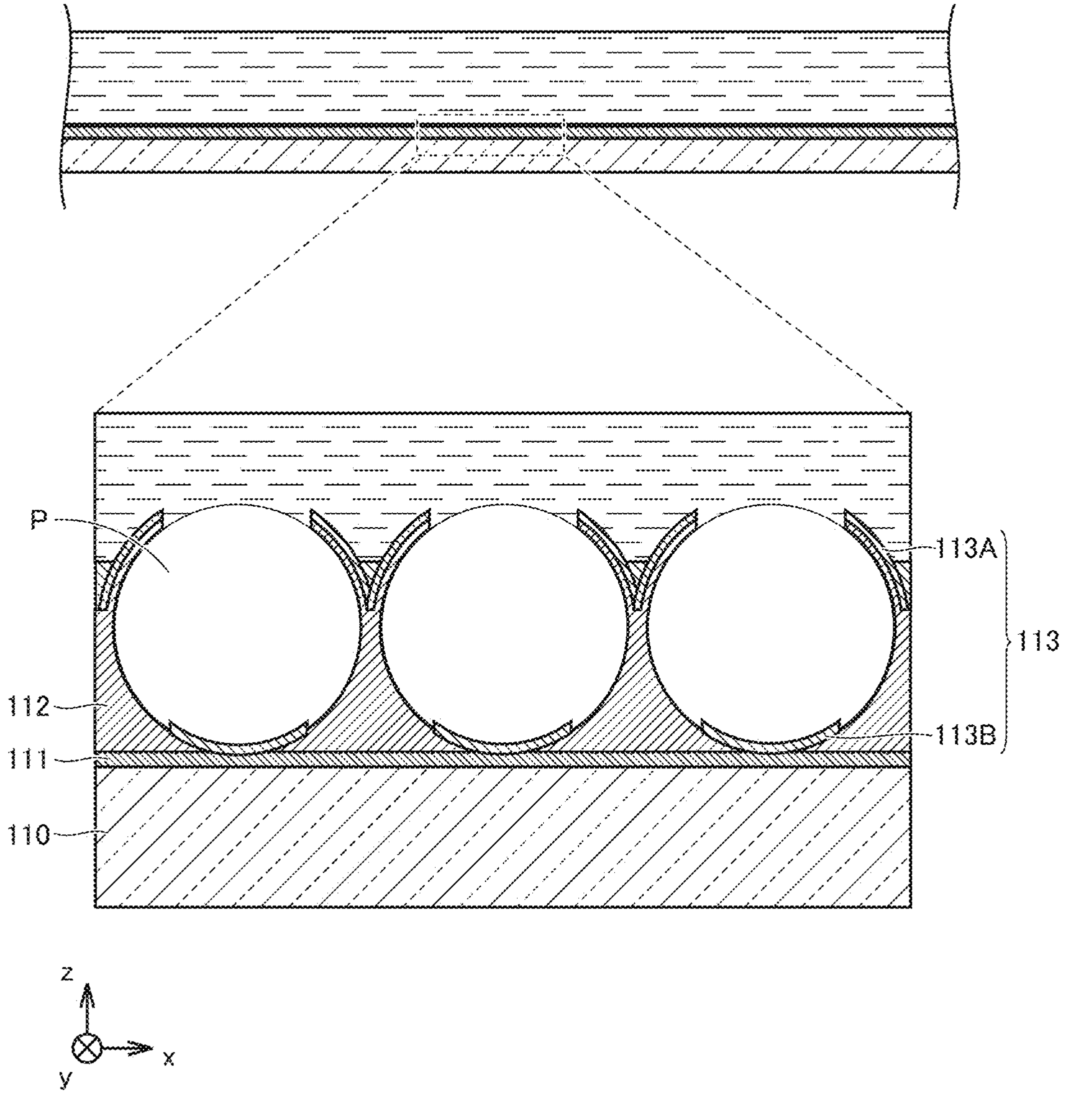
FIG. 5 is an enlarged view of a bottom portion.

Bottom portion 11 is disposed under the sample to hold the sample. The detailed configuration of bottom portion 11 is illustrated in FIG. 5.

Top portion 12 covers the sample from above while the sample is held on a substrate 110. Transparent materials (such as glass, quartz, and silicone) that allow the passage of a laser beam and white light can be used as materials of top portion 12. In the example of FIG. 2, a cover glass is used for top portion 12.

Side portions 13 extend from bottom portion 11 in the vertical direction (z direction) and are disposed between bottom portion 11 and top portion 12. Side portions 13 are provided to fix top portion 12 with respect to bottom portion 11 and keep a distance between bottom portion 11 and top portion 12 at a set value. In this example, a double-sided tape is used for side portions 13. Other materials (such as resin, rubber, glass, quartz, and silicone) may be used.

Top portion 12 is provided to hold the sample between bottom portion 11 and top portion 12, so that microbubbles (described later) can be stably generated and the noise of the reflection spectrum can be reduced. However, the placement of top portion 12 may be omitted. In this case, side portions 13 are also allowed to be omitted.

FIG. 5 is an enlarged view of bottom portion 11. Bottom portion 11 includes substrate 110, metallic thin film 211, a conductive polymer film 112, and metallic thin film 113.

Substrate 110 provides mechanical strength that allows detection kit 10 to hold the sample. As a material of substrate 110, materials (such as glass, quartz, and silicone) that can fix metallic thin film 211 are usable. In this example, a glass portion at the center of a glass bottom dish is used as substrate 110.

Metallic thin film 211 is a thin film that is made only of a metal and is disposed on substrate 110. Metallic thin film 211 has a thickness (film thickness) on the nanometer order, for example, about several tens of nanometers. As a material of metallic thin film 211, a material that produces surface plasmon resonance by a laser beam (near infrared light in the present embodiment) from laser light source 3 is used. In Embodiment 1, a thin gold film is formed as metallic thin film 211.

If metallic thin film 211 is a thin gold film, free electrons on a surface of the thin gold film form surface plasmon and are vibrated by a laser beam. This exhibits polarization. The energy of polarization is converted to the energy of lattice vibrations by Coulomb interaction between free electrons and an atomic nucleus. Consequently, the thin gold film generates heat. Hereinafter, this effect may be referred to as “photothermal effect.” Metallic thin film 211 corresponds to “first thin film” according to the present disclosure.

Conductive polymer film 112 is a film that is made only of a conductive polymer and is disposed on metallic thin film 211. Like metallic thin film 211, conductive polymer film 112 has a thickness on the nanometer order, for example, about several tens of nanometers to several hundred nanometers. As a material of conductive polymer film 112, various known materials such as polythiophene, polyacethylene, polyaniline, and polypyrrole can be used. In this example, polypyrrole is adopted. Conductive polymer film 112 corresponds to “structure” according to the present disclosure.

Metallic thin film 113 is a thin film that is made of a metal and is disposed on conductive polymer film 112. Metallic thin film 113 also has a thickness on the nanometer order, for example, about several tens of nanometers. Also as a material of metallic thin film 113, a material (gold in the present embodiment) that may produce a photothermal effect by a laser beam from laser light source 3 is used. Metallic thin film 113 corresponds to “second thin film” according to the present disclosure.

A plurality of non-penetrating pores P are periodically (regularly) disposed at bottom portion 11. The size of non-penetrating pore P ranges from the nanometer order to the micrometer order. More specifically, conductive polymer film 112 has a plurality of recesses. The inner walls of the plurality of recesses each form a “bowl-like structure” that is a recess of spherical segment shape. In the example of FIG. 5, the diameter of the bowl-like structure monotonously increases from the bottom portion located immediately above metallic thin film 211 to the central portion (diameter portion) of a sphere and monotonously decreases from the central portion to the opening. However, the diameter of the bowl-like structure may monotonously increase from the bottom portion to the opening (see FIG. 6(C) described later).

Metallic thin film 113 is disposed outside (outside the upper portion of) the bowl-like structure and is disposed inside (around the bottom surface of) the bowl-like structure. For the sake of clarity, the metallic thin film disposed outside the bowl-like structure is denoted by reference numeral 113A, and the metallic thin film disposed inside the bowl-like structure is denoted by reference numeral 113B. Metallic thin film 113A is shaped like shampoo hats having a plurality of openings. Metallic thin films 113A and 113B correspond to "third thin film" and "fourth thin film", respectively, according to the present disclosure.

FIG. 5 illustrates recesses of spherical segment shape. The shape of the recess is not limited thereto. The recess may be shaped like a rod (e.g., a cylinder or a prism) or a cone (e.g., a circular cone or a pyramid). Furthermore, the shape of the recess may be a combination of a spherical segment shape, a rod shape, and a cone shape. For example, the recess may be spherical segment or conical with a diameter increasing from the bottom portion toward the upper side and may be cylindrical around the opening with a constant diameter.

The material of metallic thin films 211 and 113 is not limited to gold and may be a metallic element (e.g., silver or platinum) capable of producing a photothermal effect other than gold or a metallic nanoparticle accumulated structure (e.g., a structure with a gold nanoparticle or a silver nanoparticle). Alternatively, the material of metallic thin films 211 and 113 may be a material other than a metal and having high light absorption in the wavelength range of a laser beam. Such a material may be a material close to a black body (e.g., a carbon nanotube black body). The material (first material) of metallic thin film 211 and the material (second material) of metallic thin film 113 may be different from each other.

<Fabrication of Detection Kit>

Figure 6:
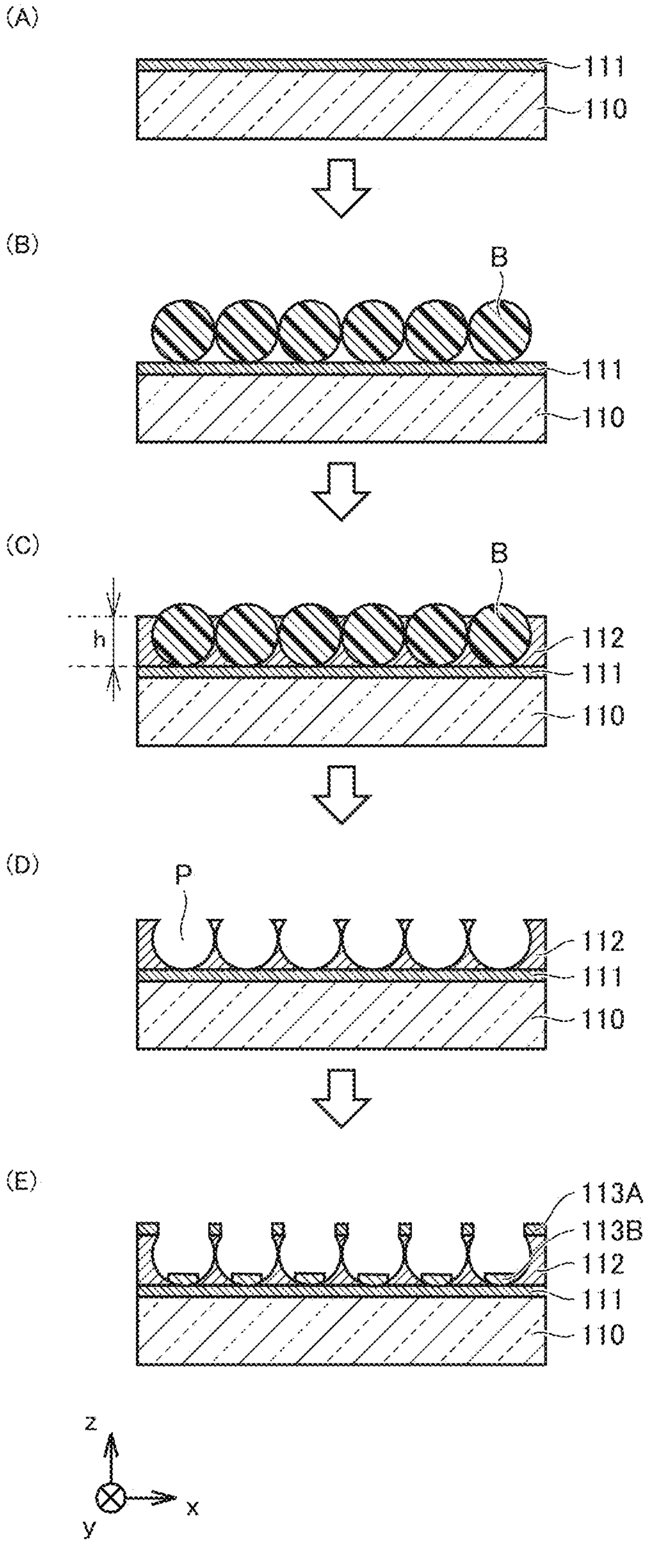
FIG. 6 is a schematic process drawing of a method for fabricating the detection kit according to Embodiment 1.

FIG. 6 is a schematic process drawing of a method for fabricating detection kit 10 according to Embodiment 1. Referring to FIG. 6(A), first, metallic thin film 111 is formed on substrate 110. More specifically, substrate 110 is cleaned by using, for example, an ultrasonic cleaner (not illustrated). Thereafter, metallic thin film 111 is formed on substrate 110 by, for example, ion sputtering. As a method for forming metallic thin film 111, other thin-film forming methods such as vacuum deposition and electroless plating may be used.

Subsequently, a dispersion liquid containing dispersed resin beads (denoted as B in FIG. 6(B)) is dropped onto metallic thin film 211. The material of the resin beads is, for example, polystyrene, acryl, polyolefin, polyethylene, or polypropylene. The particle size of the resin beads ranges from the nanometer order to the micrometer order. In the present embodiment, polystyrene beads with a particle size of 1.0 μm or 500 nm were used.

Thereafter, the dispersion liquid dropped onto metallic thin film 211 is air-dried at room temperature for a predetermined time (e.g., 24 hours). Thus, the resin beads are periodically arranged like a single layer on metallic thin film 211 by self-organization. At the completion of drying of the dispersion liquid, a single-layer film of the resin beads is formed in the range of several millimeters to ten-odd millimeters in the horizontal direction (the principal surface direction of metallic thin film 211).

As illustrated in FIG. 6(C), conductive polymer film 112 is then formed so as to fill the gaps of the single-layer film of the resin beads and expose a part of the surface of each resin bead. In this example, conductive polymer film 112 is a polypyrrole film. The polypyrrole film can be formed by using, for example, electrolytic polymerization. By properly setting an electrolytic polymerization time, a height h of conductive polymer film 112 (that is, the height of the bowl-like structure) can be set at a desired value.

After conductive polymer film 112 is generated, the resin beads are removed (see FIG. 6(D)). The resin beads can be removed by selectively melting the resin beads with a solvent in which the material of the resin beads is more soluble than the material of conductive polymer film 112. If conductive polymer film 112 is a polypyrrole film and the resin beads are polystyrene beads, the resin beads can be removed by immersing detection kit 10 in a chloroform solution for a required time (e.g., one minute). At the completion of the removal of the resin beads, bowl-like structures molded by the resin beads are formed in conductive polymer film 112.

Moreover, a nano-bowl structure molded using resin beads arranged by self-organization is formed as an example. "A plurality of non-penetrating pores" according to the present disclosure may be formed by lithography.

Finally, metallic thin film 113 is further formed on conductive polymer film 112 (see FIG. 6(E)). Like metallic thin film 211, metallic thin film 113 can be formed by ion sputtering. Metallic thin film 113 may be formed by using vacuum deposition or electroless plating. Metallic thin film 113 desirably has a small thickness (e.g., about several tens of nm).

In the example of detection kit 10 shown in FIG. 2, first, metallic thin film 211 (thin gold film) is formed by ion sputtering in a glass portion (corresponding to the substrate 110) located at the bottom surface of the glass bottom dish. Subsequently, conductive polymer film 112 (polypyrrole film) is formed on metallic thin film 211 by electrolytic polymerization. Thereafter, the glass portion is removed from the glass bottom dish, and then metallic thin film 113 (thin gold film) is further formed on conductive polymer film 112 by ion sputtering. The glass portion is then placed on a slide glass.

If polystyrene beads with a particle size of 1.0 μm are used, a bowl-like structure having a diameter of about 1.0 μm is formed. If polystyrene beads with a particle size of 500 nm are used, a bowl-like structure having a diameter of about 500 nm is formed. Hereinafter, a detection kit in which bowl-like structures having a diameter of about 1.0 μm are periodically arranged will be referred to as "micro-bowl substrate." A detection kit in which bowl-like structures having a diameter of about 500 nm are periodically arranged will be referred to as "nano-bowl substrate." Moreover, a region in which the bowl-like structures are periodically arranged at the bottom portion 11 will be also referred to as "bowl region." The bowl region corresponds to "photothermal conversion region" according to the present disclosure. The diameter of the bowl-like structure will be also referred to as "bowl diameter φ."

Figure 7:
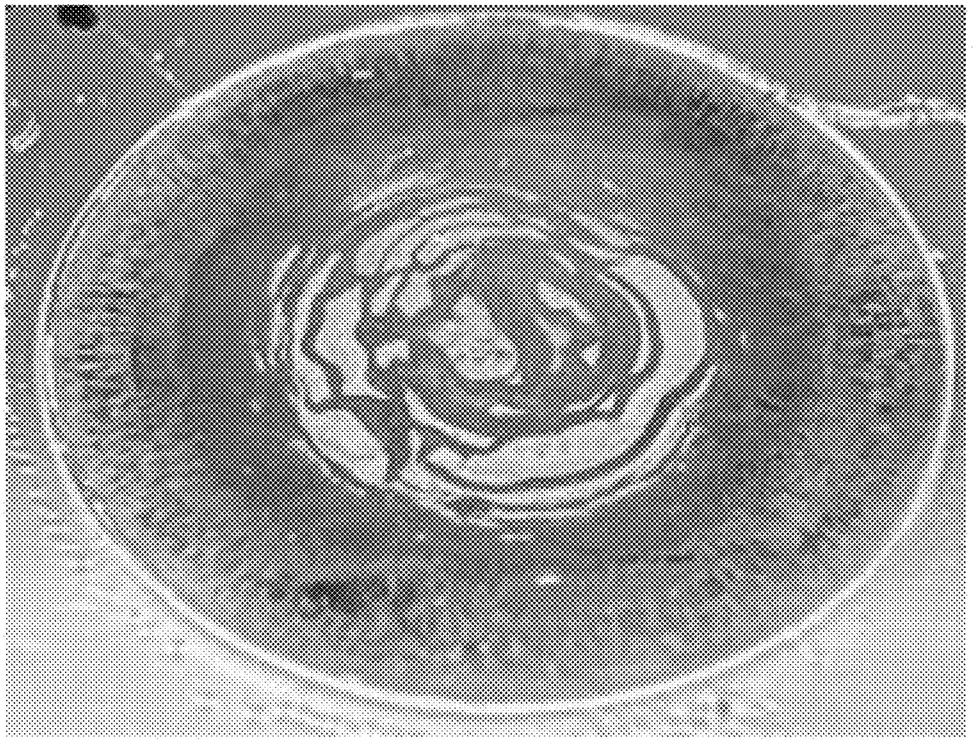
FIG. 7 is a diagram illustrating an image of a bowl region on a nano-bowl substrate.

FIG. 7 is a diagram illustrating an image of a bowl region on a nano-bowl substrate. The bowl region expresses a structural color. This proves that the bowl region has a fine periodic structure.

Figure 8:
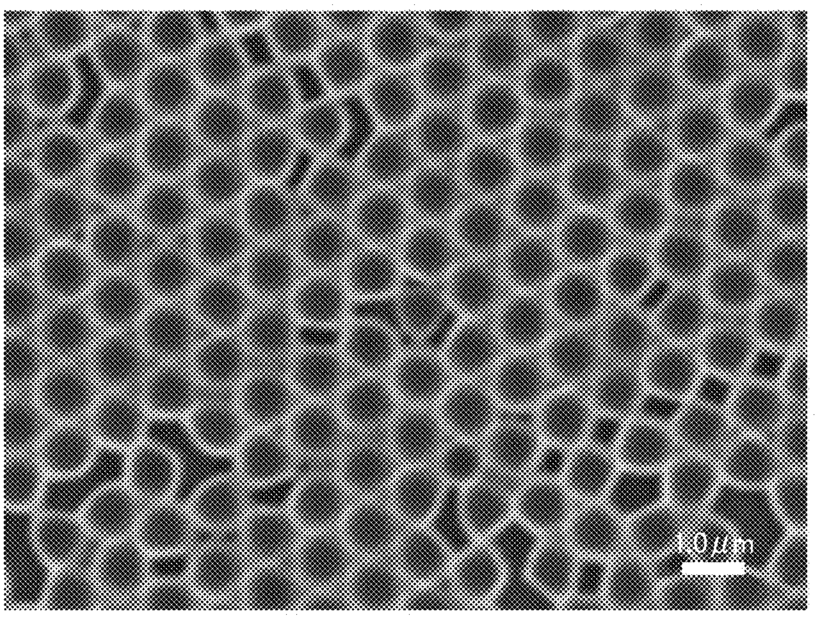
FIG. 8 is a diagram illustrating an SEM image of a micro-bowl substrate.
Figure 9:
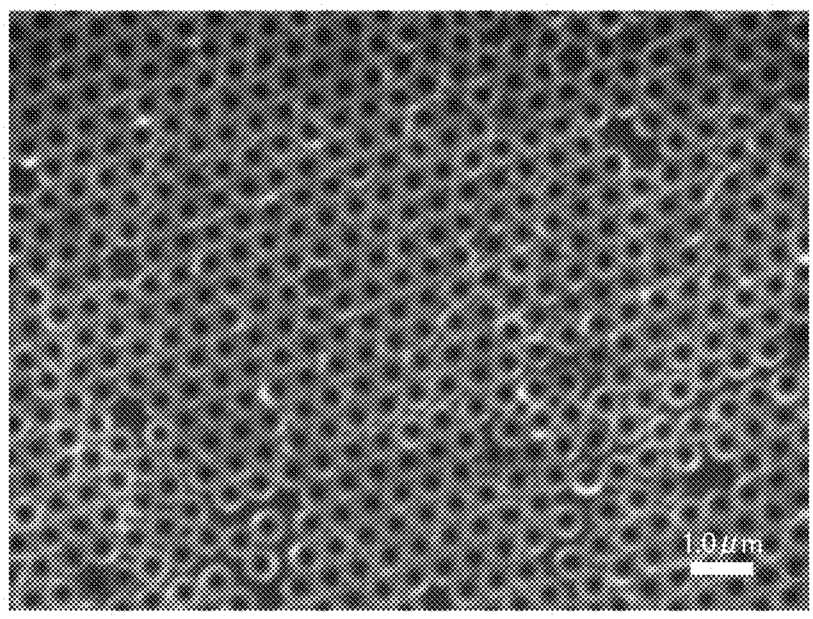
FIG. 9 is a diagram illustrating an SEM image of the nano-bowl substrate.

FIG. 8 is a diagram illustrating an SEM (Scanning Electron Microscope) image of a micro-bowl substrate. FIG. 9 is a diagram illustrating an SEM image of a nano-bowl substrate. As shown in FIGS. 8 and 9, it is confirmed that bowl-like structures are arranged in a honeycomb pattern in a bowl region. However, the arrangement of the bowl-like structures in a honeycomb pattern is an example of a periodic array. "A plurality of non-penetrating pores" according to the present disclosure are preferably disposed like a two-dimensional lattice. For example, the non-penetrating pores may be disposed like a tetragonal lattice, a rectangular lattice, an orthorhombic lattice, or a face-centered rectangular lattice. For example, if a lithography technique is used, "a plurality of non-penetrating pores" according to the present disclosure may be typically disposed like a tetragonal lattice or a rectangular lattice (so-called matrix).

<Accumulation Mechanism>

Figure 10:
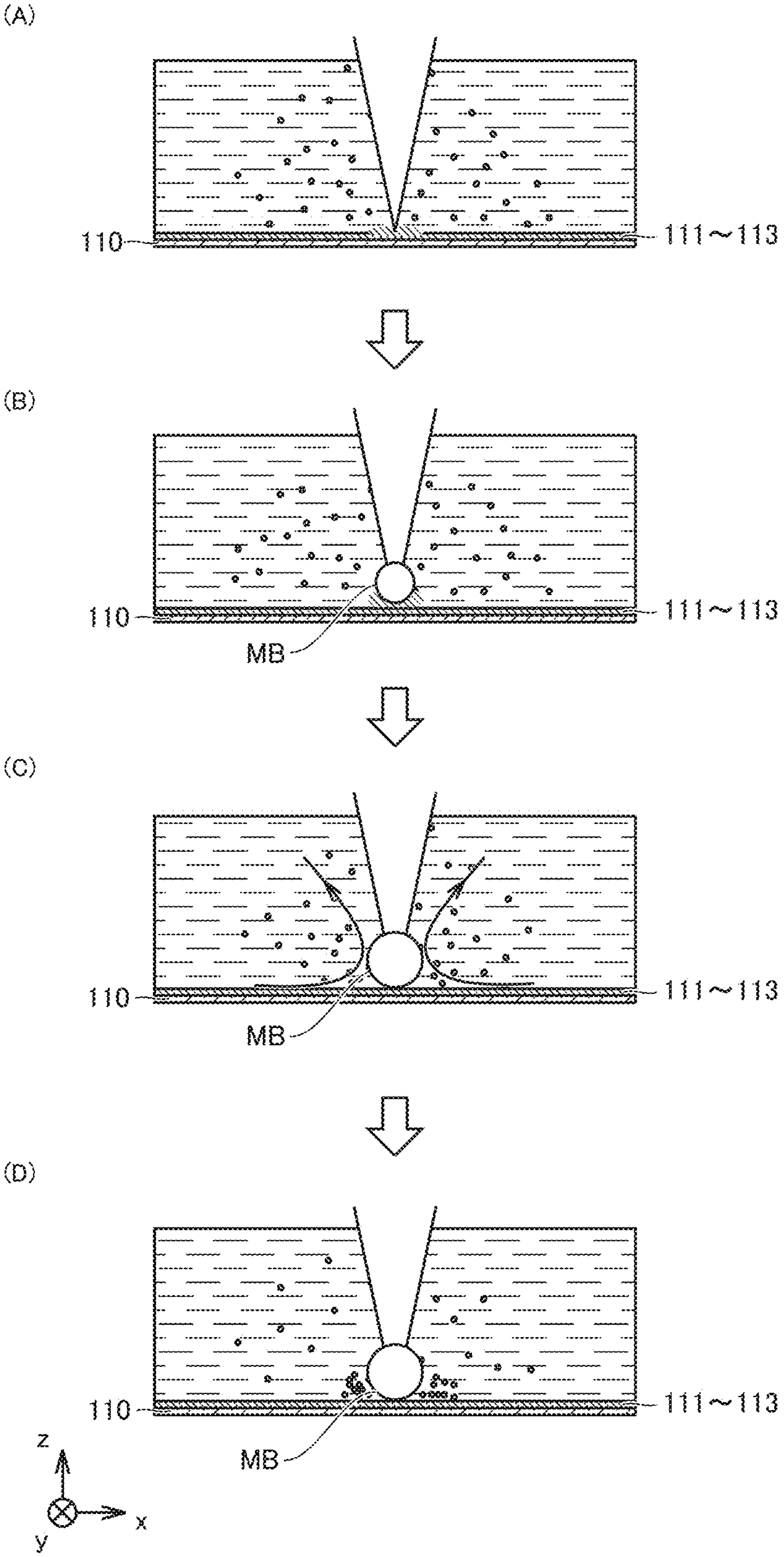
FIG. 10 is a diagram for explaining an accumulation mechanism of microscopic objects.

FIG. 10 is a diagram for explaining an accumulation mechanism of microscopic objects. Upon the start of the irradiation of a bowl region with a laser beam, by the photothermal effect of metallic thin film 113 in the irradiation region of the laser beam (hereinafter also referred to as "laser spot"), the vicinity of the laser spot is locally heated (see (A)). Thus, a microbubble (denoted as MB) is generated at the laser spot by boiling the dispersion medium (in this example, water) of a sample near the laser spot (see (B)). The microbubble grows with the passage of time.

With the irradiation with the laser beam, regular thermal convection routinely occurs in the dispersion medium in addition to the microbubble. As indicated by arrows in (C), the direction of the thermal convection is temporarily directed to the microbubble and then is directed away from the microbubble. The reason for the occurrence of the thermal convection will be described below. Thermal convention is classified into buoyancy convection and Marangoni convection.

The closer to the laser spot, the higher the temperature of the dispersion medium. In other words, a temperature gradient occurs due to photoirradiation in the dispersion medium. The temperature gradient causes buoyancy convection. More specifically, the dispersion medium becomes relatively dilute by heating above a region in which the microbubble is generated, and then the dispersion medium is floated by a buoyant force. Meanwhile, a dispersion medium having a relatively low temperature in the horizontal direction of the microbubble flows into the microbubble.

Generally, an interfacial tension generated on the surface of a bubble depends upon a molecular density on the surface of the bubble. The higher the molecular density, the smaller the interfacial tension. A molecular density in the present embodiment is affected by the density of microscopic objects in addition to the density of molecules constituting the dispersion medium. Thus, in the presence of a density gradient of microscopic objects on the gas-liquid interface between the microbubble and the dispersion medium, a region containing microscopic objects with a high density (typically, a lower region) is drawn toward a region containing microscopic objects with a low density (an upper region) such that the interfacial tension is balanced between the regions. At this point, the movement of the gas-liquid interface is transmitted into a liquid (bulk) and generates Marangoni convection. Marangoni convection is dependent upon a density gradient but is independent of gravity.

Microscopic objects are conveyed to microbubbles by thermal convection (buoyancy convection and/or Marangoni convection) and are trapped by the microbubbles. More specifically, "stagnation region" in which the flow velocity of thermal convection is substantially 0 is generated between the microbubbles and the bowl region. The microscopic objects conveyed by thermal convection are trapped into the stagnation region, so that the microscopic objects are accumulated near the laser spot (see (D)). In this way, microbubbles act as "stopper" for blocking microscopic objects and thus serve as an accumulation site of the microscopic objects. The effect of concentrating and accumulating microscopic objects, which are dispersed in a sample, near a laser spot according to this mechanism can be also referred to as "light concentration."

<Detection Flow>

In Embodiment 1, in addition to the accumulation of microscopic objects at a laser spot, the concentration of microscopic objects contained in a sample can be calculated on the basis of the amount of microscopic objects accumulated at the laser spot.

Figure 11:
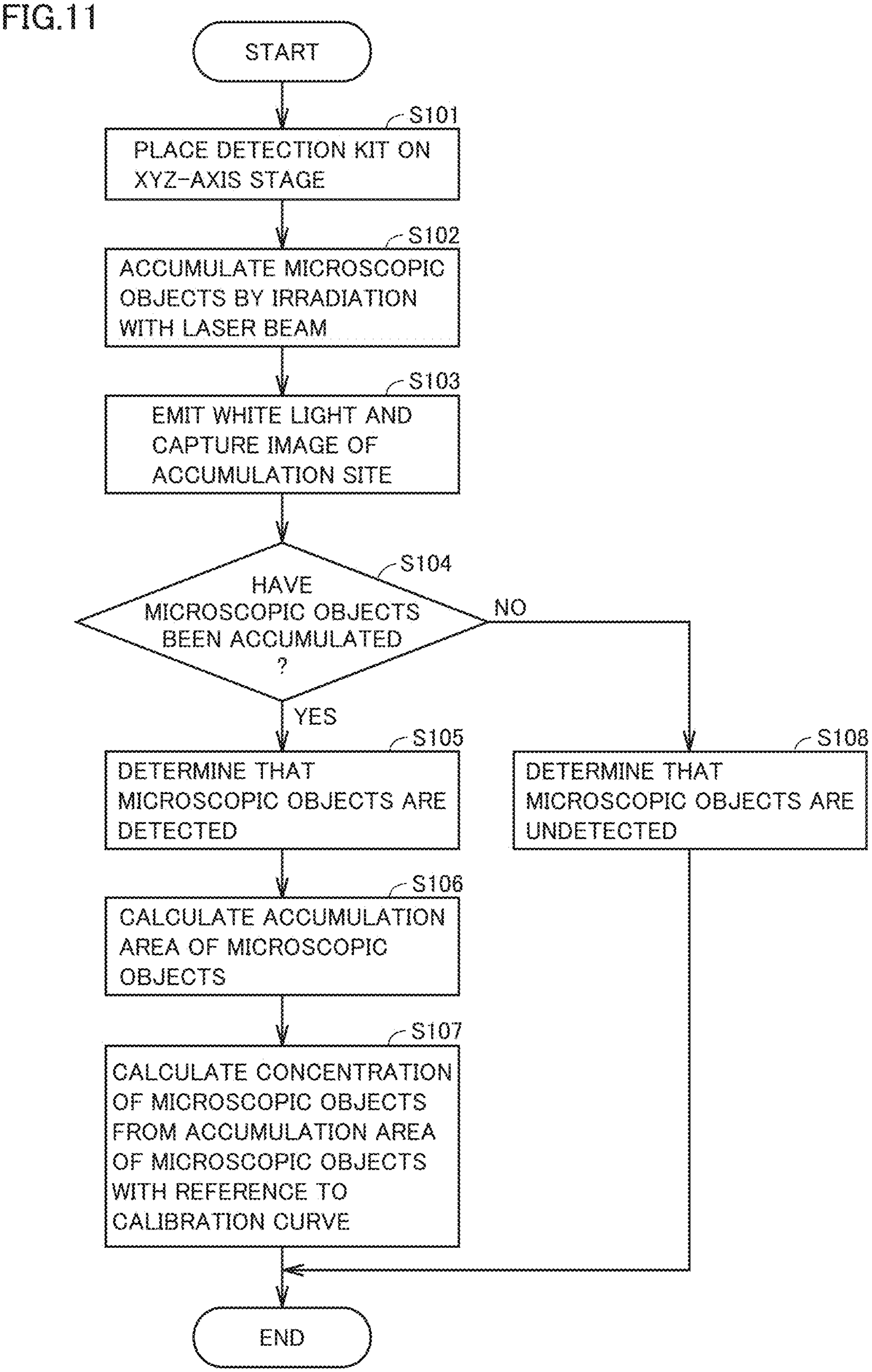
FIG. 11 is a flowchart indicating the steps of a method for detecting microscopic objects according to Embodiment 1.

FIG. 11 is a flowchart indicating the steps of a method for detecting microscopic objects according to Embodiment 1. The flowchart is called from a main routine, which is not illustrated, and is executed when predetermined conditions are established (for example, when receiving an operation by a measurer). The steps are basically implemented by software processing performed by controller 9. The steps may be implemented by hardware (electric circuit) disposed in controller 9. Hereinafter, the steps will be abbreviated as S.

In S101, the detection kit 10 with a sample prepared on the bowl region is placed on xyz-axis stage 1. This processing may be manually performed by the measurer or may be automated by providing a mechanism (not illustrated) for feeding detection kit 10. Moreover, the sample can be dropped onto the bowl region by using a dispenser or the like.

In S102, controller 9 controls laser light source 3 so as to output a laser beam with predetermined power for a predetermined time. The power of the laser beam (laser output power) and the irradiation time of the laser beam (laser irradiation time) are set at values corresponding to the specifications of detection kit 10 (the materials and thicknesses of metallic thin films 211 and 113 or the like) and the characteristics of microscopic objects (an assumed concentration, the size or the like) on the basis of the results of previously conducted experiments or simulations. By the irradiation with the laser beam, the microscopic objects are accumulated at the laser spot according to the accumulation mechanism illustrated in FIG. 10.

In S103, the controller 9 controls imaging device 6 so as to capture an image (e.g., a static image) of the bowl region as an accumulation site while controlling illumination light source 4 so as to emit white light. If a moving image is captured, controller 9 may control illumination light source 4 so as to start irradiation with white light before starting irradiation with a laser beam. Controller 9 may cause illumination light source 4 to stop the irradiation with white light after the completion of imaging of the bowl region.

In step S104, controller 9 determines whether an aggregate of microscopic objects is observed in the image captured by imaging device 6. If an aggregate of microscopic objects is not observed (NO at S104), controller 9 determines that the sample does not contain microscopic objects (the concentration of microscopic objects in the sample is lower than the detection limit) (S108).

If an aggregate of microscopic objects is observed (YES at S104), controller 9 determines that the sample contains microscopic objects (S105). In this case, controller 9 calculates the area (accumulation area) of a region where the microscopic objects are accumulated (S106). Controller 9 can calculate the area of the region where the microscopic objects are accumulated, by extracting the region according to an image processing technique for pattern recognition. Furthermore, referring to a predetermined calibration curve (described later), controller 9 calculates the concentration of microscopic objects contained in the sample, from the accumulation area calculated in S106 (S107). At the completion of the processing of S107 or S108, controller 9 returns the processing to the main routine.

<Generation of Microbubbles>

In order to promote the practical use of detection system 100 and the detection method for microscopic objects described above, it is desirable that microscopic objects can be accumulated with high efficiency. As a result of diligent examination, the present inventors found that ease of generation of microbubbles depends upon the size of the bowl-like structure. By using the knowledge, microscopic objects can be accumulated with high efficiency.

Figure 12:
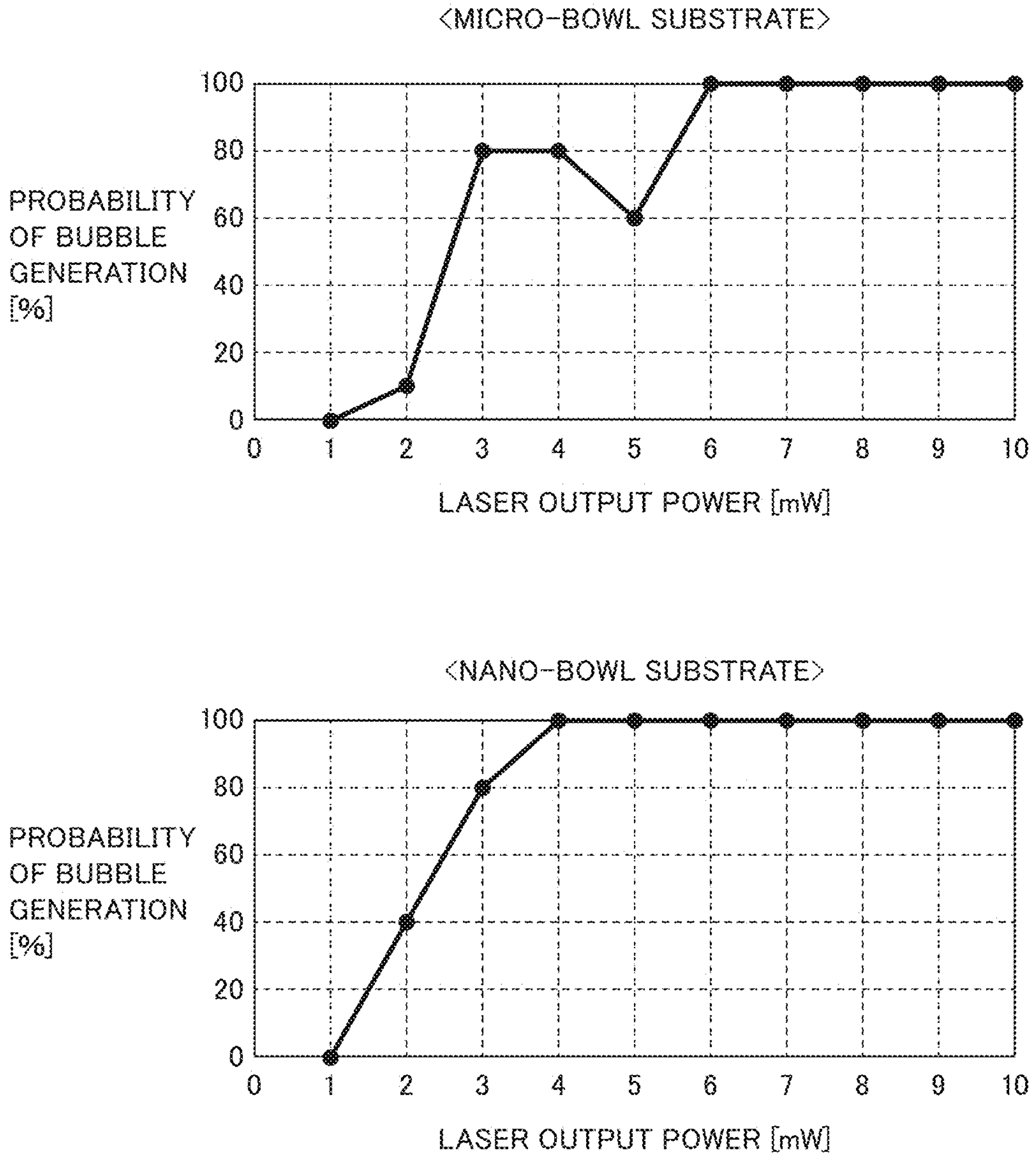
FIG. 12 is a diagram illustrating an example of an examination result on ease of generation of microbubbles.

FIG. 12 is a diagram illustrating an example of the examination result on ease of generation of microbubbles. The horizontal axis indicates laser output power (the power of a laser beam having passed through objective lens 5). The vertical axis indicates the probability of generation of microbubbles. The wavelength of a laser beam was 1064 nm. The laser irradiation time was 5 seconds. The laser output power was changed by 1 mW between 1 mW and 10 mW. For each laser output, ten measurements were conducted. The probability of occurrence of microbubbles was calculated from the number of times of generation of microbubbles.

In both of a micro-bowl substrate and a nano-bowl substrate, microbubbles were generated with a probability of about 80% or more by setting the laser output power at 3 mW or more. In the range of 2 to 5 mW of laser output power, in particular, the nano-bowl substrate has a higher probability of generation of microbubbles than the micro-bowl substrate. When the laser output power is increased, microbubbles can be securely generated to accumulate microscopic objects but the accumulated microscopic objects may be thermally damaged. Moreover, a laser light source with high laser output power tends to be large-sized. In the nano-bowl substrate, microbubbles can be generated to accumulate microscopic objects with low laser output power. Thus, thermal damage to microscopic objects can be reduced and laser light source 3 can be downsized.

Under the conditions of equal laser output power, the probability of generation of microbubbles is higher in the use of the nano-bowl substrate than in the use of the micro-bowl substrate. The reason will be described below.

Figure 13:
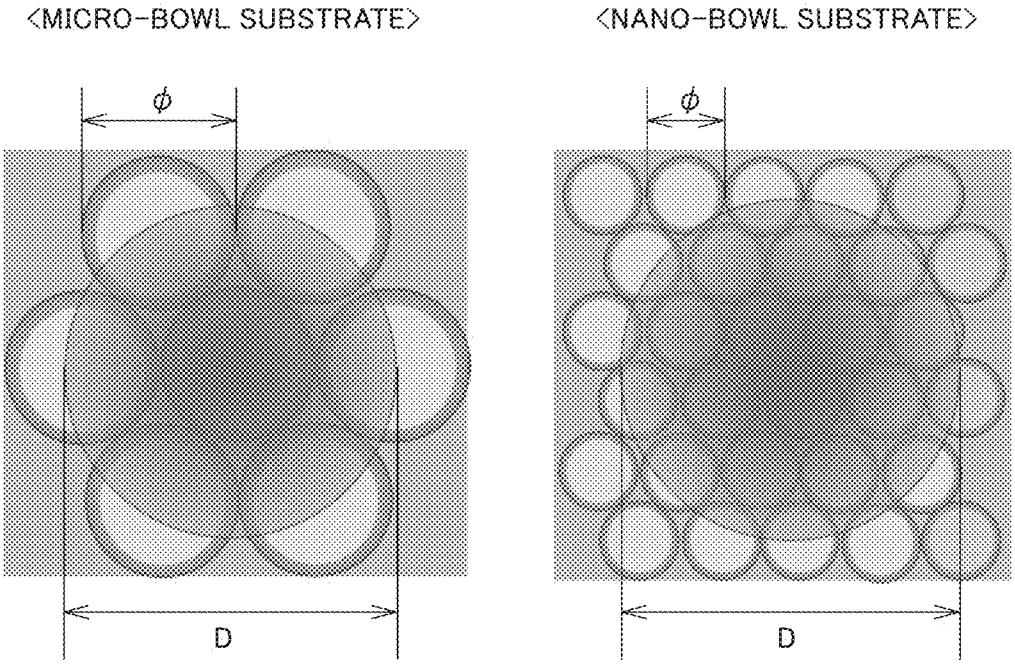
FIG. 13 is a diagram for explaining the relationship between the size of a bowl-like structure and the size of a laser spot.

FIG. 13 is a diagram for explaining the relationship between the size of the bowl-like structure and the size of a laser spot. In the present embodiment, a diameter D of a laser spot (spot diameter) is quite small as large as a bowl diameter φ(=500 nm, 1.0 μm). For example, the spot diameter D was 2.16 μm. In the example of FIG. 13, for simplicity, it is assumed that the laser spot is a perfect circle. The laser spot may have a shape (for example, an ellipse) other than a perfect circle.

In the micro-bowl substrate, a laser spot includes only a small number of bowl-like structures. Specifically, a bowl-like structure at the center of a laser beam is entirely included in a laser spot, whereas six bowl-like structures around the central bowl-like structure are just partially included in the laser spot. In other words, in a top view of the bowl region of the micro-bowl substrate, only a single bowl-like structure is entirely included in the laser spot.

In contrast, in the nano-bowl substrate, at least two bowl-like structures are entirely included in a laser spot. Furthermore, in the case of a bowl diameter φ=500 nm for a spot diameter D=2.16 μm, at least six bowl-like structures around the central bowl-like structure are included in the laser spot in addition to the bowl-like structure at the center of the laser beam. In other words, six bowl-like structures at the positions of at least the lattice points of a honeycomb lattice are entirely included in the laser spot. Thus, in the nano-bowl substrate, seven or more bowl-like structures are entirely included in the laser spot.

A description from another aspect will be made according to a mathematical expression. N, the number of bowl-like structures included in a laser spot, is calculated using a spot diameter D and a bowl diameter φ according to expression (1) below. If only a half of the bowl-like structure is included in a laser spot, N is calculated as 0.5. N is a value to which a decimal point or less corresponding to a ratio of inclusion in a laser spot is added.

[Expression 1]

$$N = \frac{\pi}{\sqrt{12}}\left(\frac{D}{\varphi}\right)^2 \quad (1)$$

In the micro-bowl substrate, a spot diameter D=2.16 μm and a bowl diameter φ=1.0 μm are substituted, so that N=4.2 is obtained. In the nano-bowl substrate, a spot diameter D=2.16 μm and a bowl diameter φ=500 nm are substituted, so that N=16.9 is obtained. In other words, in the nano-bowl substrate, the number of bowl-like structures included in a laser spot is four times or more than that in the micro-bowl substrate.

It is assumed that the bowl-like structure of the micro-bowl substrate and the bowl-like structure of the nano-bowl substrate are similar in shape. Thus, the volume ratio of the volume of each bowl-like structure in the micro-bowl substrate and the volume of each bowl-like structure in the nano-bowl substrate is 8:1. The total volume ratio of bowl-like structures in a laser spot is calculated as 2:1 by multiplying the volume ratio of each bowl-like structure (8:1) and the ratio of the numbers of bowl-like structures in a laser spot (4.2:16.9). In other words, the volume of a portion heated by irradiation of the nano-bowl substrate with a laser beam is about half of the volume of a portion heated by irradiation of the micro-bowl substrate with a laser beam.

If the nano-bowl substrate and the micro-bowl substrate having metallic thin film 113 of the same thickness are irradiated with a laser beam of the same power, an equal quantity of heat is applied to the substrates. In the nano-bowl substrate, the volume of a heated portion is about half of that on the micro-bowl substrate, though an equal quantity of heat is applied to the substrates. This achieves light heating with high efficiency in the bowl-like structure. Hence, it is understood that microbubbles are more likely to be generated in the nano-bowl substrate than in the micro-bowl substrate.

The reason why a microbubble is more likely to be generated in the nano-bowl substrate than in the micro-bowl substrate will be more specifically described below in consideration of a mechanism for generating a microbubble. The mechanism for generating a microbubble is conceived of as follows: As illustrated in FIG. 5, metallic thin film 113A is disposed outside (outside the upper portion of) the bowl-like structure, and metallic thin film 113B is disposed inside the bowl-like structure. In the bowl-like structure before the start of irradiation with a laser beam, air is left in addition to water serving as a dispersion medium. Upon the start of irradiation with the laser beam, residual air expands due to the photothermal effect of metallic thin film 113B in the bowl-like structure. Thus, residual air flowing out of the bowl-like structure generates microbubble cores in the dispersion medium. When the irradiation with the laser beam is continued, the dispersion medium is heated and boiled by the photothermal effect of metallic thin film 113A outside the bowl-like structure and/or metallic thin film 113B in the bowl-like structure, so that water vapor is generated. The water vapor generated near the microbubble cores adheres to the microbubble cores, so that the microbubble grows.

Microbubbles are more likely to be generated in the nano-bowl substrate for three reasons. The first reason is based on the following thermodynamic examination. It is assumed that residual air in the bowl-like structure is ideal gas. The internal pressure of the residual air is denoted as p. The volume of the residual air (=the volume of the bowl-like structure) is denoted as V. The number of moles of gas molecules constituting the residual air is denoted as n. The temperature of the residual air is denoted as T. The internal energy of the residual air is denoted as U. The quantity of heat applied to the residual air is denoted as dQ, the heat being applied from metallic thin film 113 subjected to light heating by irradiation with a laser beam.

In consideration of an energy conservation law only for residual air regardless of the evaporation of a dispersion medium, a state equation before light heating is $pV=nRT \propto U$ (R is a gas constant). Thus, in the case of a constant pressure process, volume V of the residual air is proportionate to internal energy U. At the beginning of expansion of residual air, since a volume change $dV \neq 0$, $dW=-pdV \neq 0$ is obtained from the first law of thermodynamics $dU=dW+dQ$. Thus, a change of internal energy U of the residual air is $dU \neq dQ$. If metallic thin film 113 in a laser spot has an equal area and an initial temperature T and a change dQ of the amount of heat are equal, the smaller volume V of the bowl-like structure, the smaller number n of molecules contained in the residual air, so that a quantity of heat dQ/n applied to each molecule is large. This means that as compared with the micro-bowl substrate, a heat quantity change dQ/V per unit volume is larger in the nano-bowl substrate where the bowl-like structure has a small volume V. dQ/V is proportionate to internal pressure p according to the state equation. Hence, internal pressure p of the residual air is likely to increase due to the irradiation with a laser beam in the nano-bowl substrate than in the micro-bowl substrate. When internal pressure p increases, the residual air expands and easily moves out of the bowl-like structure. Hence, it is understood that the microbubble cores are likely to be generated in the nano-bowl substrate.

The small bowl-like structures of the nano-bowl substrate contribute to an improvement in the repellency of the nano-bowl substrate. Thus, residual air may be easily held in the bowl-like structure before light heating (in other words, residual air is hardly removed from the bowl-like structure without light heating).

The second reason is that multiple cores may be generated in the nano-bowl substrate because of a large number of nano-bowl structures included in a laser spot. The third reason is that water vapor is more likely to adhere to the cores in the nano-bowl substrate the shorter the distance between metallic thin film 113A and metallic thin film 113B is.

Example of Embodiment 1

The results of accumulation of various microscopic objects will be described below. In these examples, a system configuration was adopted as will be described below. A fluorescent image was captured instead of capturing an image under irradiation with white light (optical microscope image).

Figure 14:
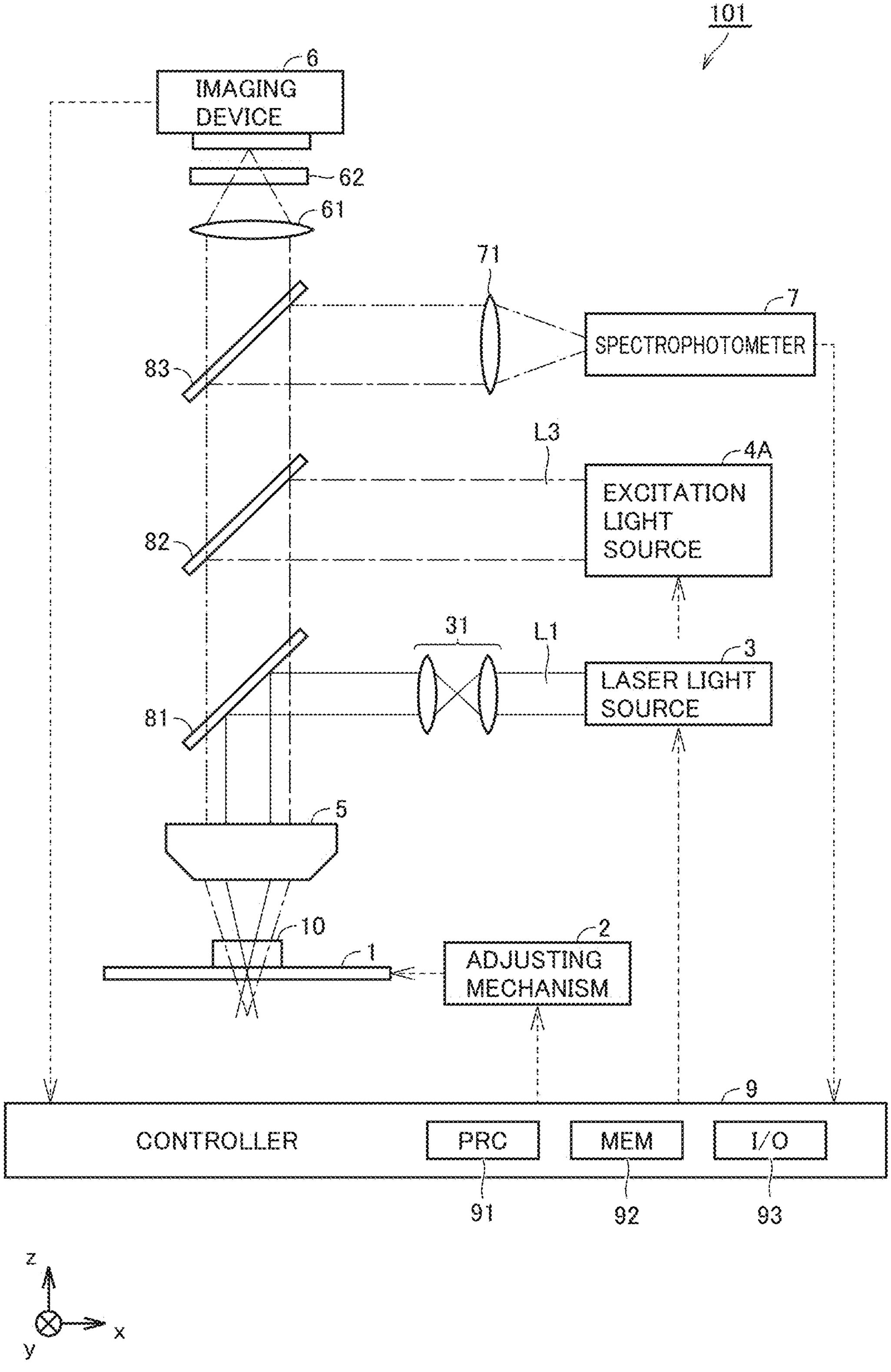
FIG. 14 is a diagram illustrating another example of the overall configuration of the detection system of microscopic objects according to Embodiment 1.

FIG. 14 is a diagram illustrating another example of the overall configuration of the detection system of microscopic objects according to Embodiment 1. A detection system 101 is different from detection system 100 (see FIG. 1) according to Embodiment 1 in that an excitation light source 4A is provided instead of illumination light source 4 and a fluorescence filter 62 is further provided.

Excitation light source 4A emits excitation light (indicated by L3) for exciting fluorescent dyes contained in a sample on detection kit 10, according to a command from controller 9. Excitation light source 4A may be a light source (e.g., an LED (Light Emitting Diode)) for emitting monochromatic light or a light source (e.g., a mercury lamp) for emitting light of a wide band with a spectroscope. Excitation light source 4A may include an optical system for converting excitation light into parallel beams.

Fluorescence filter 62 is disposed in the previous stage of imaging device 6. Fluorescence filter 62 passes light in the wavelength range of fluorescence emitted from the fluorescent dyes contained in the sample; meanwhile, fluorescence filter 62 blocks light outside the wavelength range. Other components of detection system 101 are basically equivalent to the corresponding components of detection system 100 and thus a detailed description thereof is not repeated.

<Accumulation of Polystyrene Beads>

First, an example of the calculation of the concentration of polystyrene beads in a sample from the accumulation area of the accumulated polystyrene beads will be described below, the polystyrene beads being accumulated by using the nano-bowl substrate. In this example, polystyrene beads subjected to fluorescent dyeing (fluorescent beads) were used. The polystyrene beads were 100 nm in diameter. The size is as large as the size of a virus. For example, the diameter of the novel coronavirus (SARS-COV-2) is about 50 nm to 200 nm.

Three samples of polystyrene beads with different initial concentrations (concentrations before accumulation) were prepared. The initial concentrations of the polystyrene beads in the samples were $4.55 \times 10^{10}$ [particles/mL], $4.55 \times 10^{9}$ [particles/mL], and $4.55 \times 10^{8}$ [particles/mL]. The volumes of the samples were 20 μL. The wavelength of a laser beam was 1064 nm. The laser output power was 10 mW. The laser irradiation time was 90 seconds.

Figure 15:
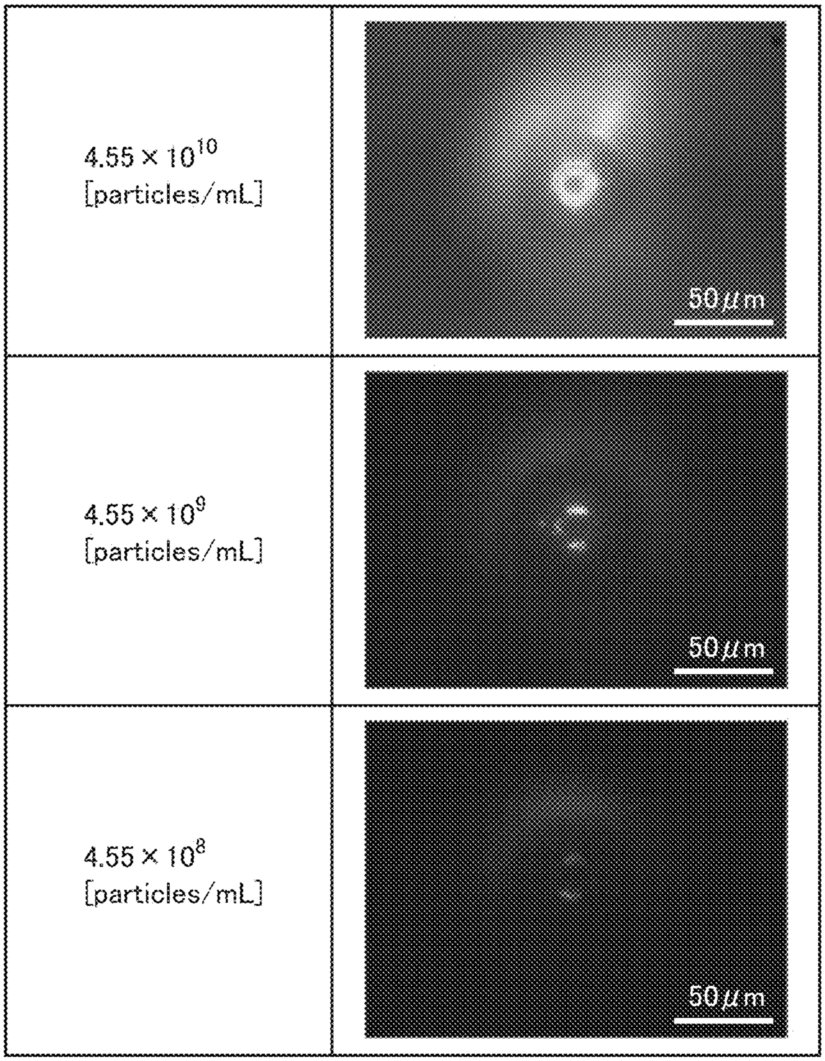
FIG. 15 is a diagram illustrating the fluorescent images of the accumulation results of polystyrene beads.

FIG. 15 is a diagram illustrating the fluorescent images of the accumulation results of polystyrene beads. It was observed that the higher the initial concentration of polystyrene beads, the larger the area of a region for fluorescence emission and the stronger the intensity of fluorescence.

Figure 16:
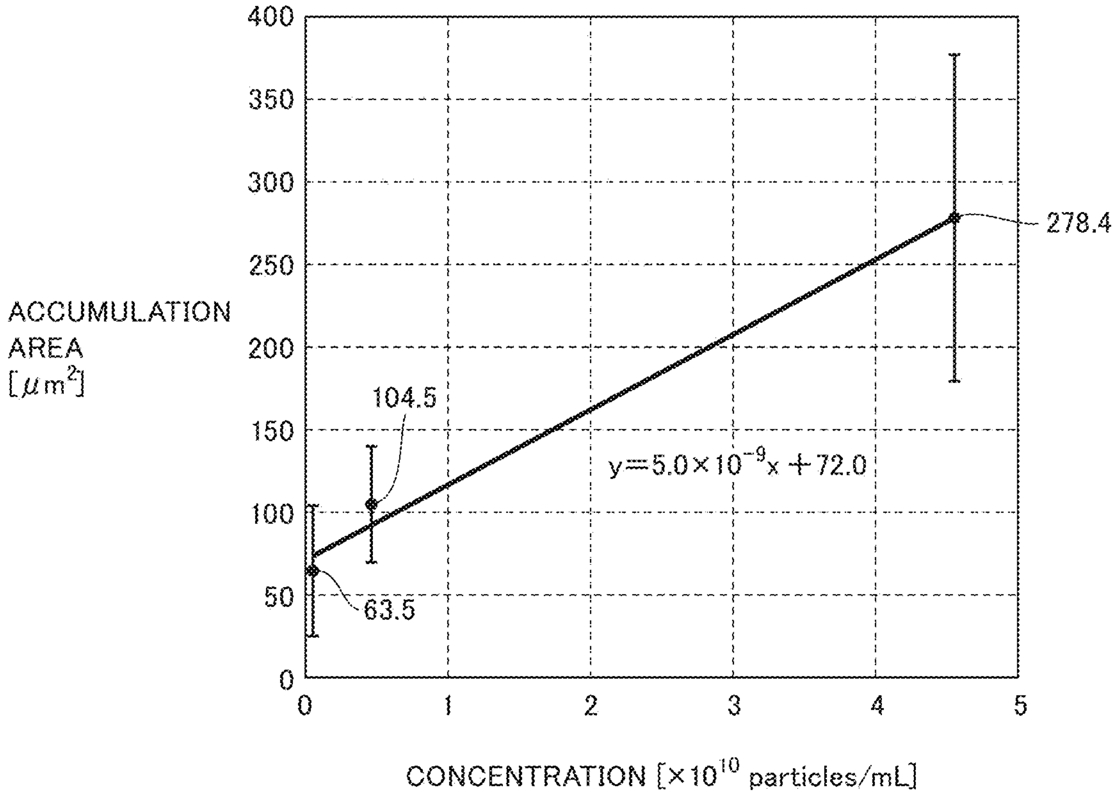
FIG. 16 is a diagram illustrating an example of a calibration curve for calculating the concentration of polystyrene beads in a sample.

FIG. 16 is a diagram illustrating an example of a calibration curve for calculating the concentration of polystyrene beads in the sample. The horizontal axis indicates the initial concentration of polystyrene beads in the sample. The vertical axis indicates the accumulation area of polystyrene beads. An error bar indicates a standard deviation when the number of measurements is 3.

FIG. 16 shows that the accumulation areas of the three samples are located on the same straight line. Thus, a positive correlation indicated by the straight line is determined as a calibration curve by a preliminary experiment and is stored in memory 92 of controller 9. With reference to the calibration curve, controller 9 can calculate the initial concentration of polystyrene beads from the accumulation area of polystyrene beads.

<Accumulation of Bacteria>

The results of accumulation of bacteria will be described below. In this example, *Escherichia coli* was used. *Escherichia coli* is a bacillus having a size with a minor axis of 0.7 μm and a major axis of about 2 to 4 μm. The concentration of *Escherichia coli* was $4.0 \times 10^{8}$ [cells/mL]. The laser output power was 5 mW. The laser irradiation time was 60 seconds. The laser wavelength was 800 nm. *Escherichia coli* was subjected to fluorescent dyeing.

Figure 17:
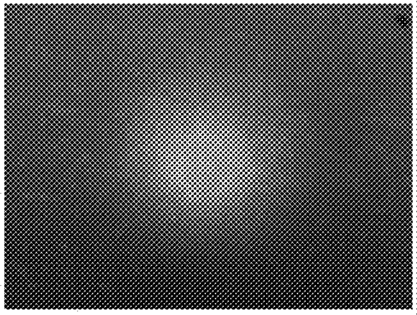
FIG. 17 is a diagram illustrating the fluorescent images of the accumulation results of *Escherichia coli.*
Figure 17:
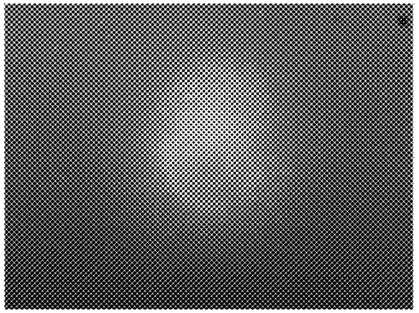
Figure 17:
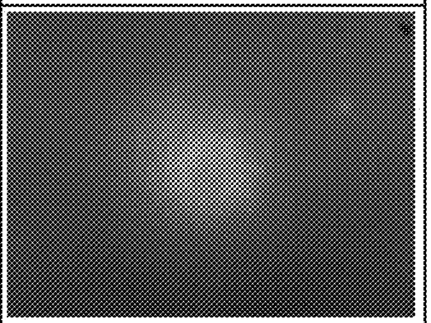
Figure 17:
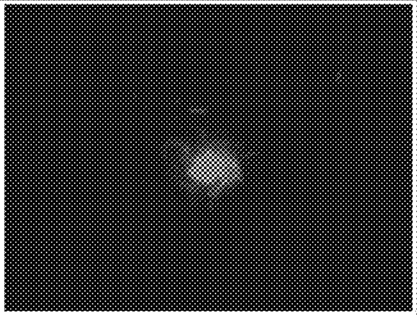
Figure 17:
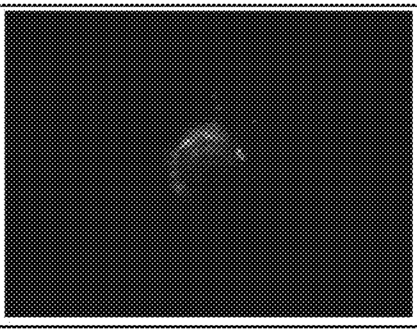
Figure 17:
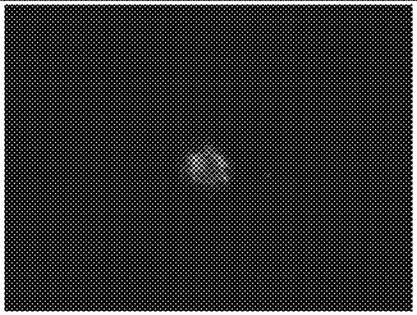

FIG. 17 is a diagram illustrating the fluorescent images of the accumulation results of *Escherichia coli*. FIG. 17 shows the accumulation results of *Escherichia coli* in three samples. SYTO9 ® or PI (Propidium Iodide) was used as fluorescent dyes. SYTO9 dyes both of living bacteria (viable bacteria) and dead bacteria (killed bacteria). When SYTO9 is excited from the outside, green fluorescence is emitted. PI only dyes dead bacteria. When PI is excited from the outside, red fluorescence is emitted.

The survival rate of accumulated *Escherichia coli* can be calculated by analyzing upper fluorescent images (SYTO9 images) using SYTO9 and lower fluorescent images (PI images) using PI. The survival rate means the ratio of the number of living bacteria with respect to the total number of accumulated *Escherichia coli* as expressed by equation (1) below. Since the number of accumulated *Escherichia coli* is typically proportionate to the accumulation area of *Escherichia coli*, the accumulation area can be read as the number.

$$\text{Survival rate} = \text{the number of living bacteria} / (\text{the number of living bacteria} + \text{the number of dead bacteria}) \times 100 \quad (1)$$

In the image analysis of SYTO9 images, the accumulation area of all *Escherichia coli* (living bacteria and dead bacteria) was 1870.92 $\mu m^2$ in sample 1, 1616.67 $\mu m^2$ in sample 2, and 1463.64 $\mu m^2$ in sample 3. In the image analysis of PI images, the accumulation area of dead bacteria was 167.13 $\mu m^2$ in sample 1, 78.99 $\mu m^2$ in sample 2, and 131.75 $\mu m^2$ in sample 3. From these analyses, the survival rates of *Escherichia coli* in samples 1 to 3 were calculated as 91.07%, 95.11%, and 91.00%, respectively. The average survival rate was 92.39%. In this way, according to the present embodiment, most bacteria can be accumulated alive.

<Accumulation of Mimicking Virus>

The accumulation result of "virus-mimicking NPs (nanoparticles)" that are nanoparticles mimicking the novel coronavirus (SARS-COV-2) will be described below.

Figure 18:
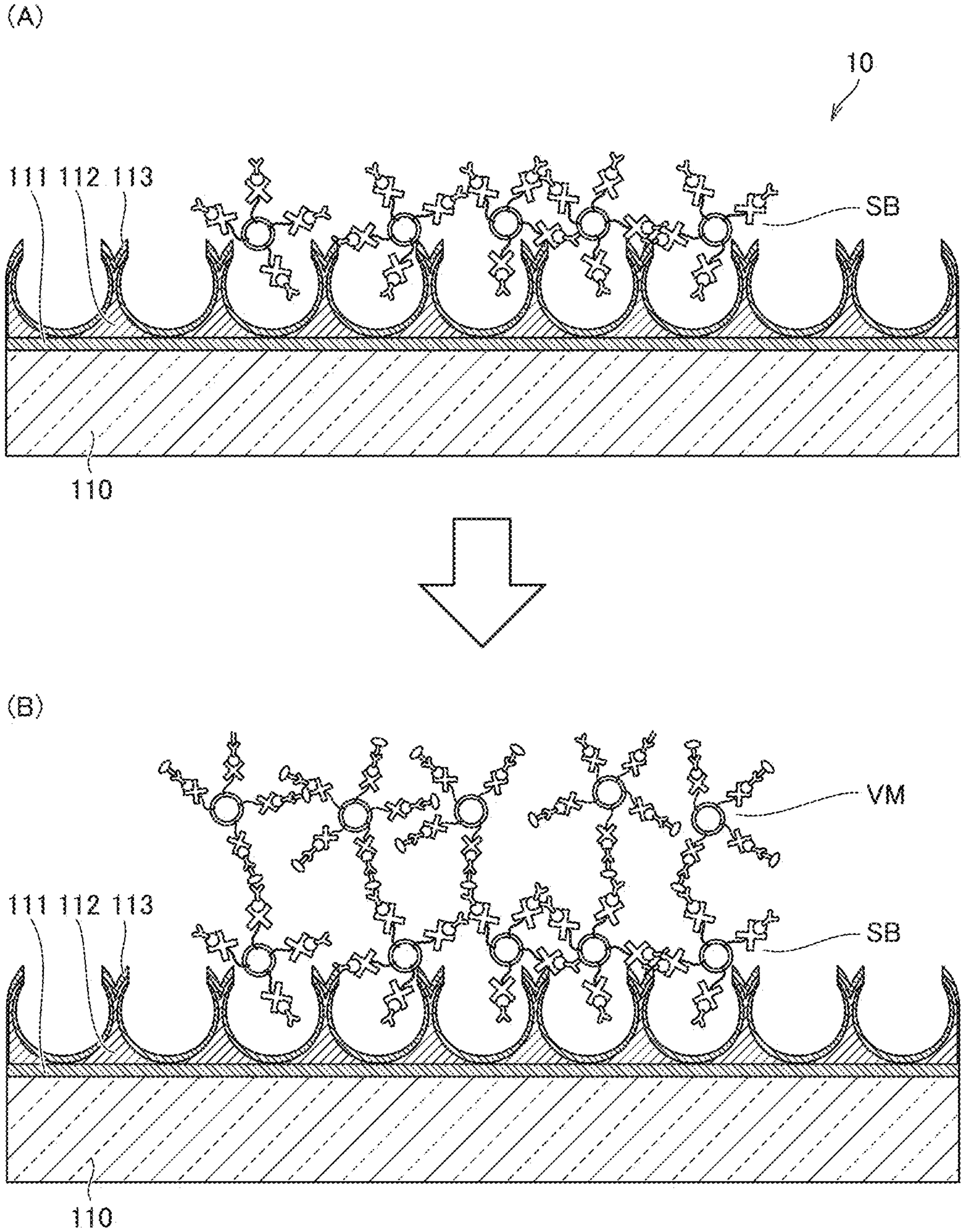
FIG. 18 is a conceptual diagram for explaining a technique of detecting virus-mimicking NPs in the present embodiment.

FIG. 18 is a conceptual diagram for explaining a technique of detecting virus-mimicking NPs in the present embodiment. Two kinds of measurement were conducted using three kinds of dispersion liquids A, B, and C. The first measurement is measurement using dispersion liquid A and dispersion liquid B. The second measurement is measurement using dispersion liquid A and dispersion liquid C. The second measurement is conducted as a control experiment for the first measurement.

The novel coronavirus has spike proteins (S-proteins) on the surface. Spike proteins contain an S1 portion located outside and an S2 portion located inside. Dispersion liquid A contains specific binding nanoparticles SB. Specific binding nanoparticles SB are polystyrene particles modified by streptavidin. The streptavidin is modified by a biotinylated antibody (corresponding to "host substance" according to the present disclosure) that is specifically bound to the S1 portion of spike proteins.

Dispersion liquid B contains virus-mimicking NPs VM. Virus-mimicking NPs VM are polystyrene particles modified by spike proteins such that the S1 portion is located outside. Dispersion liquid C contains control nanoparticles instead of virus-mimicking NPs VM. The control nanoparticles are polystyrene particles simply modified only by streptavidin. In other words, the control nanoparticles are not modified by spike proteins.

In all of the three kinds of dispersion liquids A, B, and C, polystyrene particles serving as cores were 100 nm in diameter. As virus-mimicking NPs VM and the cores of control nanoparticles, fluorescent beads dyed with fluorescent dyes (micromerR®—redF) that emit red were used. The concentration of specific binding nanoparticles SB in the dispersion liquid A was $1.9\times10^{12}$ [particles/mL]. The concentration of virus-mimicking NPs VM in dispersion liquid B was $1.9\times10^{9}$, $1.9\times10^{10}$ or $1.9\times10^{11}$ [particles/mL]. The concentration of the control nanoparticles in dispersion liquid C was $1.9\times10^{9}$, $1.9\times10^{10}$, or $1.9\times10^{11}$ [particles/mL].

The steps of measurement will be described below. First, 5 μL of dispersion liquid A is dropped onto detection kit 10 (micro-bowl substrate or nano-bowl substrate). Thereafter, specific binding nanoparticles SB are subjected to light concentration by irradiating dispersion liquid A with a laser beam. This accumulates specific binding nanoparticles SB on detection kit 10 (see FIG. 18(A)). A region where specific binding nanoparticles SB are accumulated functions as "trap site" for trapping virus-mimicking NPs VM by specific binding with virus-mimicking NPs VM. The dispersion medium of dispersion liquid A is removed by an air duster (not illustrated). Thereafter, 5 μL of dispersion liquid B is dropped onto detection kit 10. Virus-mimicking NPs VM are subjected to light concentration by irradiating dispersion liquid B with a laser beam. Thus, virus-mimicking NPs VM are further accumulated in the region where specific binding nanoparticles SB have been accumulated (see FIG. 18(B)). The surface of detection kit 10 is then cleaned. Subsequently, a fluorescent image is captured. In the second measurement, the same steps are performed except that dispersion liquid C is used instead of dispersion liquid B.

Figure 19:
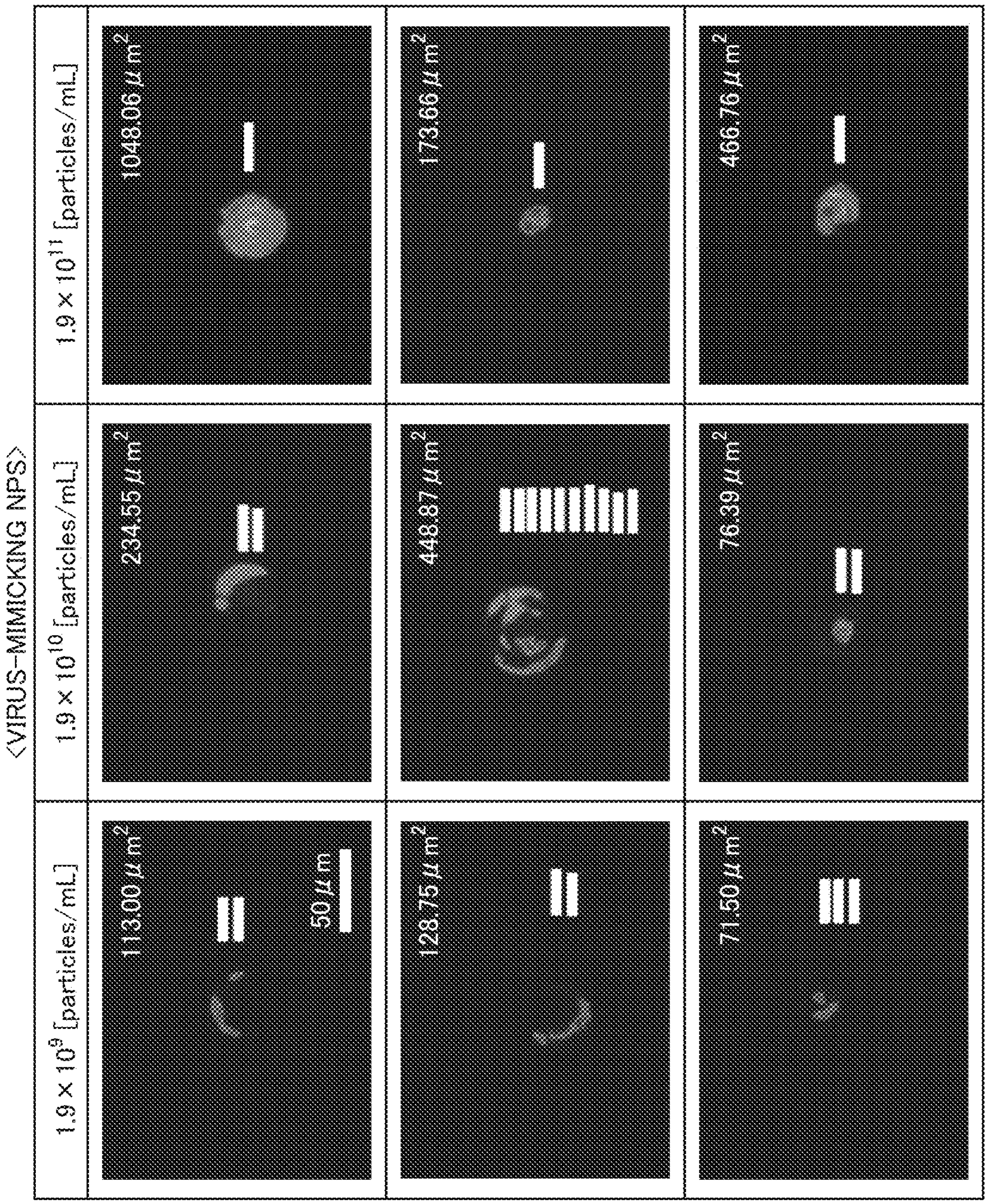
FIG. 19 is a diagram illustrating the fluorescent images of the accumulation results of virus-mimicking NPs when a dispersion liquid containing virus-mimicking NPs is used.
Figure 20:
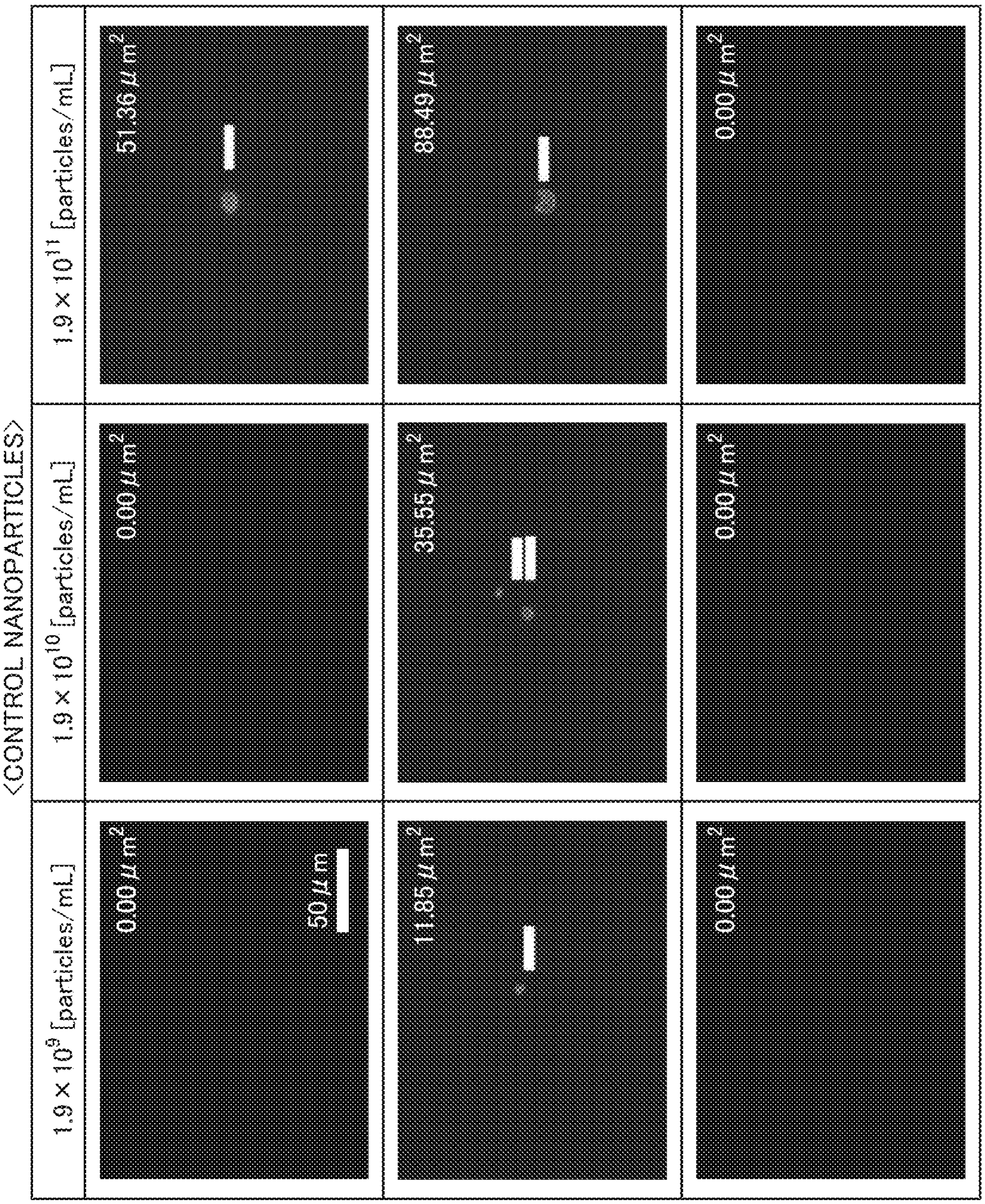
FIG. 20 is a diagram illustrating the fluorescent images of the accumulation results of control nanoparticles when a dispersion liquid not containing the virus-mimicking NPs is used.

FIG. 19 is a diagram illustrating the fluorescent images of the accumulation results of virus-mimicking NPs VM when dispersion liquid B containing virus-mimicking NPs NB is used (first measurement). FIG. 20 is a diagram illustrating the fluorescent images of the accumulation results of the control nanoparticles when dispersion liquid C not containing virus-mimicking NPs NB is used (second measurement). The laser output power was 10 mW. The laser irradiation time was 60 seconds. The laser wavelength was 800 nm. The position of detection kit 10 was adjusted by adjusting mechanism 2 such that the beam waist of a laser beam is located at 10 μm lower than the bottom portion 11 of detection kit 10.

At a concentration of $1.9\times10^{10}$ [particles/mL], fluorescence was observed when virus-mimicking NPs VM were contained, whereas fluorescence was hardly observed when virus-mimicking NPs VM were not contained. At a higher concentration of $1.9\times10^{11}$ [particles/mL], fluorescence was slightly observed also when virus-mimicking NPs VM were not contained. However, a fluorescence area in the absence of virus-mimicking NPs VM was quite smaller than a fluorescence area in the presence of virus-mimicking NPs VM (see the lower right image).

As described above, according to the present embodiment, virus-mimicking NPs (that is, the novel coronavirus) can be specifically detected and a difference in concentration of virus-mimicking NPs can be quantified by a fluorescence area. Thus, the concentration of virus-mimicking NPs in the sample can be quantified by creating a calibration curve from the accumulation results of the virus-mimicking NPs at three (or more) concentrations as will be described below.

Figure 21:
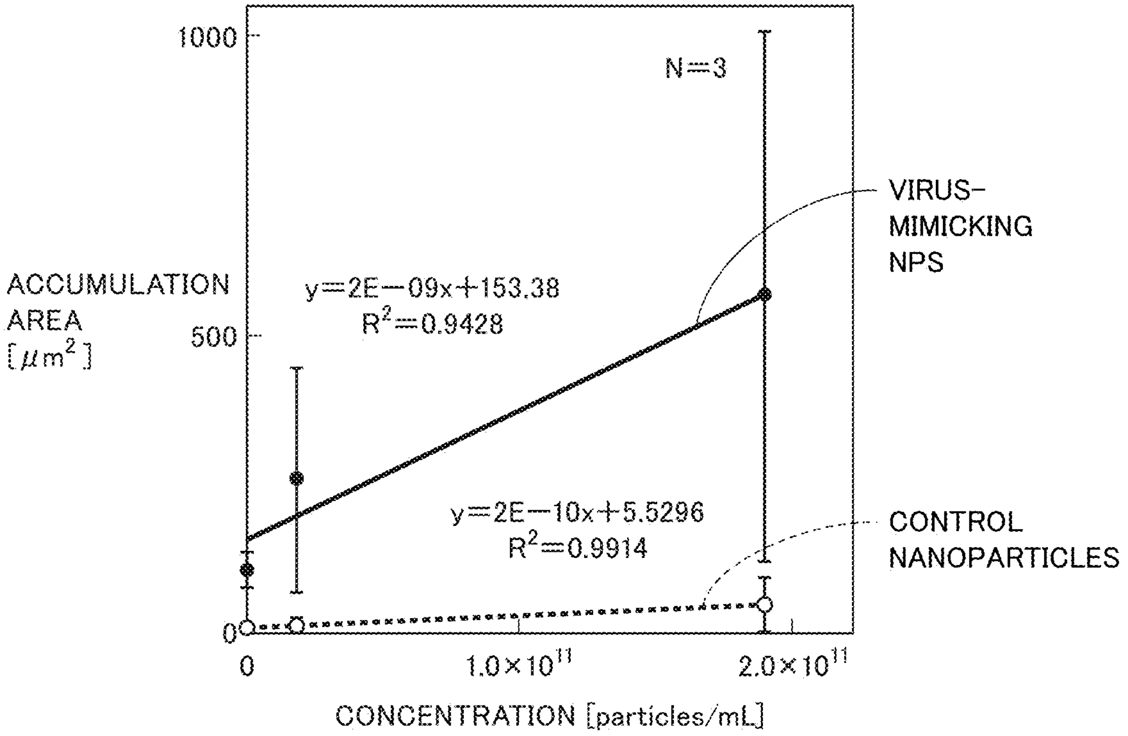
FIG. 21 is a diagram illustrating an example of a calibration curve for calculating the concentration of the virus-mimicking NPs in the sample.

FIG. 21 is a diagram illustrating an example of a calibration curve for calculating the concentration of the novel coronavirus in the sample. The horizontal axis indicates the initial concentration of virus-mimicking NPs in the sample. The vertical axis indicates the accumulation area of virus-mimicking NPs. An error bar indicates a standard deviation when the number of measurements is 3. FIG. 21 also shows the result of a control experiment.

It is assumed that droplets with a diameter of 5 μm from a patient infected with the novel coronavirus (COVID-19) contain ten to 1000 novel coronaviruses (see N. Leung, et al, Nat Med, Lett., 26, 676-680(2020)). If droplets with a diameter of 5 μm contain ten novel coronaviruses, the concentration of the novel coronaviruses is $1.52\times10^{11}$ [particles/mL]. This concentration is within a concentration range of $1.9\times10^{10}$ to $1.9\times10^{11}$ [particles/mL] in the current successful detection. Thus, the measurement results of FIGS. 19 to 21 suggest the probability of detection of the novel coronavirus even from quite a small amount of a sample, for example, droplets.

In this example, a standard deviation increases with a concentration. This may be because accumulated structures increase in size with an increase in concentrations and this increase in size may cause more variations when being cleaned during the surface cleaning of detection kit 10. A relatively small standard deviation is obtained at a low concentration. Thus, viruses may be detected with high sensitivity even at a low concentration at the beginning of infection.

It should be noted that in this example, the novel coronavirus was described, the present embodiment is also applicable to other viruses. Moreover, the present embodiment is also applicable to proteins, antibodies, and a composite containing proteins and antibodies instead of or in addition to viruses.

<Shrinkage of Microbubbles>

A method for enabling the detection of microscopic objects at a lower concentration will be described below.

Figure 22:
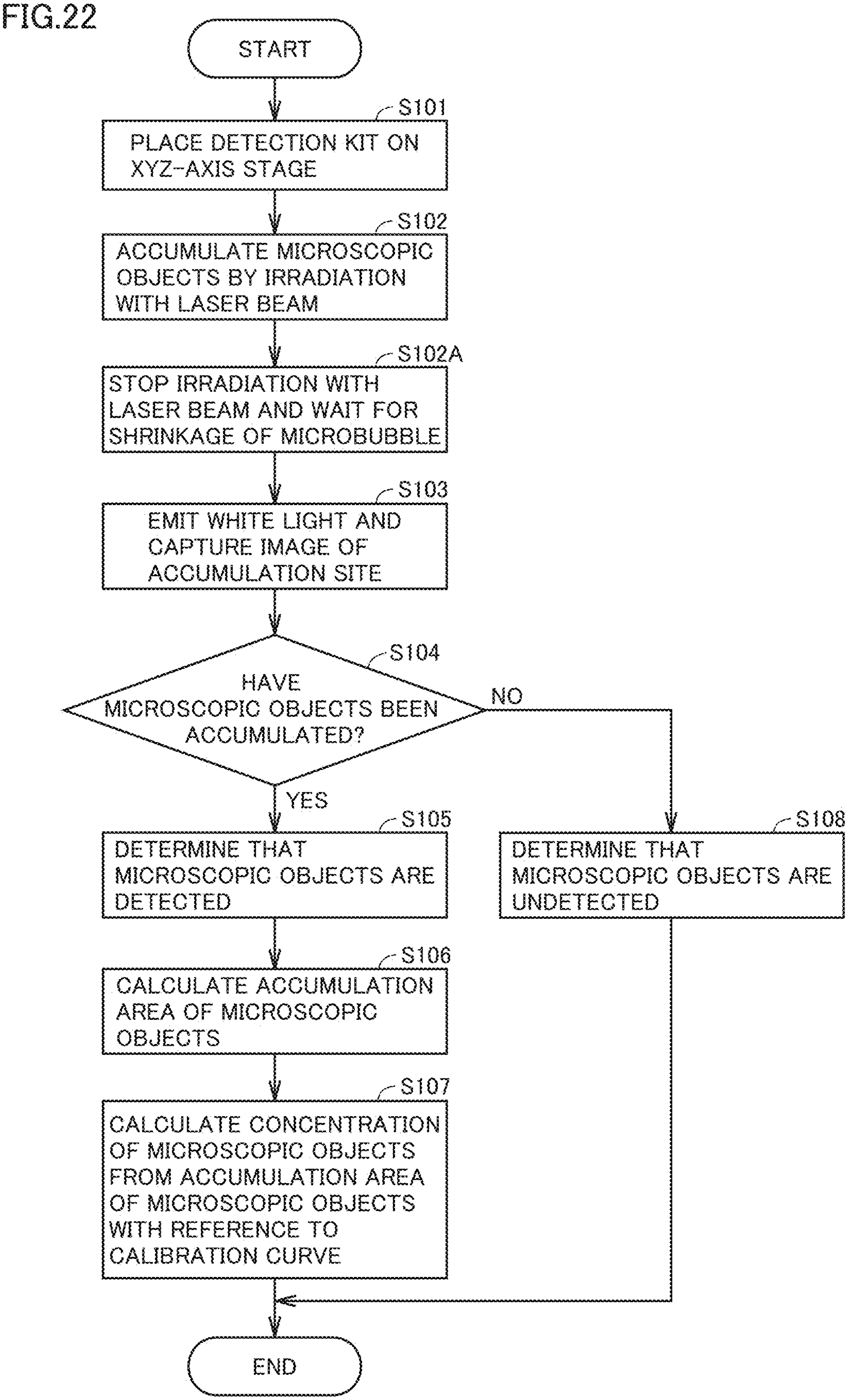
FIG. 22 is a flowchart indicating another example of the steps of the method for detecting microscopic objects according to Embodiment 1.

FIG. 22 is a flowchart indicating another example of the steps of the method for detecting microscopic objects according to Embodiment 1. The flowchart is different from the flowchart shown in FIG. 11 in that the processing of S102A is included between S102 and S103. After a laser beam is outputted to perform light concentration in S102, controller 9 stops the irradiation with the laser beam and stands by for a predetermined time (S102A). Thereafter, controller 9 controls imaging device 6 so as to capture an image of an accumulation site (S103).

Figure 23:
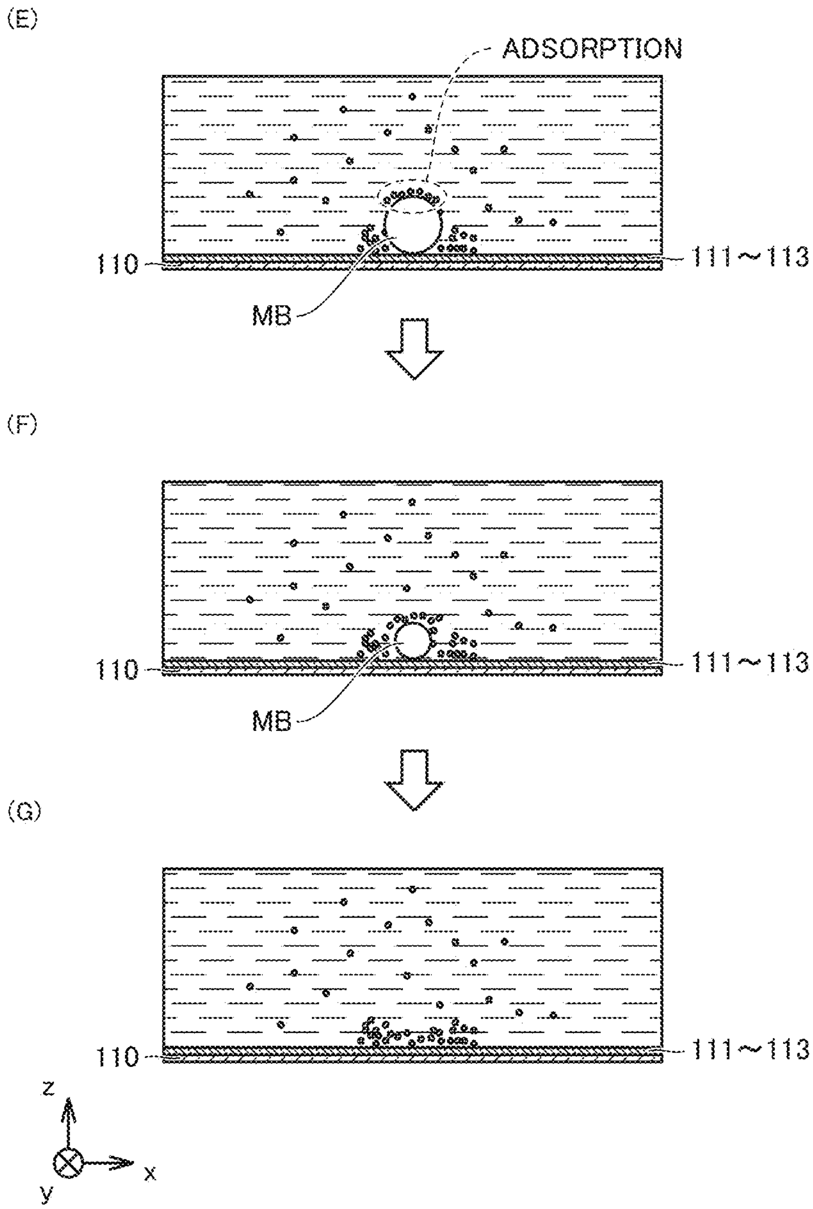
FIG. 23 is a diagram for explaining an accumulation mechanism of microscopic objects after the stop of irradiation with a laser beam.

FIG. 23 is a diagram for explaining an accumulation mechanism of microscopic objects after the stop of irradiation with a laser beam. FIG. 23 illustrates a mechanism created after FIG. 10(D). When the irradiation with a laser beam is stopped, some of microscopic objects conveyed by thermal convection are adsorbed onto the upper surface of a microbubble (see FIG. 23(E)). After the stop of irradiation with the laser beam, the microbubble shrinks with the passage of time (see FIG. 23(F)). As the microbubble shrinks, the position of the upper surface of the microbubble is lowered. Accordingly, microscopic objects adsorbed on the upper surface of the microbubble also move downward. Thus, when the microbubble disappears, the microscopic objects adsorbed on the upper surface of the microbubble are accumulated at a position where the microbubble was present (see FIG. 23(G)). The processing of accelerating the accumulation of microscopic objects by using shrinkage of a microbubble will be also referred to as "bubble shrinkage processing."

Figure 24:
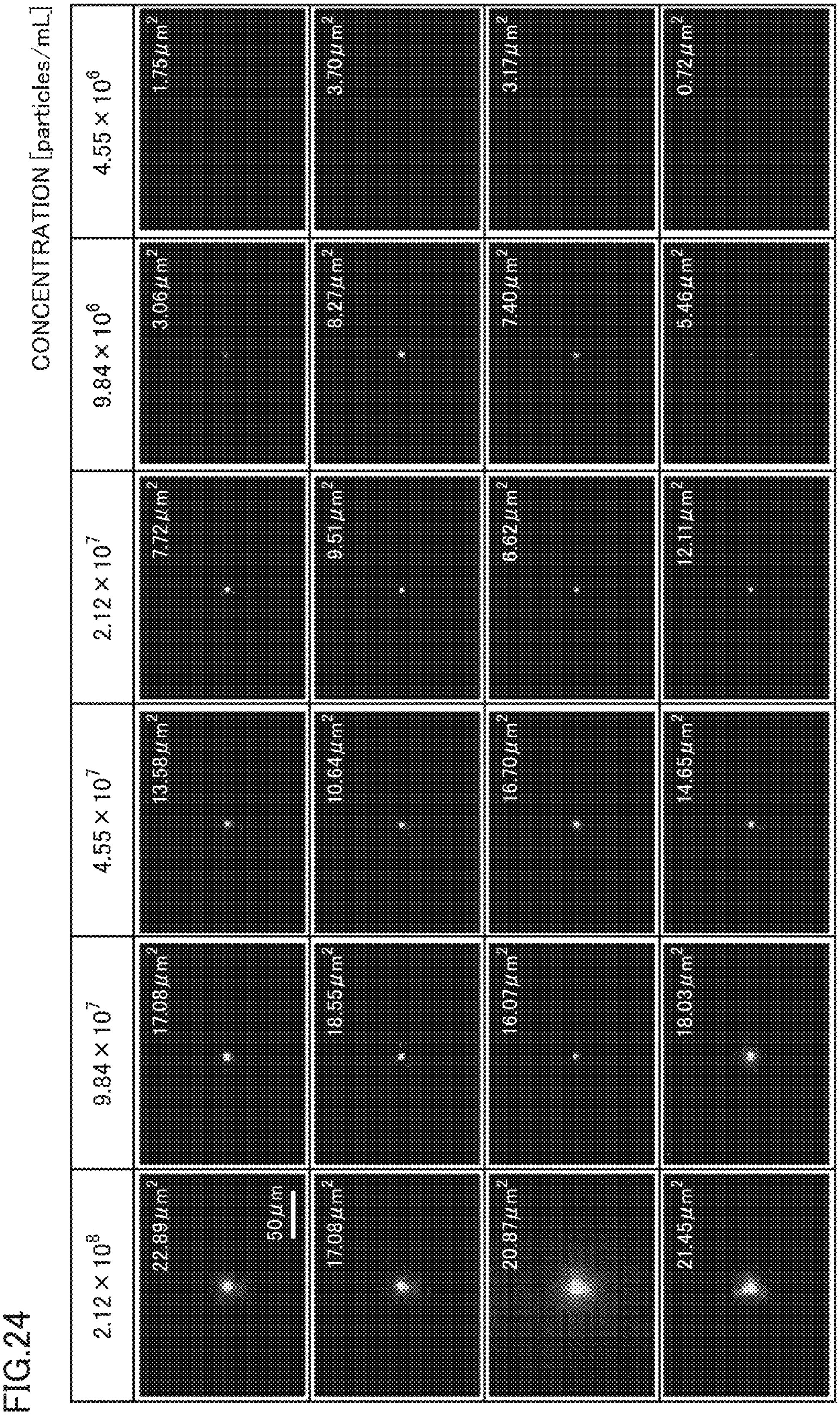
FIG. 24 is a diagram illustrating the fluorescent images of the accumulation results of microscopic objects at various concentrations when bubble shrinkage processing is performed.

FIG. 24 is a diagram illustrating the fluorescent images of the accumulation results of microscopic objects at various concentrations when the bubble shrinkage processing is performed. Six samples with different concentrations were prepared. As microscopic objects, fluorescent beads (Fluoresbrite YG of Polysciences, Inc.) that emit yellow green fluorescence were used. The fluorescent beads were 100 μm in diameter. A nano-bowl substrate was used. The laser output power was 100 mW. The laser irradiation time was 30 seconds. The laser wavelength was 800 nm. The position of the nano-bowl substrate was adjusted by the adjusting mechanism 2 such that the beam waist of a laser beam is located at 10 μm lower than the bottom of the nano-bowl substrate. A standby time after the stop of laser irradiation was 60 seconds.

FIG. 24 shows that the fluorescent beads were accumulated even at the lowest concentration of $4.55\times10^{6}$ [particles/mL]. This concentration is about one hundredth of the lower concentration limit of $4.55\times10^{8}$ [particles/mL] at which fluorescent beads can be accumulated when the bubble shrinkage processing is not performed. In other words, by the bubble shrinkage processing, the lower concentration limit, at which microscopic objects can be accumulated, is reduced by two digits as compared with the absence of the bubble shrinkage processing. This indicates that the bubble shrinkage processing may improve the detection sensitivity of microscopic objects by two digits.

Figure 25:
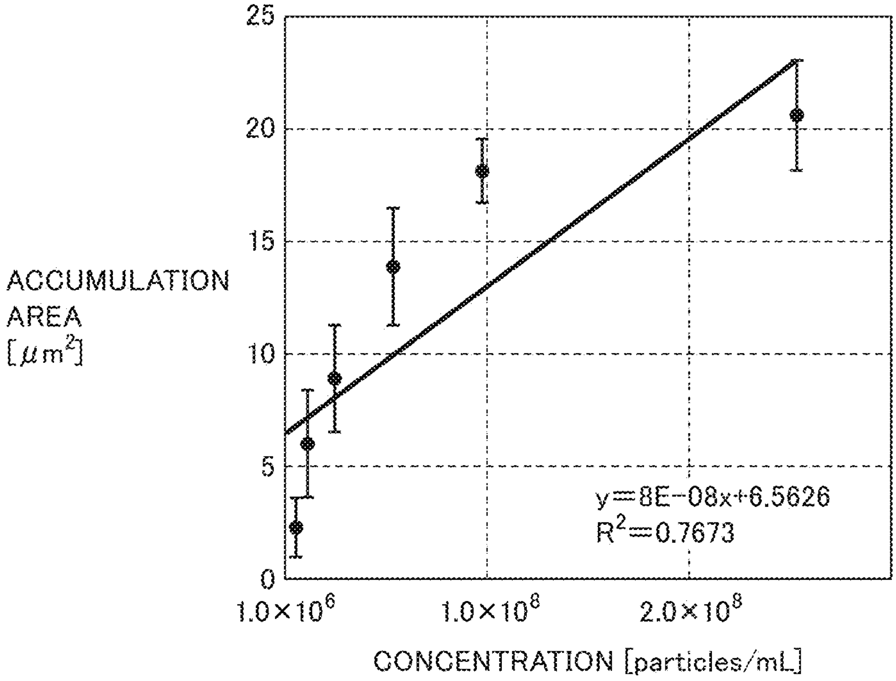
FIG. 25 is a diagram illustrating a first example of a calibration curve for calculating the concentration of microscopic objects in the sample when the bubble shrinkage processing is performed.

FIG. 25 is a diagram illustrating a first example of a calibration curve for calculating the concentration of microscopic objects in the sample when the bubble shrinkage processing is performed. The horizontal axis indicates the concentration of microscopic objects (fluorescent beads). The vertical axis indicates the accumulation area of microscopic objects.

FIG. 25 shows that the plot of the accumulation area at each concentration is deviated from a calibration curve like a straight line obtained by curve fitting using a linear function. This is because microscopic objects form three-dimensional structures when the amount of accumulation of the microscopic objects is increased by bubble shrinkage processing. If the microscopic objects are three-dimensionally accumulated, the accumulation area does not linearly increase as the microscopic objects are accumulated. Thus, a plotting method may be devised for the correlation between the concentration of the microscopic objects and the concentration of accumulation.

Figure 26:
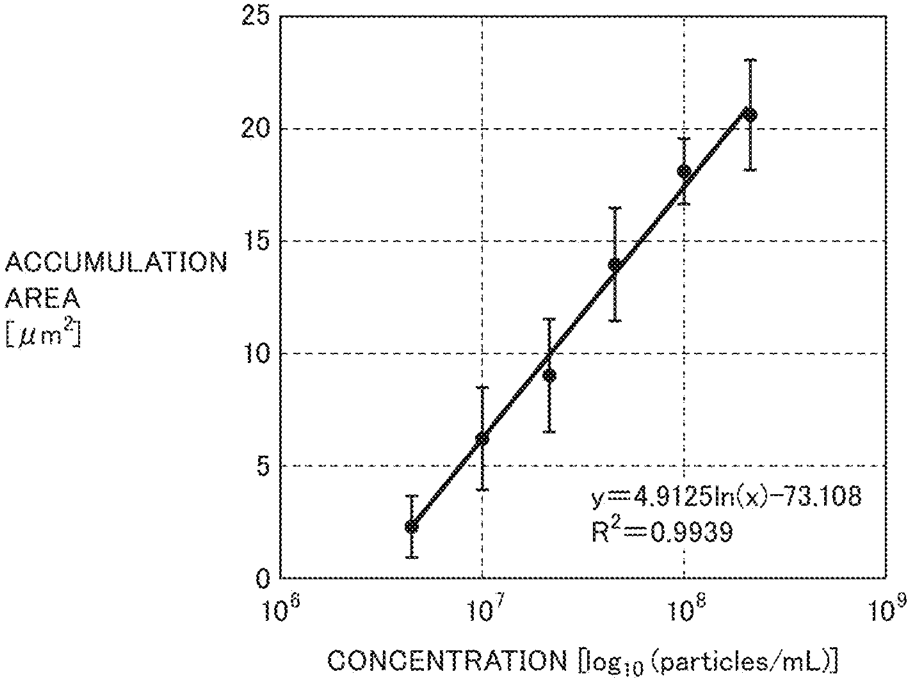
FIG. 26 is a diagram illustrating a second example of a calibration curve for calculating the concentration of microscopic objects in the sample when the bubble shrinkage processing is performed.
Figure 27:
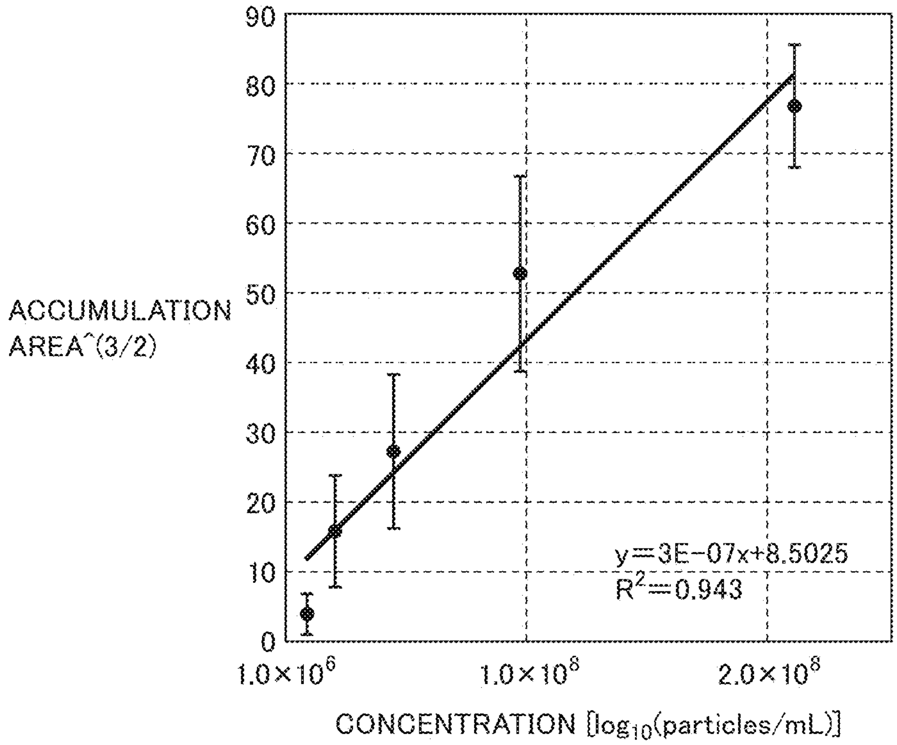
FIG. 27 is a diagram illustrating a third example of a calibration curve for calculating the concentration of microscopic objects in the sample when the bubble shrinkage processing is performed.

FIG. 26 is a diagram illustrating a second example of a calibration curve for calculating the concentration of microscopic objects in the sample when the bubble shrinkage processing is performed. FIG. 27 is a diagram illustrating a third example of a calibration curve for calculating the concentration of microscopic objects in the sample when the bubble shrinkage processing is performed. The horizontal axes in FIGS. 26 and 27 indicate the concentration of microscopic objects in common logarithm. The vertical axis in FIG. 26 indicates the accumulation area of microscopic objects. The vertical axis in FIG. 27 indicates the three-halves power value of the accumulation area of microscopic objects. The three-halves power is an operation for artificially converting an area into a volume.

A comparison among FIGS. 25 to 27 proves that a calibration curve with the highest linearity is obtained in FIG. 26 that is a semilogarithmic plot. Thus, a calibration curve with high linearity can be created by adopting a proper plotting method depending on the amount of accumulation of microscopic objects to be quantified.

As described above, in Embodiment 1, the nano-bowl substrate is used instead of the micro-bowl substrate in order to accumulate a plurality of microscopic objects dispersed in the sample. A nano-bowl structure disposed in the nano-bowl substrate has quite a small size. Specifically, a bowl diameter φ of each nano-bowl structure is sufficiently smaller than a spot diameter D of a laser beam, and a plurality of nano-bowl structures are included in a laser spot. Bowl diameter φ is desirably smaller than the wavelength (e.g., 1064 nm, 800 nm) of a laser beam. Under such conditions, the photothermal effect is considerably enhanced as the surface area of the metallic thin film 113 increases. Thus, even in the case of low laser output power, microbubbles can be generated with a high probability. Thus, according to Embodiment 1, a plurality of microscopic objects dispersed in a sample can be efficiently accumulated. Moreover, the accumulation time of microscopic objects is shortened, so that the microscopic objects in a sample can be quickly detected.

Embodiment 2

In Embodiment 2, a configuration for detecting microscopic objects on the basis of the reflection spectrum of a detection kit 10 will be described. The overall configuration of a detection system of microscopic objects is equivalent to the configuration shown in FIG. 1 and thus a description thereof will not be repeated. In the following measurement example, as detection kit 10, in addition to a nano-bowl substrate and a micro-bowl substrate, a flat substrate was further used. A metallic thin film 211 (thin gold film) was formed on the flat substrate, while a bowl-like structure was not formed.

Figure 28:
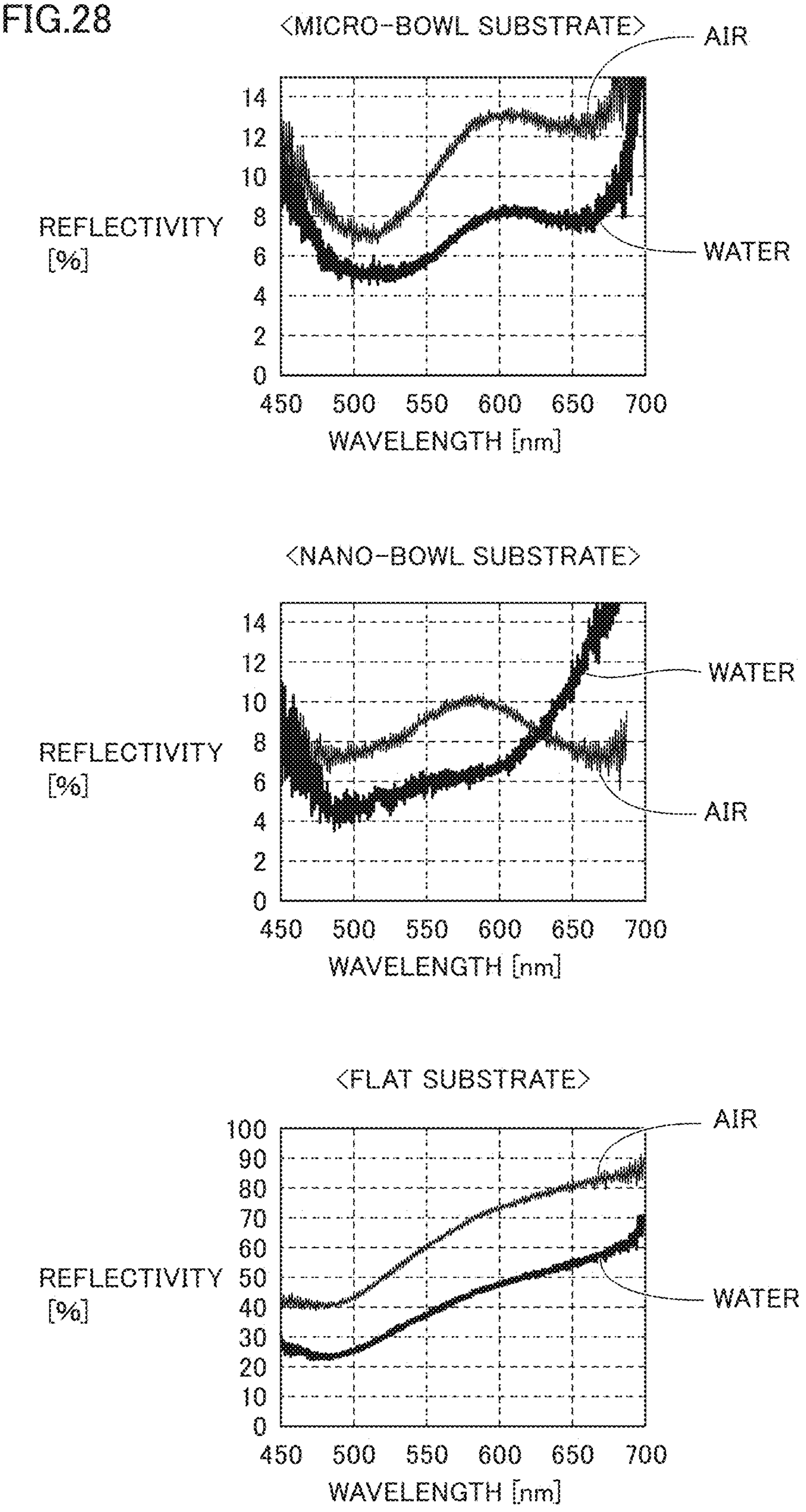
FIG. 28 is a diagram illustrating an example of measurement results on the transmission spectrum of the detection kit.

FIG. 28 is a diagram illustrating examples of measurement results on the reflection spectrum of detection kit 10. Air or water was used as samples. The samples do not contain microscopic objects.

In the flat substrate, the intensity of the reflection spectrum changed depending upon the kind of sample (air or water) but the reflection spectrum had similar shapes. In the micro-bowl substrate, the shape of the reflection spectrum changed in addition to the intensity of the reflection spectrum. Specifically, a peak shift of the reflection spectrum was observed. In the nano-bowl substrate, the intensity and shape of the reflection spectrum considerably changed as compared with the micro-bowl substrate. Since the samples do not contain microscopic objects, the peak shift in FIG. 28 is assumed to be derived from the localized surface plasmon of a metallic thin film 113 disposed in the bowl-like structure.

Figure 29:
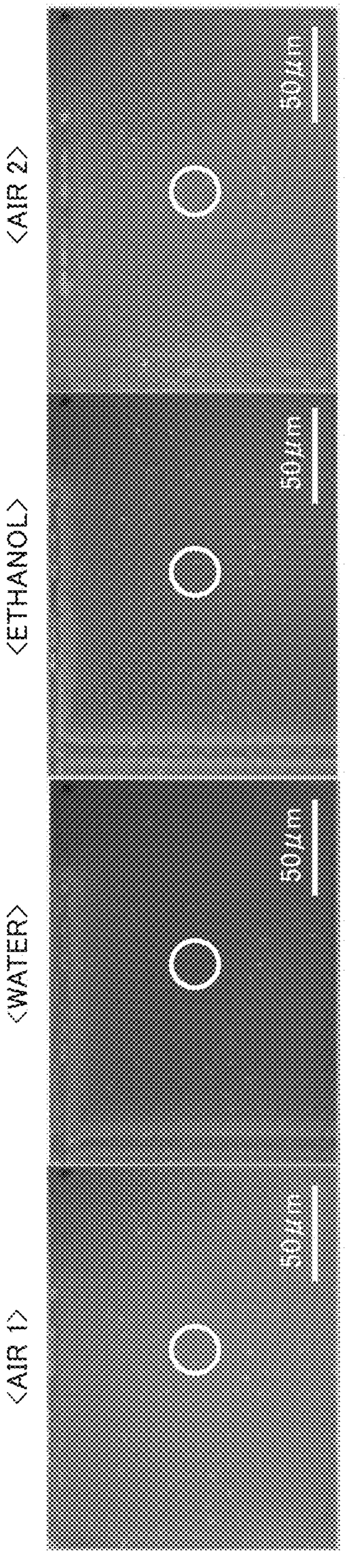
FIG. 29 is a diagram illustrating the images of the detection kit to be measured.

FIG. 29 is a diagram illustrating the images of detection kit 10 to be measured. In this example, a nano-bowl substrate was used for detection kit 10. Air, water, and ethanol were used as samples. The samples do not contain microscopic objects. As shown in FIG. 29, a change of the color of the nano-bowl substrate depending upon the kind of sample was visually confirmed.

Figure 30:
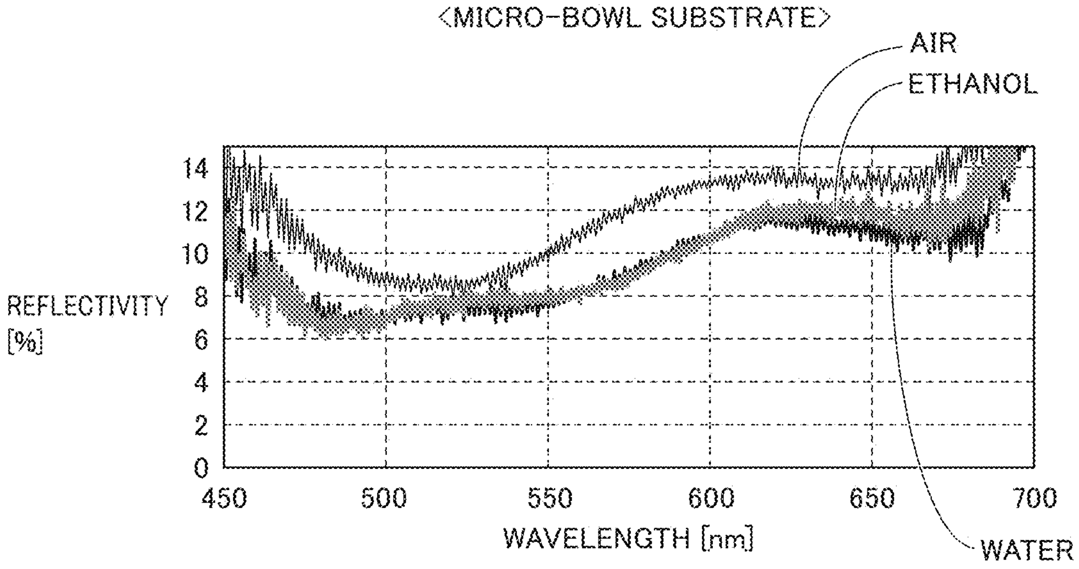
FIG. 30 is a diagram illustrating measurement results on the reflection spectrums of the samples shown in FIG. 29.
Figure 30:
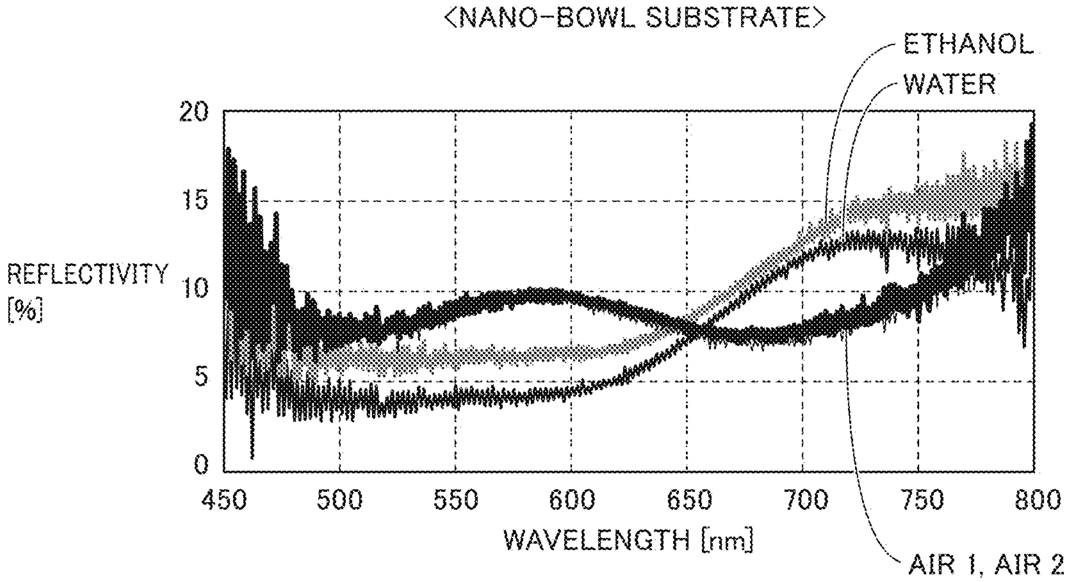

FIG. 30 is a diagram illustrating measurement results on the reflection spectrums of the samples in FIG. 29. FIG. 30 also shows measurement results on a reflection spectrum in the use of the micro-bowl substrate.

In the micro-bowl substrate, a difference (peak shift amount) was about 20 nm between the peak wavelength of the reflection spectrum of air used as a sample and the peak wavelength of the reflection spectrum of water used as a sample. A peak shift amount in the nano-bowl substrate was about 120 nm. In other words, the peak shift amount in the nano-bowl substrate was about six times as large as the peak shift amount in the micro-bowl substrate. This means that a difference in refractive index between the samples can be detected with high sensitivity by using the nano-bowl substrate. Actually, only a small difference exists between the refractive index (1.33) of water and the refractive index (1.36) of ethanol, but a peak shift of the reflection spectrum was detected between sample water and sample ethanol.

After water or liquid was dropped as a sample onto the nano-bowl substrate to measure a reflection spectrum, the sample was removed to measure a reflection spectrum again. In this case, the same measurement result was obtained as that before the sample was dropped (that is, the sample was air). The same result was obtained for the micro-bowl substrate. These results indicate that the nano-bowl substrate and the micro-bowl substrate can be repeatedly used.

Figure 31:
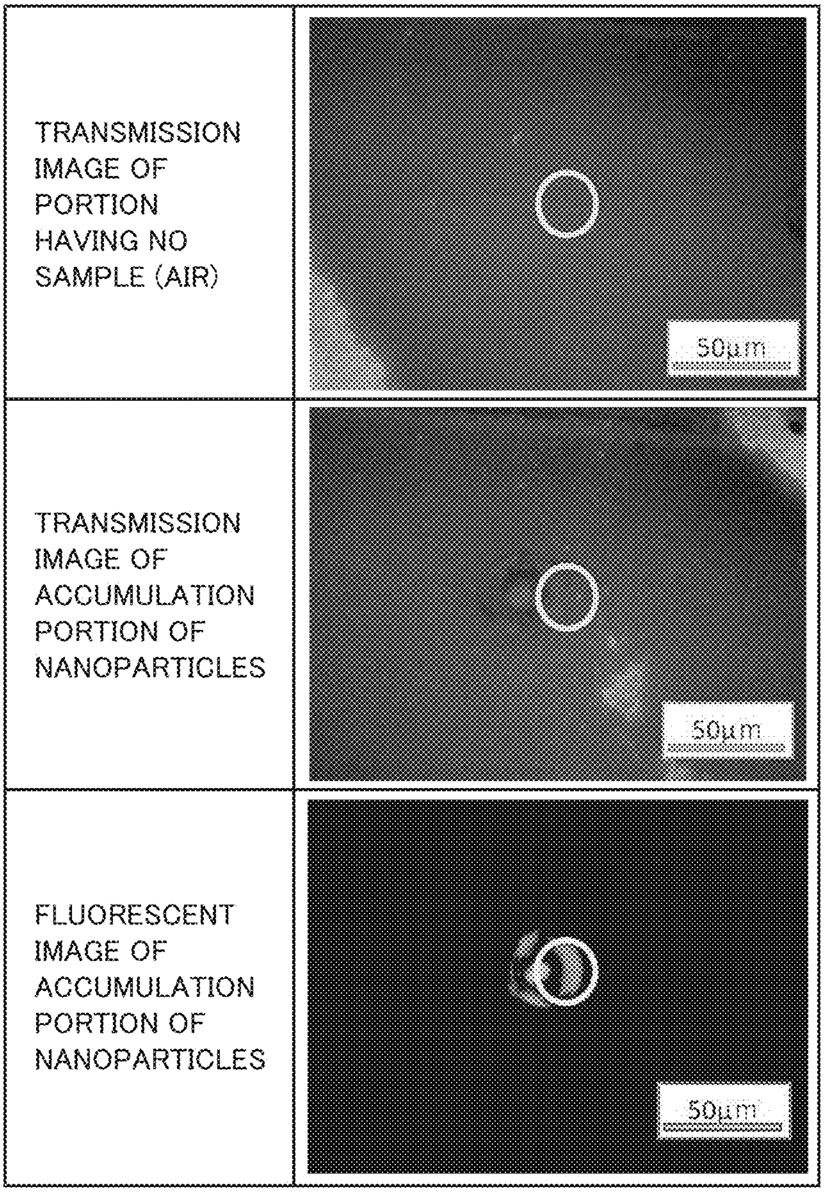
FIG. 31 is a diagram illustrating the measurement regions of the reflection spectrum of the detection kit when the sample contains microscopic objects.
Figure 32:
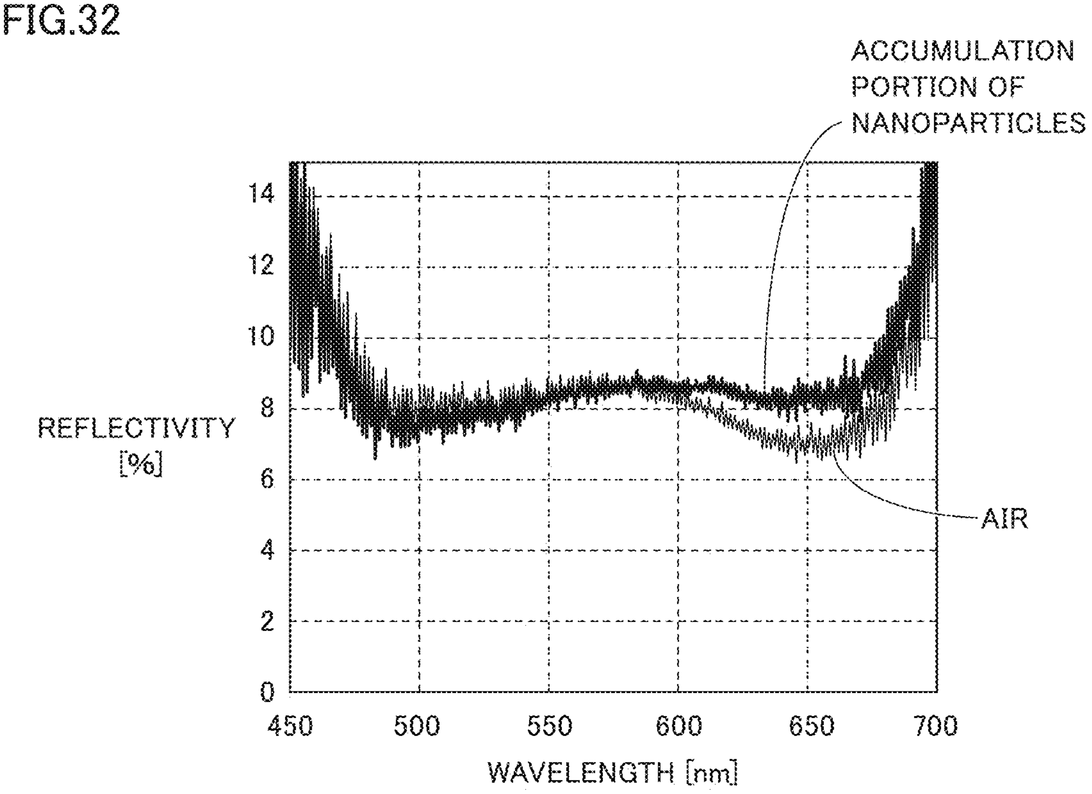
FIG. 32 is a diagram illustrating an example of the measurement result of the reflection spectrum of the detection kit when the sample contains microscopic objects.

FIG. 31 is a diagram illustrating the measurement regions of the reflection spectrum of detection kit 10 when the sample contains microscopic objects. FIG. 32 is a diagram illustrating an example of the measurement result of the reflection spectrum of detection kit 10 when the sample contains microscopic objects. A nano-bowl substrate was used for detection kit 10. Polystyrene beads with a particle size of 100 nm were used as microscopic objects. Water was used as a dispersion medium. The concentration of the polystyrene beads was $4.55\times10^{10}$ [particles/mL]. The volume of the sample was 20 μL. Regions surrounded by circles in FIG. 31 are the measurement regions of the reflection spectrum. As shown in FIG. 32, a long-wavelength shift of the reflection spectrum was confirmed also in the sample containing the microscopic objects.

The concentration of polystyrene beads, $4.55\times10^{10}$ [particles/mL], is substantially the same as the concentration of the novel coronavirus contained in the droplets described above. Thus, the measurement result of FIG. 32 suggests the probability of detection of the novel coronavirus from quite a small amount of a sample, for example, droplets also when the reflection spectrum is used.

Figure 33:
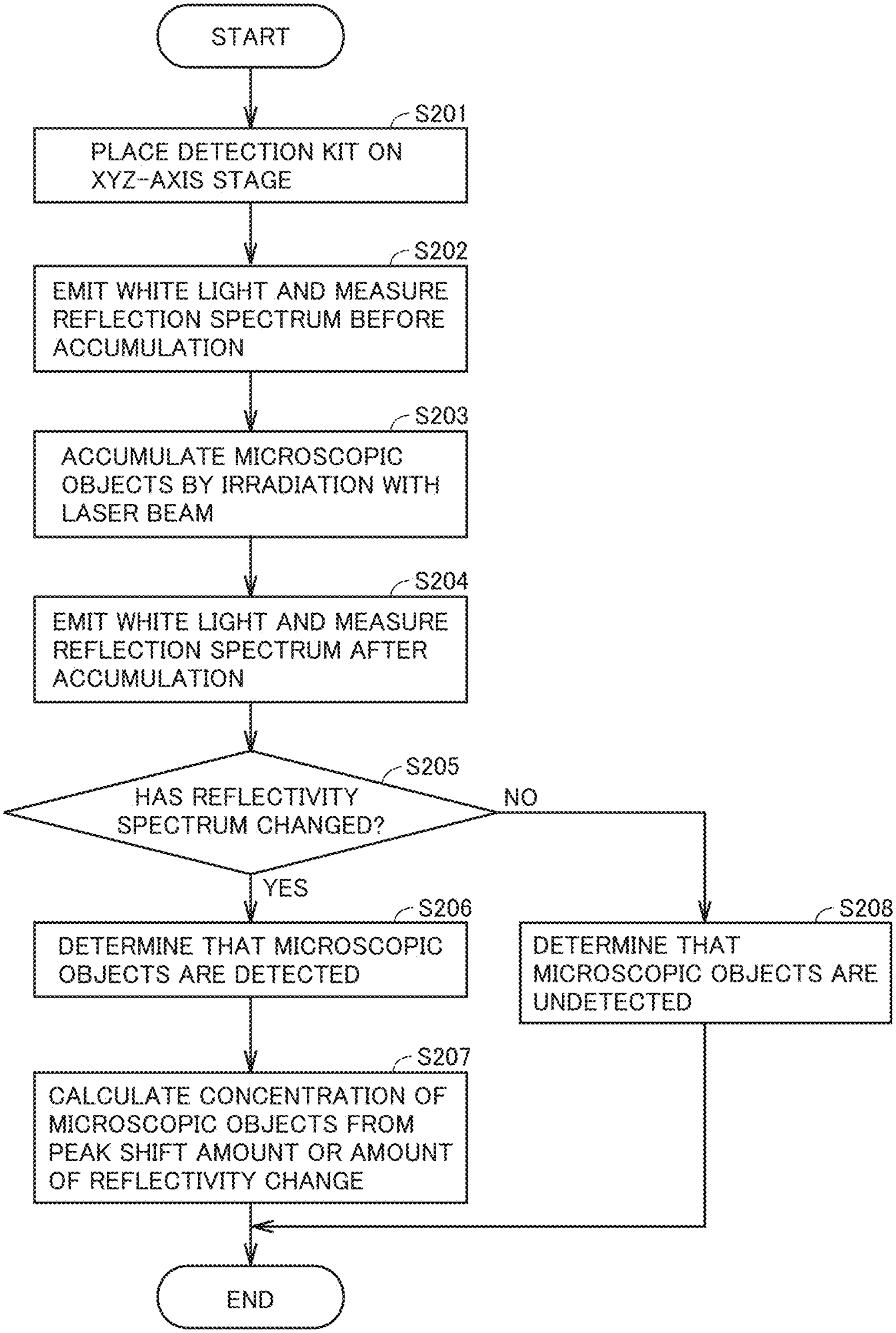
FIG. 33 is a flowchart indicating the steps of a method for detecting microscopic objects according to Embodiment 2.

FIG. 33 is a flowchart indicating the steps of a method for detecting microscopic objects according to Embodiment 2. In S201, detection kit 10 with a sample prepared on a bowl region is placed on an xyz-axis stage 1.

In S202, a controller 9 controls an illumination light source 4 so as to emit white light. Controller 9 then acquires, from a spectrophotometer 7, the reflection spectrum of a region to be irradiated with a laser beam in the bowl region before the irradiation with the laser beam.

In S203, controller 9 controls a laser light source 3 so as to output a laser beam with predetermined power for a predetermined time. Thus, microscopic objects are accumulated in the irradiation region (laser spot) of the laser beam. After the microscopic objects are accumulated, the irradiation with the laser beam is stopped.

In S204, controller 9 acquires the reflection spectrum of the laser spot from spectrophotometer 7. After the acquisition of the reflection spectrum, the irradiation with white light can be terminated.

In step S205, controller 9 determines the presence or absence of a change of the reflection spectrum by comparing the reflection spectrum acquired in S203 and the reflection spectrum acquired in S204. Controller 9 can determine the presence of a change of the reflection spectrum when a peak shift equal to or larger than a predetermined amount is detected. Alternatively, controller 9 can determine the presence of a change of the reflection spectrum when a reflectivity change equal to or larger than a predetermined amount is detected. If a change of the reflection spectrum is not detected (NO at S205), controller 9 determines that the sample does not contain microscopic objects (S208).

If a change of the reflection spectrum is detected (YES at S205), controller 9 calculates the concentration of microscopic objects contained in the sample from a peak shift amount (S207). Alternatively, controller 9 may calculate the concentration of microscopic objects contained in the sample from an amount of reflectivity change. The processing is implemented by determining a calibration curve in advance between a peak shift amount or an amount of reflectivity change and the concentration of microscopic objects like the calibration curve described in, for example, FIG. 15. The specific measurement results will be indicated in examples (see FIGS. 34 to 37), which will be discussed later. At the completion of the processing of S207 or S208, controller 9 returns the processing to the main routine.

Detection systems 100 and 101 according to Embodiments 1 and 2 are provided with both of imaging device 6 and spectrophotometer 7 (see FIG. 1). However, if microscopic objects are detected on the basis of the accumulation area of the microscopic objects as in Embodiment 1, spectrophotometer 7 may be omitted. If microscopic objects are detected on the basis of the reflection spectrum of the bowl region as in Embodiment 2, imaging device 6 may be omitted. However, with the system configuration including both of imaging device 6 and spectrophotometer 7, a method (accumulation area/reflection spectrum) used for detecting microscopic objects can be properly selected. Alternatively, the two methods can be used in combination.

Example of Embodiment 2

Figure 34:
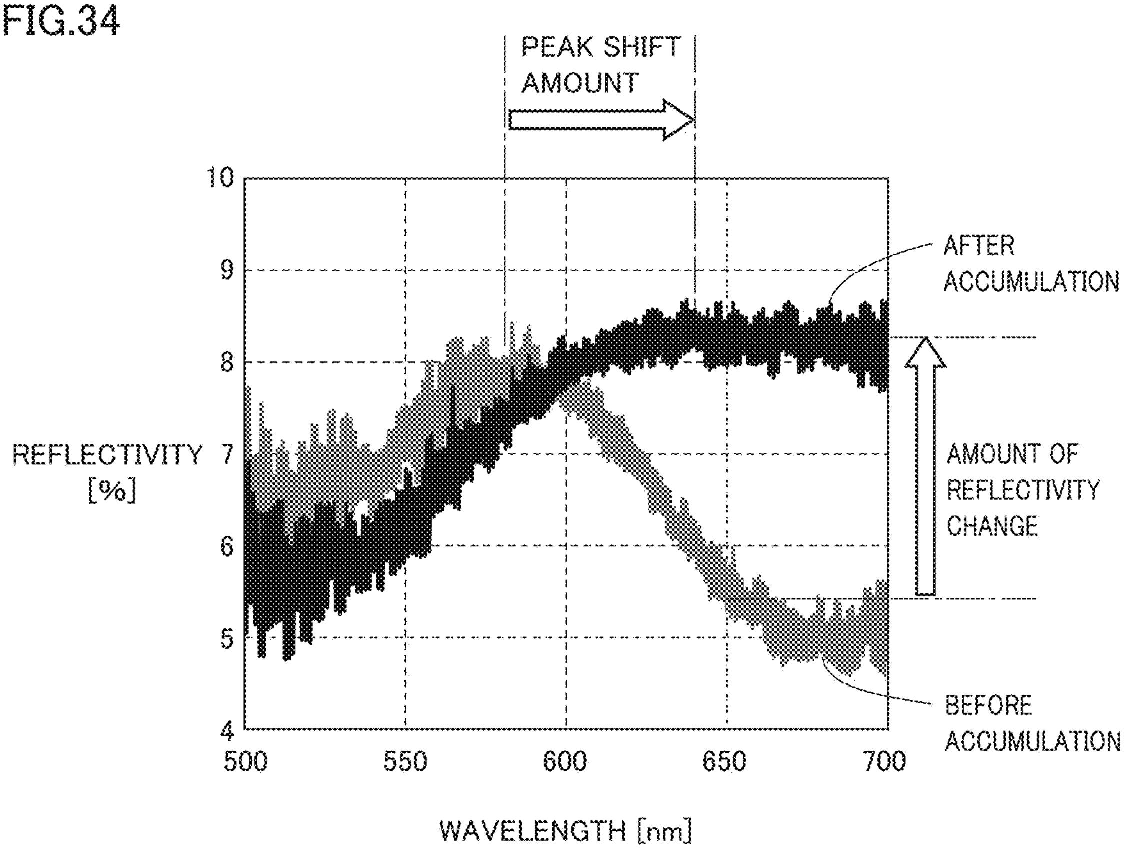
FIG. 34 is a diagram illustrating the images of a bowl region and fluorescent images when first and second samples are separately used.

FIG. 34 is a diagram illustrating an example of a change of the reflection spectrum before and after the accumulation of microscopic objects. Polystyrene beads with a particle size of 100 nm were used as microscopic objects. Water was used as a dispersion medium. The concentration of the polystyrene beads was $4.55\times10^{10}$ [particles/mL]. As shown in FIG. 34, a definite shift of the peak wavelength from the vicinity of 580 nm to the vicinity of 640 nm was confirmed.

Figure 35:
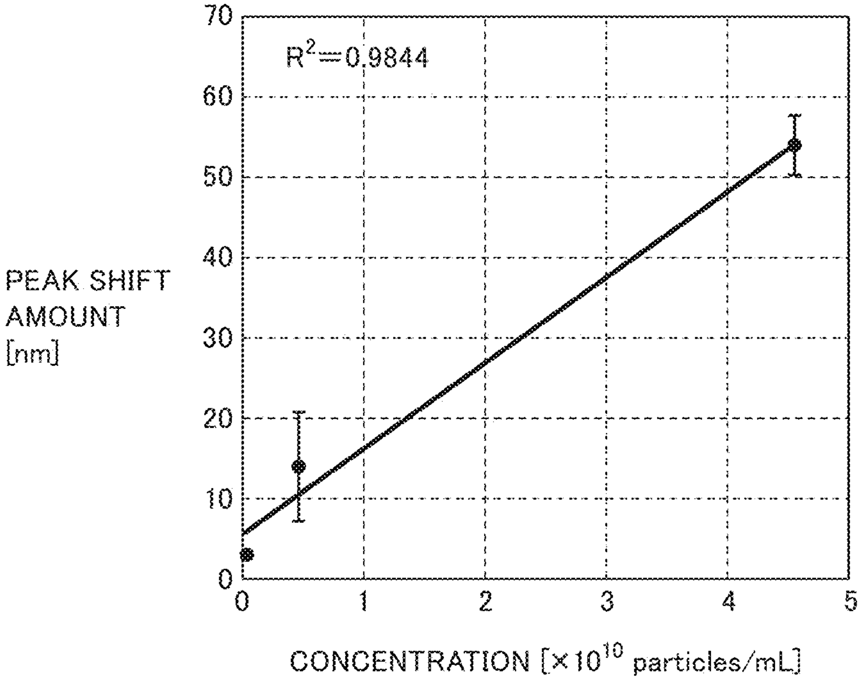
FIG. 35 is a diagram illustrating the images of the bowl region and fluorescent images in a mixed sample containing both of microparticles and nanoparticles.
Figure 36:
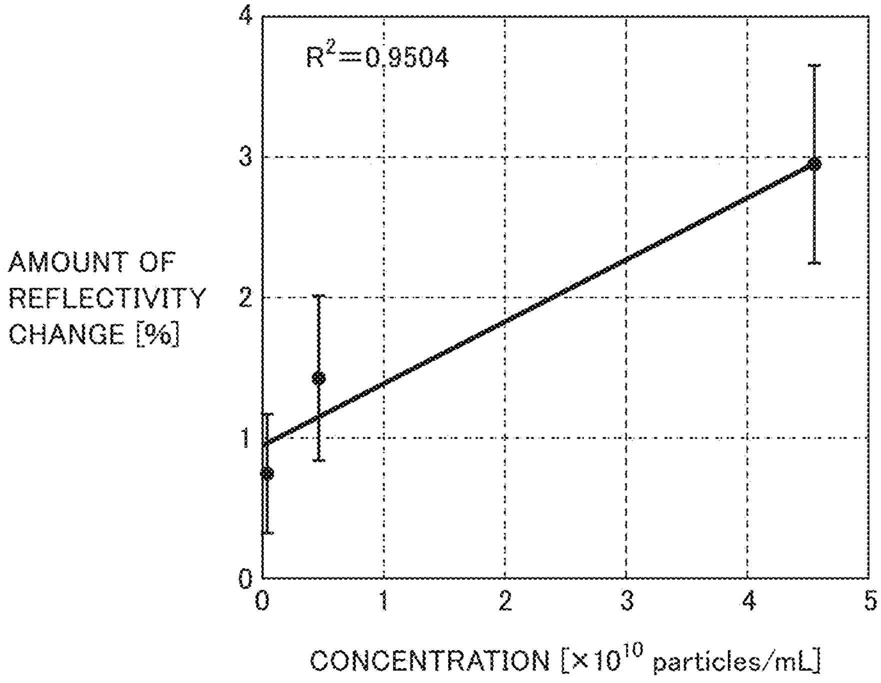
FIG. 36 is a diagram illustrating an example of a calibration curve for calculating the concentration of microscopic objects from an amount of reflectivity change of the reflection spectrum.
Figure 37:
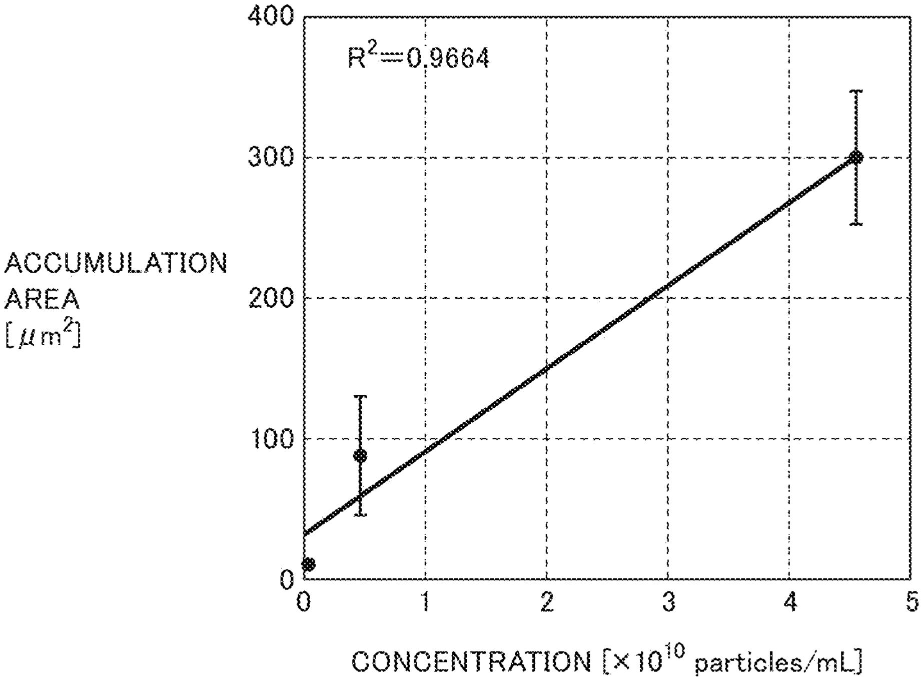
FIG. 37 is a diagram illustrating an example of a calibration curve for calculating the concentration of microscopic objects from an accumulation area of the microscopic objects.

FIG. 35 is a diagram illustrating an example of a calibration curve for calculating the concentration of microscopic objects from a peak shift amount of the reflection spectrum. FIG. 36 is a diagram illustrating an example of a calibration curve for calculating the concentration of microscopic objects from an amount of reflectivity change of the reflection spectrum. FIG. 37 is a diagram illustrating an example of a calibration curve for calculating the concentration of microscopic objects from an accumulation area of the microscopic objects. In FIGS. 35 to 37, the horizontal axis indicates a concentration of microscopic objects. The vertical axis of FIG. 35 indicates a peak shift amount. Adopted as a peak wavelength is a wavelength at which the reflectivity is maximized when Gauss fitting is performed on the reflection spectrum. The vertical axis in FIG. 36 indicates an amount of reflectivity change. In this example, an amount of reflectivity change at a wavelength of 650 nm before and after accumulation was adopted as an amount of reflectivity change. The vertical axis in FIG. 37 indicates an accumulation area of microscopic objects.

Referring to FIGS. 35 to 37, it is understood that three measurement results are linearly obtained according to any one of the three indexes: a peak shift amount, an amount of reflectivity change, and an accumulation area of microscopic objects, and a coefficient $R^2$ of determination is close to 1. Thus, it can be said that microscopic objects contained in the sample can be quantitatively detected according to any one of the three indexes.

As described above, in Embodiment 2, the nano-bowl substrate is used as in Embodiment 1. Thus, a plurality of microscopic objects dispersed in a sample can be efficiently accumulated. Moreover, in Embodiment 2, the reflection spectrum of the bowl region is used instead of the accumulation area of microscopic objects. Also in this case, a plurality of microscopic objects dispersed in a sample can be quickly detected and the content of microscopic objects in a sample can be quantified.

Embodiment 3

In Embodiment 3, a configuration for quantifying the content of microscopic objects in a sample that is a mixture of multiple kinds of microscopic objects will be described. In the following measurement example, a sample containing fluorescent beads was used. Various microscopic objects other than beads can be also labeled with fluorescent dyes.

Two samples were prepared in the first measurement example described below. The first sample contains fluorescent beads (Fluoresbrite BB of Polysciences, Inc.) that emit blue fluorescence. The fluorescent beads are made of polystyrene with a particle size of 1.0 μm. Hereinafter, fluorescent beads with a particle size of 1.0 μm will be also referred to as "microparticles." The concentration of microparticles contained in the first sample was $4.55\times10^{7}$ [particles/mL]. The second sample contains fluorescent beads (Fluoresbrite YG of Polysciences, Inc.) that emit yellow green fluorescence. The fluorescent beads are made of polystyrene with a particle size of 100 nm. Hereinafter, fluorescent beads with a particle size of 100 nm will be also referred to as "nanoparticles." The concentration of nanoparticles contained in the second sample was $4.55\times10^{10}$ [particles/mL].

Figure 38:
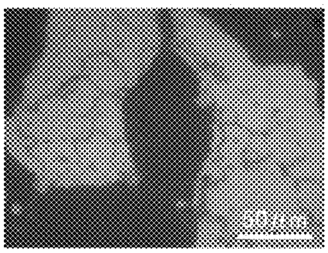
FIG. 38 is a diagram illustrating the images of the bowl region and fluorescent images when the first and second samples are separately used.
Figure 38:
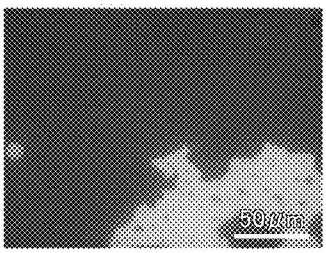
Figure 38:
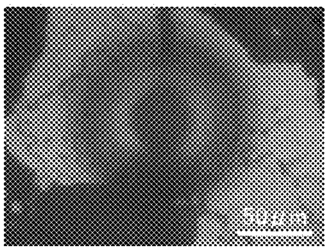
Figure 38:
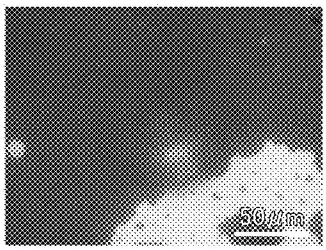
Figure 38:
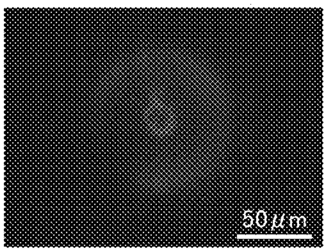
Figure 38:
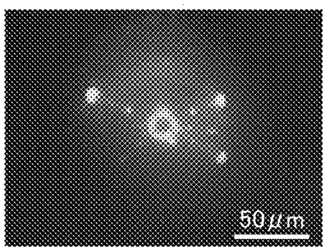

FIG. 38 is a diagram illustrating images of a bowl region and fluorescent images when the first and second samples are separately used. The laser output power was 10 mW. The laser irradiation time was 90 seconds. The laser wavelength was 800 nm. Referring to FIG. 38, it was confirmed that microparticles are accumulated in the bowl region when the first sample is used alone and nanoparticles are accumulated in the bowl region when the second sample is used alone.

Figure 39:
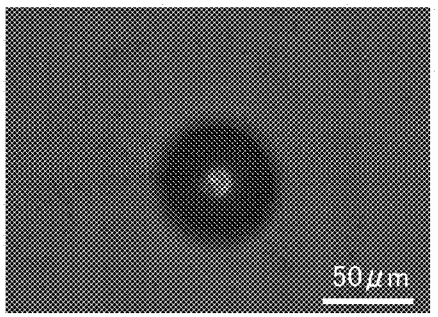
FIG. 39 is a diagram illustrating the images of the bowl region and fluorescent images in a mixed sample containing both of microparticles and nanoparticles.
Figure 39:
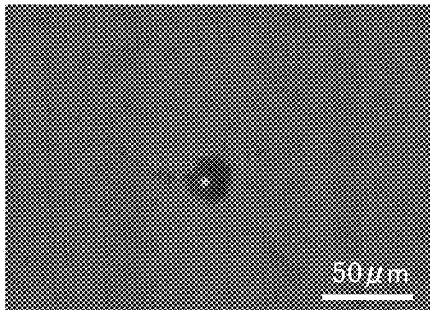
Figure 39:
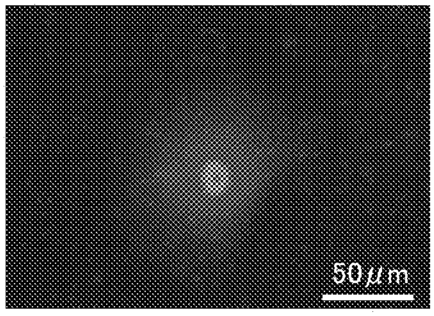
Figure 39:
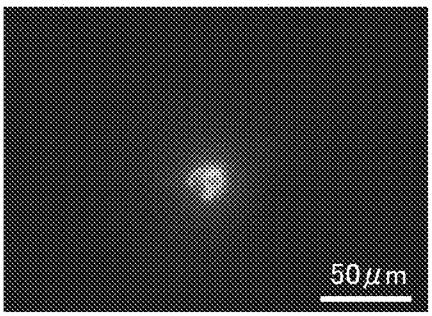
Figure 40:
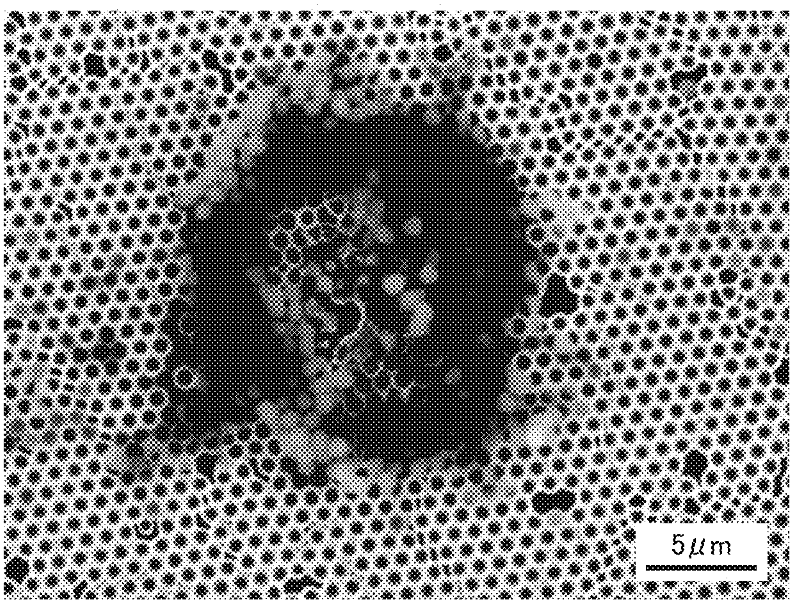
FIG. 40 is an SEM image in which the air-dried bowl region shown in FIG. 39 is observed from directly above.
Figure 41:
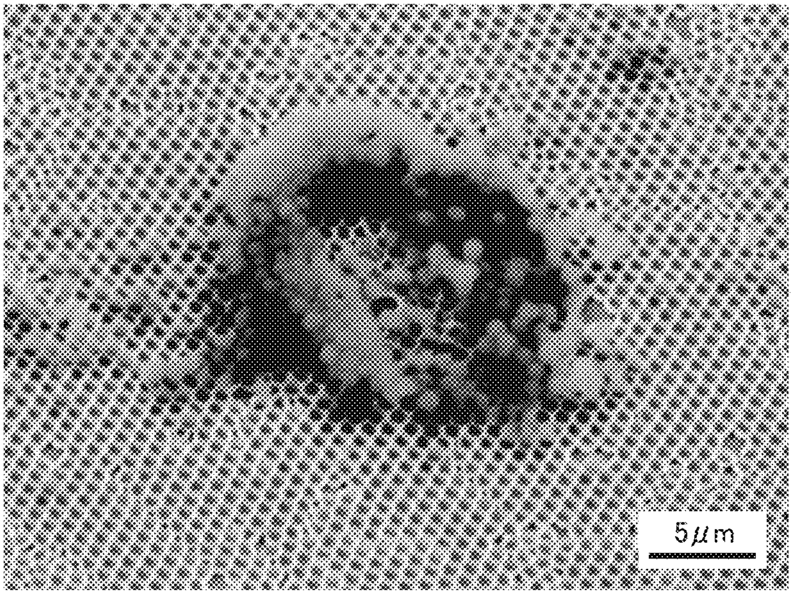
FIG. 41 is an SEM image in which the air-dried bowl region shown in FIG. 39 is observed at an angle of 45° with respect to the principal surface of a detection kit.

FIG. 39 is a diagram illustrating images of the bowl region and fluorescent images in a mixed sample containing both of microparticles and nanoparticles. FIG. 40 is an SEM image in which the air-dried bowl region shown in FIG. 39 is observed from directly above. FIG. 41 is an SEM image in which the air-dried bowl region shown in FIG. 39 is observed at an angle of 45° with respect to the principal surface of a detection kit 10. The ratio of the numbers of microparticles and nanoparticles was 1:1000. In this case, the ratio of the total volume of microparticles contained in the mixed sample (=the volume of each microparticle×the number of microparticles) and the total volume of nanoparticles (=the volume of each nanoparticle×the number of nanoparticles) is 1:1. The laser output power was 10 mW. The laser irradiation time was 90 seconds. The laser wavelength was 1064 nm.

Referring to the fluorescent image shown in FIG. 39, it was confirmed that microparticles and nanoparticles are both accumulated in the bowl region when the first and second samples are mixed. Moreover, it was observed that nanoparticles are accumulated with a higher density than microparticles at the central portion of the bowl region. This proves that the accumulation site of microscopic objects depends upon the sizes of the microscopic objects.

Figure 42:
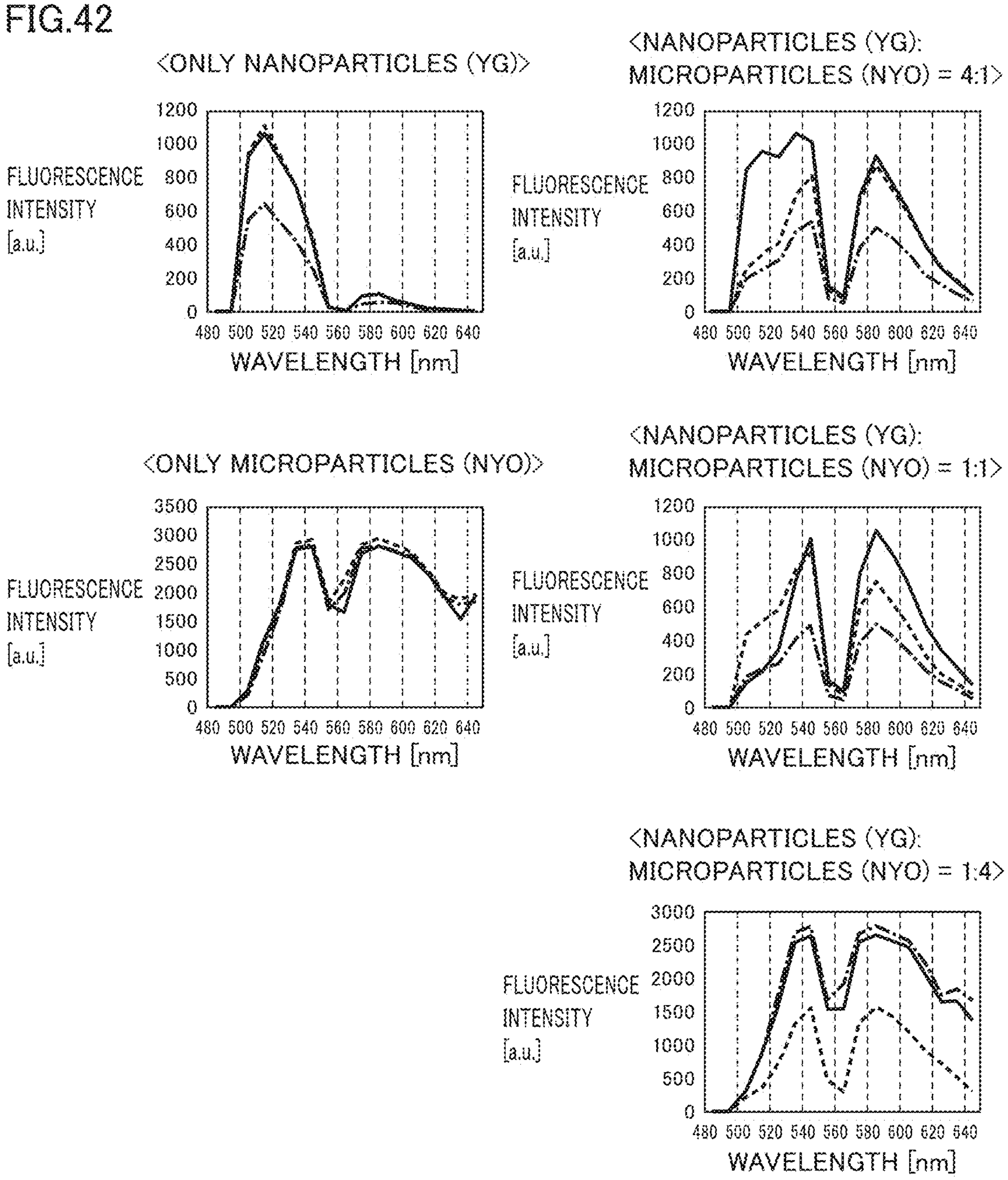
FIG. 42 is a diagram illustrating an example of the measurement results of the fluorescence spectrums of various mixed samples.

FIG. 42 is a diagram illustrating an example of the measurement results of the fluorescence spectrums of various mixed samples. In this example, five samples (third to seventh samples) were prepared. Fluorescent beads contained in the third sample are nanoparticles (Fluoresbrite YG of Polysciences, Inc.) that emit yellow green fluorescence. Fluorescent beads contained in the fourth sample are microparticles (Fluoresbrite NYO of Polysciences, Inc.) that emit yellow orange fluorescence. The fifth sample is a sample containing the two kinds of fluorescent beads (YG and NYO) with a volume ratio of YG:NYO=4:1. The sixth sample is a sample containing the two kinds of fluorescent beads with a volume ratio of YG:NYO=1:1. The seventh sample is a sample containing the two kinds of fluorescent beads with a volume ratio of YG:NYO=1:4. For each of the samples, fluorescence spectrums were measured at three different locations in the bowl region.

As shown in FIG. 42, the fluorescence spectrums considerably vary in shape in each of the samples. This means that microparticles can be selectively detected or nanoparticles can be selectively detected also from a mixture of microparticles and nanoparticles in the fifth to seventh samples. Furthermore, it is also understood that the content ratio (volume ratio) of microparticles and nanoparticles can be determined on the basis of the shape of the fluorescence spectrum.

Figure 43:
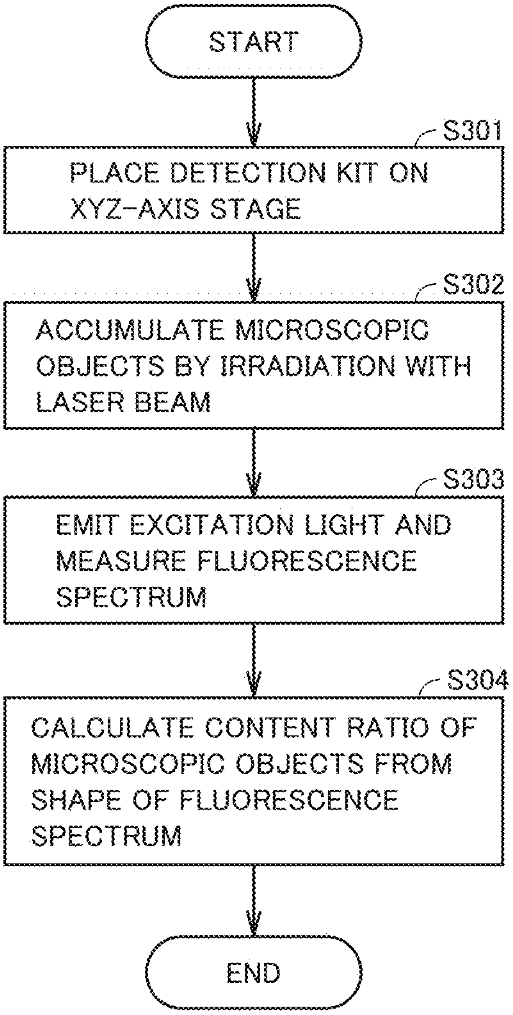
FIG. 43 is a flowchart indicating the steps of a method for detecting microscopic objects according to Embodiment 3.

FIG. 43 is a flowchart indicating the steps of a method for detecting microscopic objects according to Embodiment 3. In S301, detection kit 10 with a sample prepared on a bowl region is placed on an xyz-axis stage 1.

In S302, a controller 9 controls a laser light source 3 so as to output a laser beam with predetermined power for a predetermined time. Thus, microscopic objects are accumulated in a laser spot.

In S303, controller 9 acquires a fluorescence spectrum in the laser spot from a spectrophotometer 7 while controlling an excitation light source 4A to emit excitation light.

In S304, controller 9 calculates the content ratio of microscopic objects contained in the sample by comparing the shape of the fluorescence spectrum with a known spectrum shape. The known spectrum is a spectrum obtained by measuring the fluorescence spectrum described in FIG. 42 in advance. At the completion of the processing of S304, controller 9 returns the processing to the main routine.

As described above, in Embodiment 3, a nano-bowl substrate is used as in Embodiments 1 and 2. Thus, a plurality of microscopic objects dispersed in a sample can be accumulated with high efficiency. Moreover, in Embodiment 3, the fluorescence spectrum of the bowl region is measured. Also in this measurement, a plurality of microscopic objects dispersed in a sample can be quickly detected as in Embodiment 2. By using the fluorescence spectrum, in particular, the content of microscopic objects can be quantified for each kind (size) of microscopic objects in a sample that is a mixture of multiple kinds of microscopic objects. Thus, even if a sample contains an impurity other than microscopic objects to be detected, the microscopic objects to be detected can be selectively quantified.

Embodiment 4

In Embodiment 4, a method for fabricating a transmission detection kit will be described.

Figure 44:
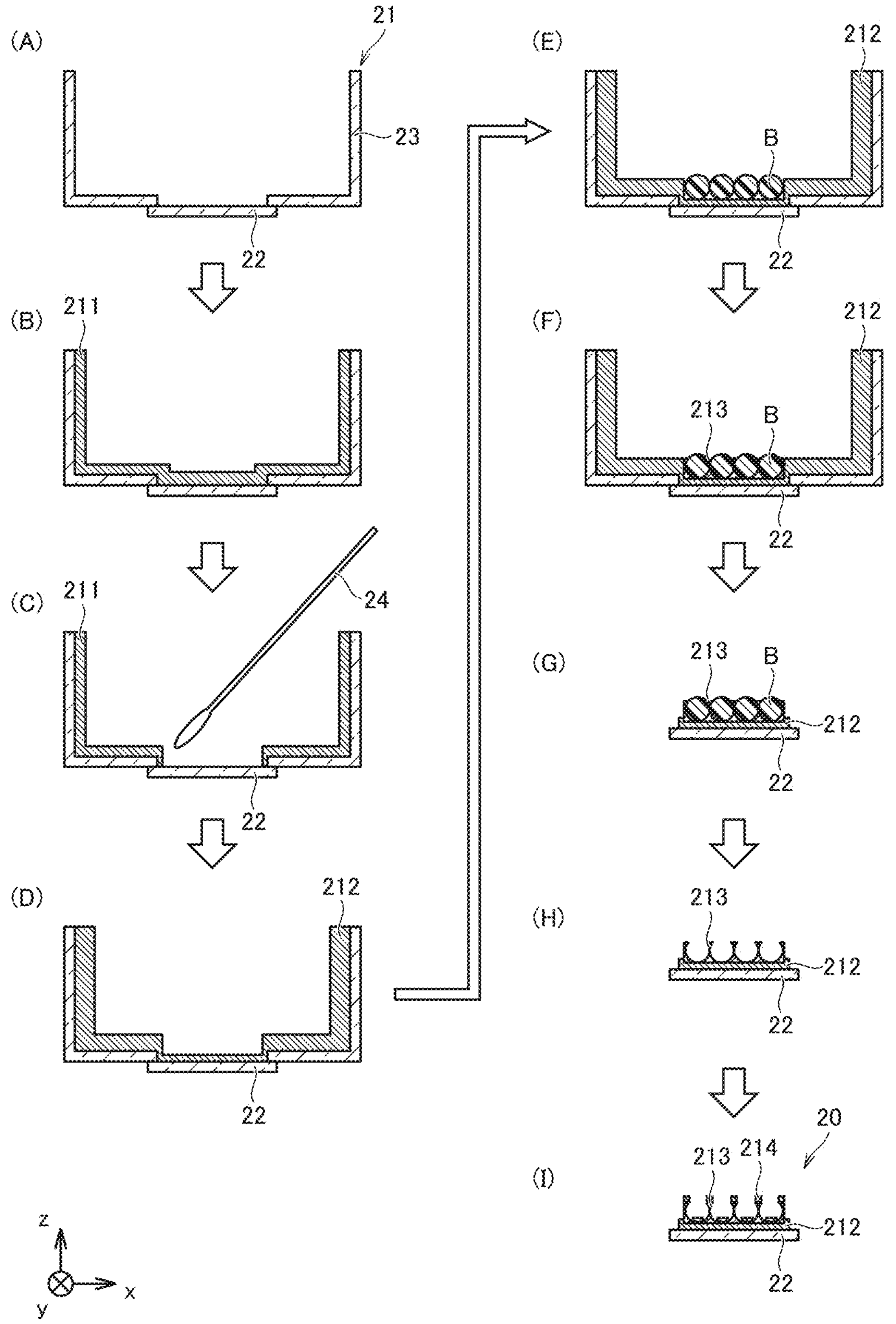
FIG. 44 is a schematic process drawing of a method for fabricating a detection kit according to Embodiment 4.

FIG. 44 is a schematic process drawing of a method for fabricating the detection kit according to Embodiment 4. Referring to FIG. 44(A), a glass bottom dish 21 that is a cylindrical container with an upper opening is prepared in this example. Glass bottom dish 21 includes a well (measurement hole) 22 provided at the center of the bottom surface of glass bottom dish 21 and a dish portion 23 around well 22.

First, a metallic thin film 211 is formed over the inner surface (top surface) of glass bottom dish 21 by, for example, ion sputtering, vacuum deposition, or electroless plating (see FIG. 44(B)). For example, a thin gold film having a thickness of 50 nm can be formed.

Subsequently, as illustrated in FIG. 44(C), metallic thin film 211 formed in well 22 is removed. For example, metallic thin film 211 can be removed by making contact with a swab 24 dampened with ethanol. At this point, metallic thin film 211 is desirably left around well 22 so as to keep an electrical connection (electrical continuity of metallic thin film 211) between the outer periphery (an end region connected to the dish portion 23) of well 22 and dish portion 23.

In FIG. 44(D), a metallic thin film 212 is additionally formed over the inner surface of glass bottom dish 21. Metallic thin film 212 formed as the second film desirably has a smaller thickness than the thickness of metallic thin film 211 formed as the first film. In this example, the first thin gold film has a thickness of 50 nm, whereas the second thin gold film has a thickness of 10 nm.

Thereafter, a dispersion liquid containing dispersed resin beads (denoted as B) is dropped onto metallic thin film 212 formed in well 22. The size and material of the resin beads are the same as those in the description of FIG. 6. For example, polystyrene beads with a diameter of 500 nm can be used. When the dispersion liquid is air-dried at room temperature, the resin beads are periodically arranged like a single layer on metallic thin film 212 by self-organization (see FIG. 44(E)). Thus, a single-layer film of the resin beads is formed in well 22. Other methods such as lithography may be used instead of self-organization.

In FIG. 44(F), a conductive polymer film 213 is formed to fill the gaps of the single-layer film of the resin beads and expose a part of the surface of each resin bead. For example, as in the description of FIG. 6, a polypyrrole film 213 can be formed by performing electrolytic polymerization for 30 seconds.

Thereafter, well 22 is peeled off from glass bottom dish 21 (dish portion 23) (see FIG. 44(G)). For example, well 22 can be peeled off from glass bottom dish 21 by applying a physical force with tweezers (not illustrated).

The resin beads can be removed by selectively melting the resin beads with a solvent in which the material of the resin beads is more soluble than the material of conductive polymer film 213 (see FIG. 44(H)). For example, the resin beads can be removed by immersion in a chloroform solution for one minute.

Finally, a metallic thin film 214 is further formed on conductive polymer film 213 (see FIG. 44(I)). Also for this processing, methods such as ion sputtering, vacuum deposition, and electroless plating can be used. Metallic thin film 214 formed as the third film has a thickness of, for example, 10 nm. Thus, a transmission detection kit 20 is completed.

Figure 45:
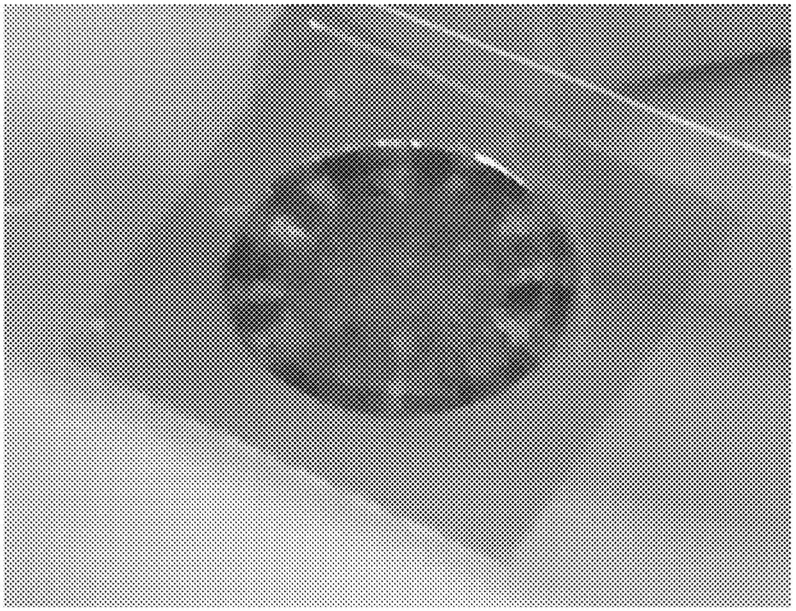
FIG. 45 is a diagram illustrating an image of the detection kit fabricated by the fabrication method illustrated in FIG. 44.

FIG. 45 is a diagram illustrating an image of detection kit 20 fabricated by the fabrication method illustrated in FIG. 44. From FIG. 45, it is understood that a finger (see the upper right) holding detection kit 20 is shown through translucent detection kit 20. Thus, detection kit 20 fabricated in Embodiment 4 is a transmission type.

Figure 46:
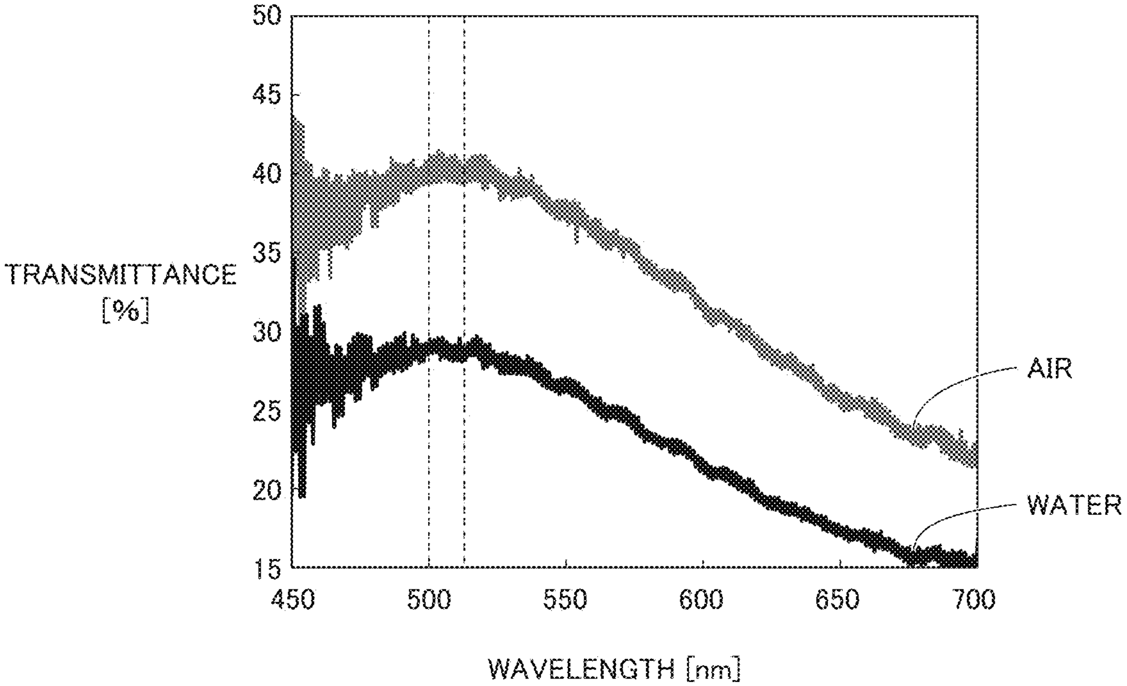
FIG. 46 is a diagram illustrating an example of measurement results on the transmission spectrum of the transmission detection kit.

FIG. 46 is a diagram illustrating an example of measurement results on the transmission spectrum of transmission detection kit 20. Air or water (not containing microscopic objects) was used as a sample. The transmission spectrum was measured in both of air and water. The two transmission spectrums are similar in shape. In the case of a water sample, the intensity of the overall transmission spectrum decreased as compared with an air sample.

The result of laser irradiation in transmission detection kit 20 will be described below. As in the foregoing example, nanoparticles (fluorescent beads that emit yellow green fluorescence) with a particle size of 100 nm were used. The concentration of the nanoparticles was $4.55\times10^{11}$ [particles/mL].

Figure 47:
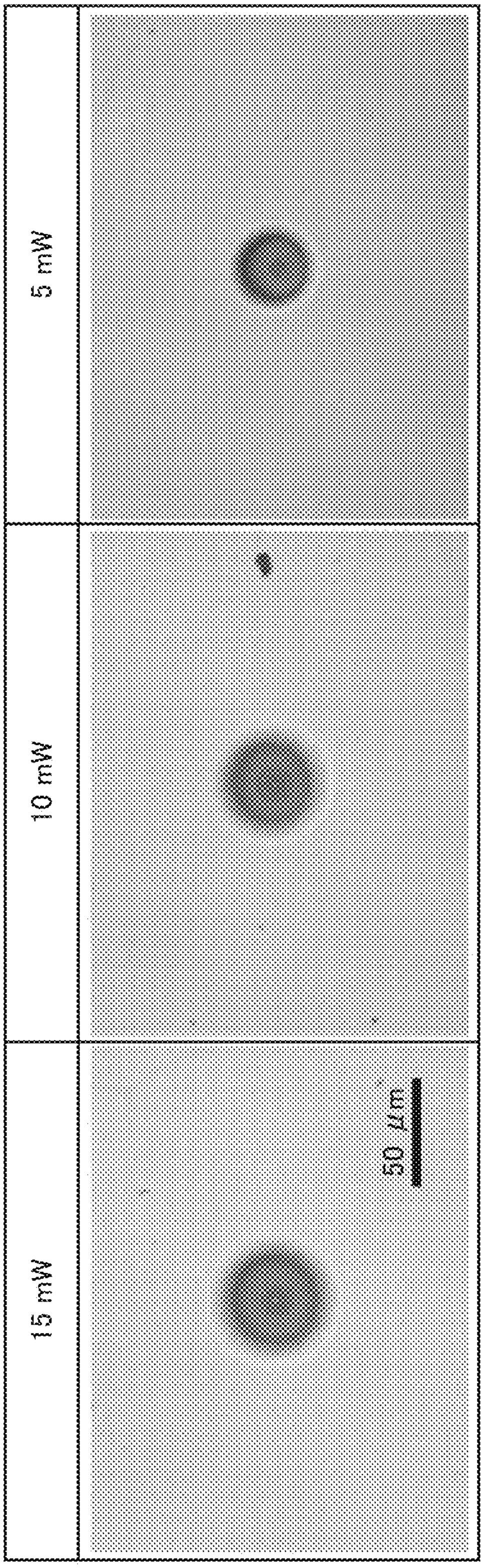
FIG. 47 is a diagram illustrating laser spot images in the transmission detection kit.

FIG. 47 is a diagram illustrating laser spot images in transmission detection kit 20. In the overall configuration diagram (see FIG. 1) described in Embodiment 1, a laser beam is emitted from above to a surface (front side) of detection kit 10 located below. In this example, according to a characteristic of the transmission detection kit, a laser beam, which is not illustrated, was emitted from below to the back side (undersurface) of detection kit 20 located above. The laser output power was set at 15 mW, 10 mW, or 5 mW. The laser irradiation time was 60 seconds. The laser wavelength was 800 nm.

As shown in FIG. 47, it was confirmed that microbubbles are generated at the laser output power of 5 mW. This suggests that in irradiation using transmission detection kit 20 in the upward direction, microbubbles may be generated even with lower laser output power than in irradiation using the non-transmission (reflection) detection kit 10 in the downward direction as in Embodiment 1. Moreover, an observation can be more advantageously performed from below than from above depending upon the kind of object (adherent cell or the like) to be detected.

Figure 48:
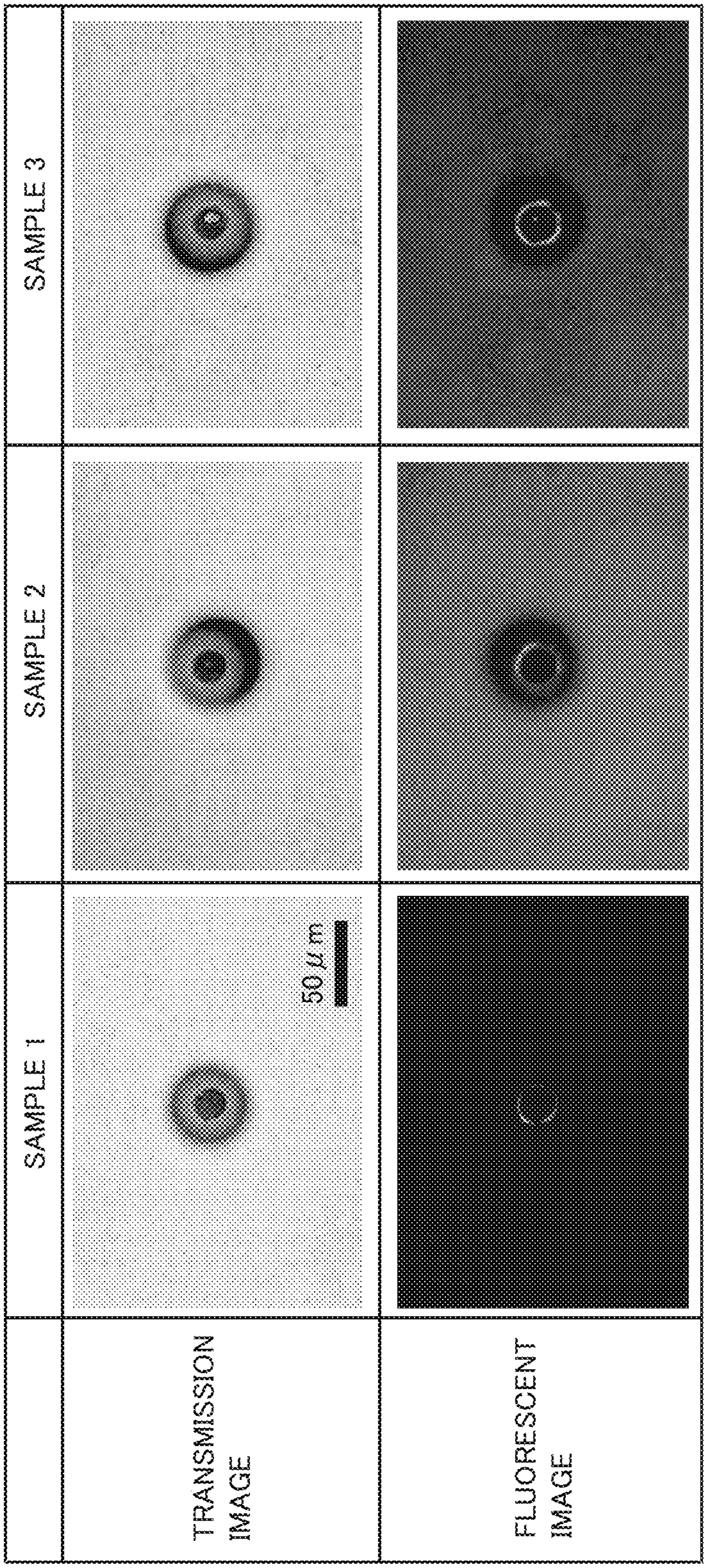
FIG. 48 is a diagram illustrating the result of accumulation of nanoparticles by the transmission detection kit.

FIG. 48 is a diagram illustrating the result of accumulation of nanoparticles by transmission detection kit 20. Also in this example, a laser beam was emitted from below to detection kit 20 located above. The laser output power was set at 10 mW. The laser irradiation time was 60 seconds. The laser wavelength was 800 nm. As shown in FIG. 48, it was confirmed that also when transmission detection kit 20 is used, nanoparticles can be detected by a fluorescent image through light concentration.

Transmission detection kit 20 is fabricated thus in Embodiment 4. By using transmission detection kit 20, microscopic objects can be accumulated by laser irradiation to the back side from below in addition to laser irradiation to the surface (front side) from above.

[Supplement]

Finally, the aspects of the present disclosure will be collectively described.

(Supplement 1)

A method for accumulating a plurality of microscopic objects dispersed in a liquid sample, the method comprising:
- preparing the liquid sample in contact with a photothermal conversion region; and
- irradiating the photothermal conversion region with light having a wavelength within an absorption wavelength range of the photothermal conversion region to generate a bubble in an irradiation region of the light and accumulate the plurality of microscopic objects around the bubble,
- wherein the photothermal conversion region includes:
  - a first thin film having a first material that converts the light into heat;
  - a structure in which a plurality of non-penetrating pores are periodically arranged on the first thin film; and
  - a second thin film having a second material that converts the light into heat, the second thin film being disposed on at least a part of the structure, and
- wherein sizes of the plurality of non-penetrating pores and the irradiation region are determined such that at least two of the plurality of non-penetrating pores are entirely included in the irradiation region in a top view of the photothermal conversion region.

(Supplement 2)

The method for accumulating microscopic objects according to Supplement 1, wherein the plurality of non-penetrating pores are disposed at positions of lattice points periodically located in a two-dimensional array, and
- the sizes of the plurality of non-penetrating pores and the irradiation region are determined such that all of the non-penetrating pores disposed at positions of lattice points of at least one unit lattice are entirely included in the irradiation region.

(Supplement 3)

The method for accumulating microscopic objects according to Supplement 2, wherein the plurality of non-penetrating pores are disposed in a honeycomb pattern, and
- the sizes of the plurality of non-penetrating pores and the irradiation region are determined such that at least six non-penetrating pores disposed at positions of lattice points of a honeycomb lattice are entirely included in the irradiation region.

(Supplement 4)

The method for accumulating microscopic objects according to any one of Supplements 1 to 3, wherein the plurality of non-penetrating pores are recesses, each having an inner wall surface forming a bowl-like structure.

(Supplement 5)

The method for accumulating microscopic objects according to Supplement 4, wherein the bowl-like structure is a recess of spherical segment shape deeper than a hemisphere.

(Supplement 6)

The method for accumulating microscopic objects according to Supplement 5, wherein the second thin film includes:
- a third thin film disposed outside the bowl-like structure; and
- a fourth thin film disposed inside the bowl-like structure.

(Supplement 7)

The method for accumulating microscopic objects according to any one of Supplements 1 to 6, wherein the plurality of non-penetrating pores have pore sizes smaller than a center wavelength of the light.

(Supplement 8)

The method for accumulating microscopic objects according to any one of Supplements 1 to 7, wherein the irradiating with the light further includes standing by until the bubble shrinks after stopping light irradiation.

(Supplement 9)

The method for accumulating microscopic objects according to any one of Supplements 1 to 8, wherein the photothermal conversion region is configured to be translucent in a top view of the photothermal conversion region, and
- the irradiating with the light further includes irradiating an undersurface of the photothermal conversion region with the light.

(Supplement 10)

A method for detecting microscopic objects, including:
- the method for accumulating microscopic objects according to any one of Supplements 1 to 9;
- detecting, by a receiver, light from the liquid sample irradiated with the light; and
- detecting the plurality of microscopic objects in the liquid sample on a basis of a signal from the receiver.

(Supplement 11)

The method for detecting microscopic objects according to Supplement 10, wherein the receiver includes a camera, and
- the detecting the plurality of microscopic objects includes:
  - calculating the accumulation area of the plurality of microscopic objects from an image captured by the camera; and
  - calculating a concentration of the plurality of microscopic objects contained in the liquid sample from the calculated accumulation area by referring to a predetermined correlation between the concentration of the plurality of microscopic objects and the accumulation area of the plurality of microscopic objects.

(Supplement 12)

The method for detecting microscopic objects according to Supplement 11, wherein the plurality of microscopic objects include at least one of a plurality of viruses, a plurality of proteins, a plurality of antibodies, and a plurality of composites each containing a protein and an antibody, and prior to the irradiating with the light, the detecting method further includes:

preparing another liquid sample containing a plurality of fine particles, each modified by a host substance specifically bound to a corresponding microscopic object among the plurality of microscopic objects;

preparing the other liquid sample in contact with the photothermal conversion region; and irradiating the photothermal conversion region with the light having a wavelength within an absorption wavelength range of the photothermal conversion region to generate the bubble in the irradiation region of light and accumulate the plurality of fine particles around the bubble.

(Supplement 13)

The method for detecting microscopic objects according to Supplement 10, wherein the receiver includes a spectroscope configured to measure reflected light, and the detecting the plurality of microscopic objects includes measuring, by the spectroscope, a reflection spectrum at an accumulation position of the plurality of microscopic objects.

(Supplement 14)

The method for detecting microscopic objects according to Supplement 13, wherein the detecting includes:

calculating a peak shift amount or an amount of reflectivity change of the reflection spectrum; and calculating the concentration of the plurality of microscopic objects contained in the liquid sample from the calculated peak shift amount or the amount of reflectivity change by referring to a predetermined correlation between the concentration of the plurality of microscopic objects and the peak shift amount or the amount of reflectivity change.

(Supplement 15)

The method for detecting microscopic objects according to Supplement 10, wherein the plurality of microscopic objects include:

a plurality of first objects that emit fluorescence with a predetermined wavelength; and a plurality of second objects that emit fluorescence with a wavelength different from the predetermined wavelength and are smaller than the plurality of first objects, the receiver includes a spectroscope configured to measure fluorescence, and the detecting the plurality of microscopic objects includes:

measuring, by the spectroscope, a fluorescence spectrum at an accumulation position of the plurality of microscopic objects; and calculating a ratio of the plurality of first objects and the plurality of second objects that are contained in the liquid sample, on a basis of the fluorescence spectrum.

(Supplement 16)

A method for fabricating a detection kit for detecting an analyte which may be contained in a liquid sample, the method comprising:

forming a first metallic thin film on a top surface of a substrate;

removing, from the first metallic thin film, a metallic thin film formed in a predetermined region on the top surface;

forming a second metallic thin film on the top surface including the predetermined region;

periodically arranging a plurality of fine particles on the second metallic thin film formed in the predetermined region;

forming a conductive thin film so as to partially expose the surfaces of the plurality of fine particles;

forming a plurality of recesses on the conductive thin film by removing the plurality of fine particles using a solution; and forming a third metallic thin film on at least some of the plurality of recesses.

(Supplement 17)

A method for accumulating a plurality of microscopic objects dispersed in a liquid sample, the method comprising:

preparing a detection kit fabricated according to the fabrication method according to Supplement 16;

preparing the liquid sample in contact with a photothermal conversion region disposed on the front surface of the detection kit; and irradiating the photothermal conversion region from the back surface of the detection kit with light having a wavelength within the absorption wavelength range of the photothermal conversion region to generate a bubble in an irradiation region of the light and accumulate the plurality of microscopic objects around the bubble.

It should be understood that the disclosed embodiments are merely exemplary and are not restrictive in all the aspects. The scope of the present disclosure is not indicated by the description of the embodiments but the claims. The scope of the present disclosure is intended to include meanings equivalent to the claims and all changes in the scope thereof.

INDUSTRIAL APPLICABILITY

The present disclosure is usable in a form of quickly detecting microscopic objects with high sensitivity by accumulating various microscopic objects (e.g., toxic fine particles such as PM2.5, environmental load substances such as microplastics or nano-plastics, or various germs or viruses) dispersed in a liquid sample with high efficiency. The present disclosure is also usable for determining whether microscopic objects are included in a liquid sample and/or specifying the concentration of microscopic objects in a liquid sample. For example, the present disclosure can be effectively used for a test of the novel coronavirus.

REFERENCE SIGNS LIST

1 xyz-axis stage; 2 Adjusting mechanism; 3 Laser light source; 31 Lens; 4 Illumination light source; 4A Excitation light source; 5 Objective lens; 6 Imaging device; 61 Lens; 62 Fluorescence filter; 7 Spectrophotometer; 71 Lens; 81 Dichroic mirror; 82, 83 Half mirror; 9 Controller; 91 Processor; 92 Memory; 93 Input/output port; 10 Detection kit; 11 Bottom portion; 12 Top portion; 13 Side portion; 110 Substrate; 111, 113 Metallic thin film; 112 Conductive polymer film; 20 Transmission detection kit; 21 Glass bottom dish; 22 Well; 23 Dish portion; 24 Swab; 211, 212, 214 metallic thin film; 213 Conductive polymer film; 100, 101 Detection system

The invention claimed is:

1. A method for accumulating a plurality of microscopic objects dispersed in a liquid sample, the method comprising:

preparing the liquid sample in contact with a photothermal conversion region; and irradiating the photothermal conversion region with light having a wavelength within an absorption wavelength range of the photothermal conversion region to generate a bubble in an irradiation region of the light and accumulate the plurality of microscopic objects around the bubble, wherein the photothermal conversion region includes:

a first thin film having a first material configured to convert the light into heat;

a structure in which a plurality of non-penetrating pores are periodically arranged on the first thin film; and a second thin film having a second material configured to convert the light into heat, the second thin film being disposed on at least a part of the structure, and wherein sizes of the plurality of non-penetrating pores and the irradiation region are determined such that at least two of the plurality of non-penetrating pores are entirely included in the irradiation region in a top view of the photothermal conversion region.

2. The method for accumulating microscopic objects according to claim 1, wherein the plurality of non-penetrating pores are disposed at positions of lattice points periodically located in a two-dimensional array, and the sizes of the plurality of non-penetrating pores and the irradiation region are determined such that all of the non-penetrating pores disposed at positions of lattice points of at least one unit lattice are entirely included in the irradiation region.

3. The method for accumulating microscopic objects according to claim 2, wherein the plurality of non-penetrating pores are disposed in a honeycomb pattern, and the sizes of the plurality of non-penetrating pores and the irradiation region are determined such that at least six non-penetrating pores disposed at positions of lattice points of a honeycomb lattice are entirely included in the irradiation region.

4. The method for accumulating microscopic objects according to claim 1, wherein the plurality of non-penetrating pores are recesses, each having an inner wall surface forming a bowl-like structure.

5. The method for accumulating microscopic objects according to claim 4, wherein the bowl-like structure is a recess of spherical segment shape deeper than a hemisphere.

6. The method for accumulating microscopic objects according to claim 5, wherein the second thin film includes:

a third thin film disposed outside the bowl-like structure; and a fourth thin film disposed inside the bowl-like structure.

7. The method for accumulating microscopic objects according to claim 1, wherein the plurality of non-penetrating pores have pore sizes smaller than a center wavelength of the light.

8. The method for accumulating microscopic objects according to claim 1, wherein the irradiating with the light further includes standing by until the bubble shrinks after stopping light irradiation.

9. The method for accumulating microscopic objects according to claim 1, wherein the photothermal conversion region is configured to be translucent in a top view of the photothermal conversion region, and the irradiating with the light further includes irradiating an undersurface of the photothermal conversion region with the light.

10. A method for detecting microscopic objects, comprising:

the method for accumulating microscopic objects according to claim 1;

detecting, by a receiver, light from the liquid sample irradiated with the light; and detecting the plurality of microscopic objects in the liquid sample on a basis of a signal from the receiver.

11. The method for detecting microscopic objects according to claim 10, wherein the receiver includes a camera, and the detecting the plurality of microscopic objects includes:

calculating an accumulation area of the plurality of microscopic objects from an image captured by the camera; and calculating a concentration of the plurality of microscopic objects contained in the liquid sample from the calculated accumulation area by referring to a predetermined correlation between the concentration of the plurality of microscopic objects and the accumulation area of the plurality of microscopic objects.

12. The method for detecting microscopic objects according to claim 11, wherein the plurality of microscopic objects include at least one of a plurality of viruses, a plurality of proteins, a plurality of antibodies, and a plurality of composites each containing a protein and an antibody, and prior to the irradiating with the light, the detecting method further comprises:

preparing another liquid sample in contact with the photothermal conversion region, the other liquid sample containing a plurality of fine particles each modified by a host substance specifically bound to a corresponding microscopic object among the plurality of microscopic objects; and irradiating the photothermal conversion region with the light to generate the bubble in the irradiation region and accumulate the plurality of fine particles around the bubble.

13. The method for detecting microscopic objects according to claim 10, wherein the receiver includes a spectroscope configured to measure reflected light, and the detecting the plurality of microscopic objects includes measuring, by the spectroscope, a reflection spectrum at an accumulation position of the plurality of microscopic objects.

14. The method for detecting microscopic objects according to claim 13, wherein the detecting includes:

calculating a peak shift amount or an amount of reflectivity change of the reflection spectrum; and calculating a concentration of the plurality of microscopic objects contained in the liquid sample from the calculated peak shift amount or the amount of reflectivity change by referring to a predetermined correlation between the concentration of the plurality of microscopic objects and the peak shift amount or the amount of reflectivity change.

15. The method for detecting microscopic objects according to claim 10, wherein the plurality of microscopic objects include:

a plurality of first objects configured to emit fluorescence with a predetermined wavelength; and a plurality of second objects configured to emit fluorescence with a wavelength different from the predetermined wavelength and are smaller than the plurality of first objects, and wherein the receiver includes a spectroscope configured to measure fluorescence, and the detecting the plurality of microscopic objects includes: measuring, by the spectroscope, a fluorescence spectrum at an accumulation position of the plurality of microscopic objects; and calculating a ratio of the plurality of first objects and the plurality of second objects that are contained in the liquid sample, on a basis of the fluorescence spectrum.

* * * * *